US011442046B2

(12) United States Patent
Carell et al.

(10) Patent No.: US 11,442,046 B2
(45) Date of Patent: Sep. 13, 2022

(54) REAGENT FOR MASS SPECTROMETRY

(71) Applicants: Roche Diagnostics Operations, Inc., Indianapolis, IN (US); Ludwig-Maximilians-Universitaet Muenchen, Munich (DE)

(72) Inventors: Thomas Carell, Krailling (DE); Uwe Kobold, Penzberg (DE); Dieter Heindl, Penzberg (DE); Silvia Baecher, Penzberg (DE); Andreas Leinenbach, Penzberg (DE); Martin Rempt, Penzberg (DE); Toni Pfaffeneder, Munich (DE); Angie Kirchner, Munich (DE); Olesea Kosmatchev, Augsburg (DE); Rene Rahimoff, Munich (DE); Sarah Schiffers, Munich (DE); Markus Muller, Munich (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 437 days.

(21) Appl. No.: 16/520,696

(22) Filed: Jul. 24, 2019

(65) Prior Publication Data

US 2020/0041470 A1 Feb. 6, 2020

Related U.S. Application Data

(63) Continuation of application No. PCT/EP2018/052451, filed on Jan. 31, 2018.

(30) Foreign Application Priority Data

Jan. 31, 2017 (EP) ..................................... 17153895

(51) Int. Cl.
*G01N 30/72* (2006.01)
*C07D 249/04* (2006.01)
(Continued)

(52) U.S. Cl.
CPC ........... *G01N 30/72* (2013.01); *C07D 249/04* (2013.01); *H01J 49/0045* (2013.01);
(Continued)

(58) Field of Classification Search
None
See application file for complete search history.

(56) References Cited

U.S. PATENT DOCUMENTS

| 6,228,654 B1 | 5/2001 | Chait et al. |
| 2004/0157344 A1 | 8/2004 | Wang |

(Continued)

FOREIGN PATENT DOCUMENTS

| WO | 2004070352 A2 | 8/2004 |
| WO | 2011029639 A2 | 3/2011 |

(Continued)

OTHER PUBLICATIONS

European Search Report dated May 17, 2017, in Application No. 17153895.2, 11 pp.

(Continued)

*Primary Examiner* — Xiaoyun R Xu
(74) *Attorney, Agent, or Firm* — Stinson LLP

(57) ABSTRACT

The present invention relates to reagents suitable in the mass spectrometric determination of analyte molecules such as carbohydrates as well as adducts of such reagents and analyte molecules and applications of said reagents and adducts. Further, the present invention relates to methods for the mass spectrometric determination of analyte molecules.

20 Claims, 21 Drawing Sheets

Figure 1:
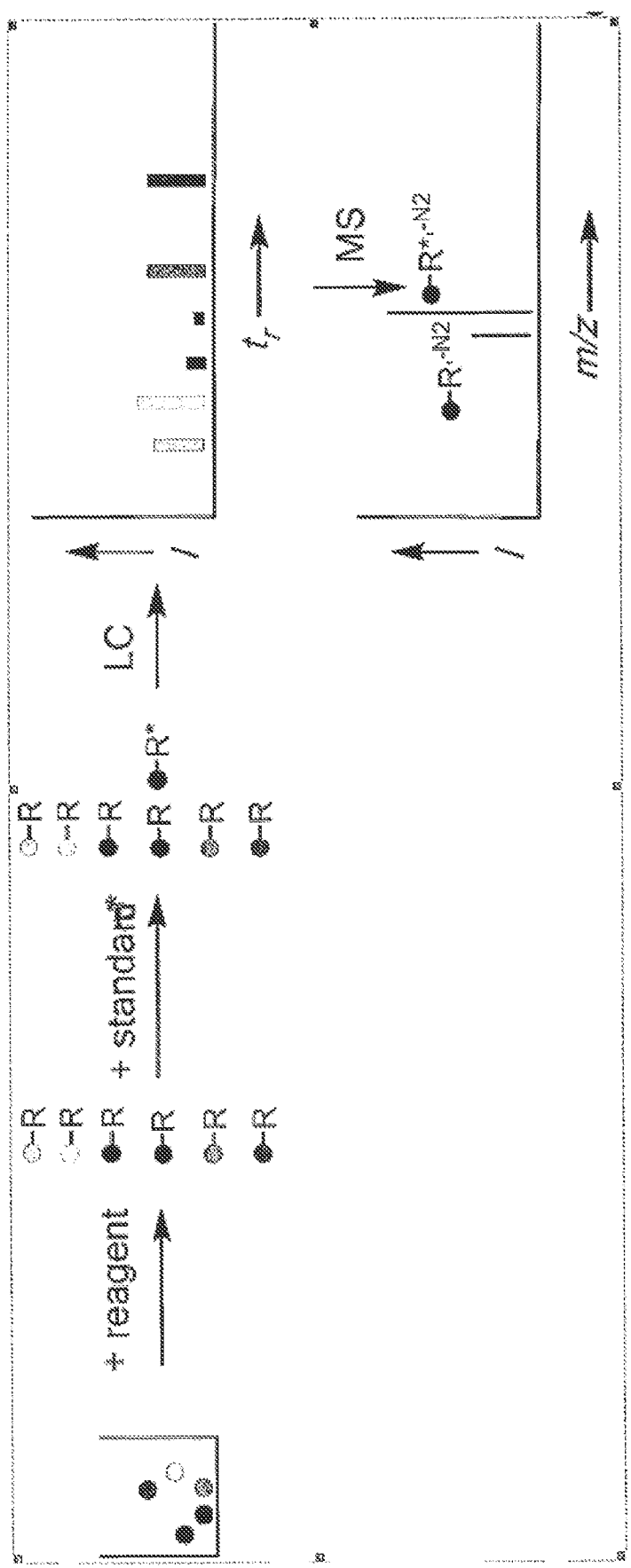

(51) Int. Cl.
 H01J 49/00 (2006.01)
 H01J 49/06 (2006.01)
 H01J 49/10 (2006.01)
(52) U.S. Cl.
 CPC ............ *H01J 49/063* (2013.01); *H01J 49/10* (2013.01); *G01N 2400/00* (2013.01); *G01N 2458/15* (2013.01)

(56) References Cited

U.S. PATENT DOCUMENTS

| | | |
|---|---|---|
| 2011/0143951 A1 | 6/2011 | Thompson |
| 2014/0004616 A1 | 1/2014 | Subhakar |
| 2014/0227793 A1 | 8/2014 | Gao et al. |

FOREIGN PATENT DOCUMENTS

| | | |
|---|---|---|
| WO | 2013/037289 A1 | 3/2013 |
| WO | 2013108113 A1 | 7/2013 |
| WO | 2014153164 A1 | 9/2014 |
| WO | 2017044828 A1 | 3/2017 |

OTHER PUBLICATIONS

Giorgi, Gianluca, Mass spectrometry of hydroxylamines, oximes and hydroxamic acids, Patai's Chemistry of Functional Groups, Online, 2010, 55 pp.
Branson et al., A Protein-Based Pentavalent Inhibitor of th eCholera Toxin B-Subunit; Angew. Chem. Int. Ed, 2014, vol. 53, pp. 8323-8327.
Knighton et al., Laboratory Evaluation of an Aldehyde Scrubber System Specifically for the Detection of Acrolein; Journal of the Air & Waste Management Association; 10-pages.
Lavrynenko et al., Girard derivatization for LC-MS/MS profiling of endogenous ecdysteroids in *Drosophila*; Journal of Lipid Research, vol. 54, pp. 2265-2272.
Li et al., Combination of pentafluorophenylhydrazine derivatization and isotope dilution LC-MS/MS techniques for the quantification of apurinic/apyrimidinic sites in cellular DNA; Anal Bioanal Chem, 2013, vol. 405, pp. 4059-4066.
Maier et al., Protein Adducts of Aldehydic Lipid Peroxidation Products: Identification and Characterization of Protein Adducts Using An Aldehyde/Keto Reactive Probe in Combination With Mass Spectrometry; Methods Enzymol., 2010, vol. 476, pp. 305-330.
Reis et al., Detection and characterization of cyclic hydroxylamine adducts by mass spectrometry; Free Radical Research, 2008, vol. 42, No. 5, pp. 481-491.
Ridpath, J.R., Detecting DNA Damage: The Synthesis Of New Aldehyde Reactive Probes For The Quantitation Of Apurinic/Apyrimidinic Sites; 77-pages.
Sohn et al., Designer Reagents for Mass Spectrometry-Based Proteomics: Clickable Cross-Linkers for Elucidation of Protein Structures and Interactions; Anal Chem. 2012, vol. 84, No. 6, pp. 2662-2669.
Star-Weinstock et al., LC-ESI-MS/MS Analysis of Testosterone at Sub-Picogram Levels Using a Novel Derivatization Reagent; Analytical Chemistry, 2012, vol. 84, pp. 9310-9317.
Tretyakova et al., Quantitation of DNA adducts by stable isotope dilution mass spectrometry; Chem Res Toxicol, 2012, vol. 25, No. 10, pp. 2007-2035.
Wang et al.,. Cationic Xylene Tag for Increasing Sensitivity in Mass Spectrometry; American Society for Mass Spectrometry, 2015, vol. 26, pp. 1713-1721.
Ban et al., Tyrosine Bioconjugation through Aqueous Ene-Type Reactions: A Click-Like Reaction for Tyrosine; JACS Communications; 2010, 3-pages.
Cao et al., Collisionally Activagted Dissociation of Protonated 2-Deoxycytidine, 2-Deoxyuridine, and their Oxidatively Damaged Derivatives; Focus: Nucleic Acids in Mass Sepctrometry; 2006, 7-pages.
Chen et al., Selective chemical labeling of proteins; Organic & Biomolecular Chemistry; 2016, vol. 14, pp. 5417-5439.
Cheng et al., 8-Hydroxyguanie, an Abundant Form of Oxidative DNA Damage, Causes G-T and A-C Substitutions: The Journal of Biological Chemistry; 1992, vol. 267, No. 1, 7-pages.
Cortellino et al., Thymine DNA Glycosylase Is Essential for Active DNA Demethylation by Linked Deamination-Based Excision Repari; 2011; Cell; vol. 146, No. 1, pp. 67-79.
Cortazar et al., Embryonic lethal phenotype reveals a function of TDG in maintaining epigenetic stability; Nature; 2011, vol. 470, 8-pages.
He et al., Tet-Mediated Formation of 5-Carboxylcytosine and Its Excision by TDG in Mammalian DNA; Science; 2011, vol. 333, No. 6047, pp. 1303-1307.
Hill et al., Stimulation of human 8-oxoguanine-DNA glycosylase by AP-endonuclease: potential coordination of the initial steps in base excision repair; Nucleic Acids Research, 2001, vol. 29, No. 2, pp. 430-438.
Ito et al., Tet Proteins Can Convert 5-Methylcytosine to 5-Formylcytosine and 5-Carboxylcytosine; Science, 2011, vol. 333, 5-pages.
Jacobs A.L., DNA glycosylases: in DNA repair and beyond; Chromosoma, 2012, vol. 121, pp. 1-20.
Kalia et al., Hydrolytic Stability of Hydrazones and Oximes; Angew Chem Int. Ed. Engl.; 2008, vol. 47, No. 39, pp. 7523-7526.
Kim et al., Overview of Base Excision Repair Biochemistry; Curr Mo., Pharmacol. 2012, vol. 5, No. 1, pp. 3-13.
Krokan et al., Uracil in DNA—occurrence, consequences and repaid 2002, Onogene; vol. 21, pp. 8935-8948.
Krokan et al., Base Excision Repair; Cold Spring Harbor Perspectives In Biology; 2013, 24-pages.
Maiti et al., Thymine DNA Glycosylase Can Rapidly Excise 5-Formylcytosine and 5-Carboxylcytosine Potential Implications for Active Demethylation of CpG Sites; Nature, 2011, vol. 286, No. 41, 6-pages.
Morgan et al., Activation-induced Cytidine Deaminase Deaminates 5-Methylcytosine in DNA and Is Expressed in Pluripotent Tissues; The Journal of Biological Chemistry, 2004; vol. 279, No. 50, pp. 52353-52360.
Nilsen et al., Excision of deaminated cytosine from the vertebrate genome: role of the SMUG1 uracil-DNA glycosylase; The EMBO Journal; vol. 20, No. 15, pp. 4278-4286, 2001.
Schomacher et al., Neil DNA glycosylases promote substrate turnover by Tdg during DNA demethylation; Europe PMC Funders Group; 2016, Nat. Struct Mol Biol. vol. 23, No. 2, pp. 116-124.
Spruijt et al., Dynamic Readers For 5-(Hydorxy)Methylcytosine and Its Oxidized Derivatives; Cell; vol. 152, pp. 1148-1159.
Tsumura et al., Maintenance of self-renewal ability of mouse embryonic stem cells in the absence of DNA methyltransferases Dnmt1, Dnmt3a and Dnmt3b; Genes to Cells, 2006, vol. 11, pp. 805-814.
Visnes et al., Uracil in DNA and its processing by different DNA glycosylases; Phil. Trans. R. Soc. B, 2009, vol. 364, pp. 563-568.
Wang et al., Quantification of Oxidative DNA Lesions in Tissues of Long-Evans Cinnamon Rats by Capillary Hight-performance Liquid Chromatography-Tandem Mass Spectrometry Coupled with Stable Isotope-dilution Method; Anal Chem., 2011, vol. 83, No. 6, pp. 2001-2209.

Figures 3A - 3C
Figure 3A
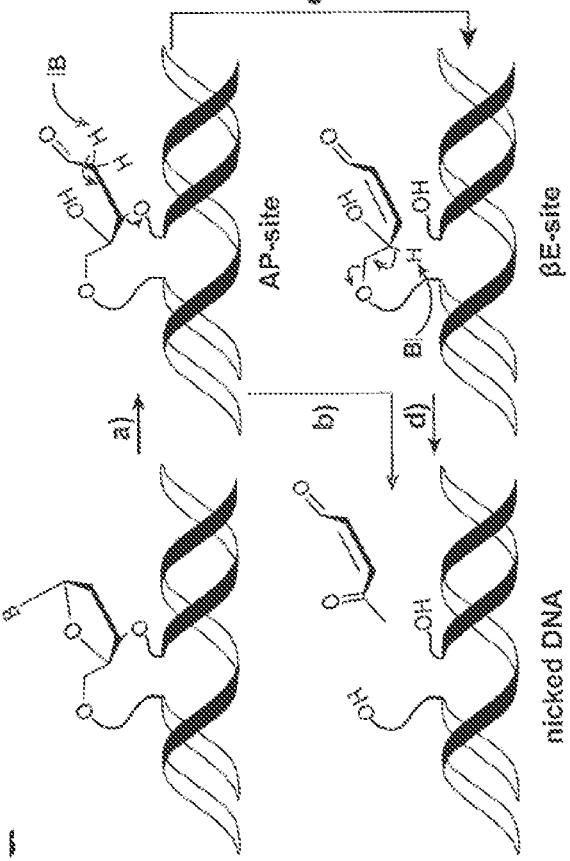
Figure 3B
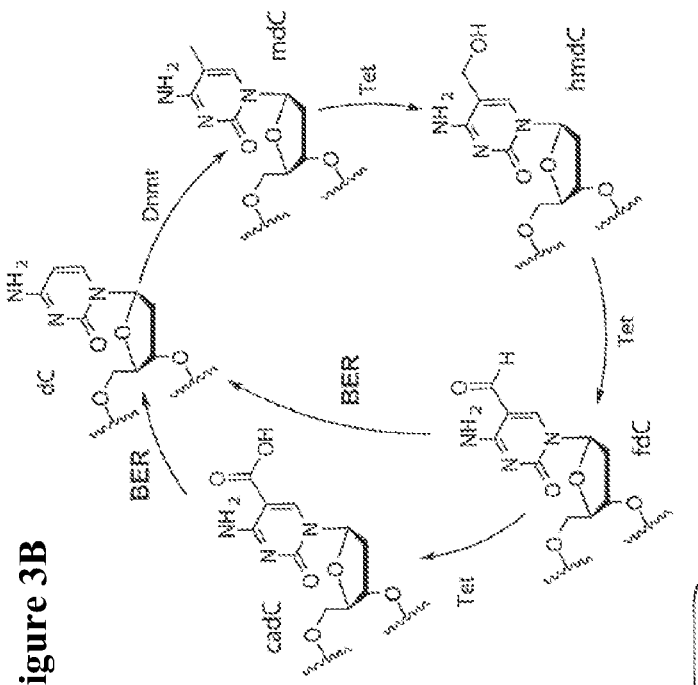
Figure 3C
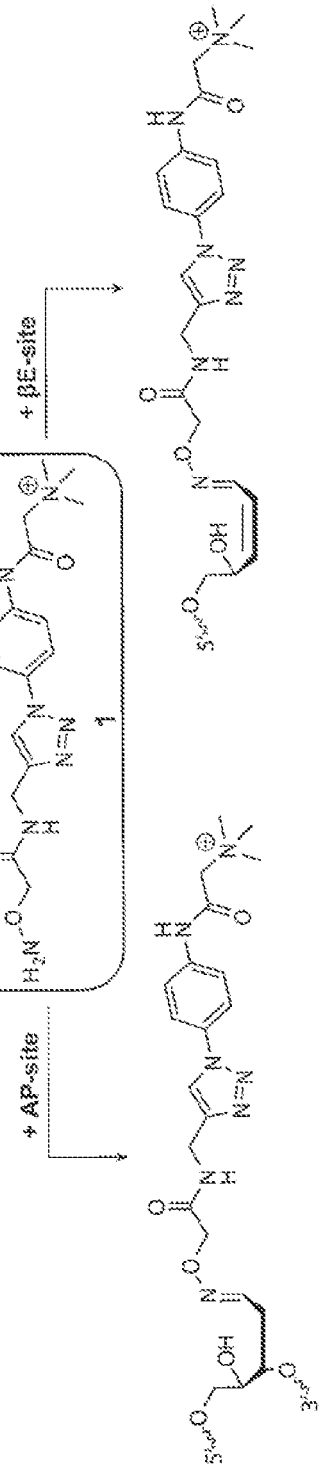

REAGENT FOR MASS SPECTROMETRY

CROSS-REFERENCE TO RELATED APPLICATION

The present invention claims priority to International Patent Application No. PCT/EP2018/052451, filed Jan. 31, 2018, which claims priority to EP Patent Application No. 17153895.2, filed Jan. 31, 2017, both of which are hereby incorporated by reference in their entireties.

DESCRIPTION

The present invention relates to reagents suitable in the mass spectrometric determination of analyte molecules such as carbohydrates as well as adducts of such reagents and analyte molecules and applications of said reagents and adducts. Further, the present invention relates to methods for the mass spectrometric determination of analyte molecules.

In the last decade, biological and medical research has focussed on the role and function of carbohydrates in living cells or organisms. Carbohydrates may be attached to proteins, lipids or other organic molecules, whereby characteristic complex glycosylation patterns are provided. Recently, it has been observed that certain disorders are associated with, accompanied by or caused by alterations in the glycosylation pattern. Particularly tumor disorders are frequently associated with altered glycosylation of various proteins.

Carbohydrates can be analysed using a variety of techniques including chromatographic separation techniques such as high performance liquid chromatography (HPLC) or capillary electrophoresis, or mass spectrometry (MS).

MS is a widely used technique for the qualitative and quantitative analysis of chemical substances ranging from small molecules to macromolecules. In general, it is a very sensitive and specific method, allowing even the analysis of complex biological, e.g. environmental or clinical samples.

For the analysis of mono-, oligo- or polysaccharides, MS has been combined with chromatographic techniques, particularly gas and liquid chromatography such as HPLC. Hereby, carbohydrate molecules are separated by chromatographic procedures and then individually subjected to mass spectrometric analysis. Since carbohydrates frequently occur in isobaric (regio- and/or stereoisomeric) structures, a chromatographic separation is not always possible. Thus, MS has also been used in combination with an ion mobility unit which allows separation of isobaric carbohydrates.

There is, however, still a need of increasing the sensitivity of MS analysis methods, particularly for the analysis of carbohydrates that have a low abundance or when only little materials (such as biopsy tissues) are available, by MS.

MS is not quantitative because the signal intensity reflects ionization properties and is strongly influenced by contaminants by processes called ion suppression. In consequence, there is a need for making the MS analysis quantitative.

The present invention relates to a novel reagent for use in MS which allows an extremely sensitive determination of analyte molecules such as carbohydrates in biological samples. Further, the use of isotopically modified versions of the reagents allows to obtain accurate quantitative MS data for comparative studies. The reagent has been successfully used for the direct, super sensitive, and quantitative analysis of glycostructures in the genome. Rare abasic sites (AP sites) and β-elimination products (βE-sites) generated by base excision repair were determined as target molecules. It was found that the reagent has an extremely high sensitivity.

SUMMARY OF THE INVENTION

Thus, a first aspect of the present invention is the use of a compound of general formula (I)

$$X\text{-}L_1\text{-}Y(\text{-}L_2\text{-}Z)_r \quad (I)$$

wherein
X is a reactive group capable of reacting with an analyte molecule, whereby a covalent bond with the analyte molecule is formed,
$L_1$ is a bond or a spacer,
Y is a neutral ion loss unit which, under conditions of mass spectrometry, is capable of fragmentation, whereby a neutral species, particularly a low-molecular weight neutral species, is released,
$L_2$ is a bond or a spacer,
Z is a charge unit comprising at least one charged moiety, in particular a permanently charged moiety,
r is 0 or 1,
including any salt thereof,
or a composition or kit comprising at least one compound (I) for the mass spectrometric determination of an analyte molecule.

In a particular aspect, compound (I) may be present as an isotopologue, i.e. a compound wherein one or more main isotopes herein also referred to as isotopically neutral atoms of the compound, e.g. $^1H$, $^{12}C$, $^{14}N$ and/or $^{16}O$ atoms have been replaced by minor stable isotopes, i.e. stable isotopes such as D, $^{13}C$, $^{15}N$ and $^{18}O$.

A further aspect of the invention is a method for the mass spectrometric determination of an analyte molecule in a sample comprising the steps:
(a) covalently reacting the analyte molecule with a compound of formula (I) as defined herein, whereby a covalent adduct of the analyte molecule and the compound (I) is formed, and
(b) subjecting the adduct from step (a) to a mass spectrometric analysis.

Still a further aspect of the invention is a compound which is of the general formula (Ia):

$$X\text{-}L_1\text{-}Y\text{-}L_2\text{-}Z \quad (Ia)$$

wherein
X is a carbonyl reactive group, dienophilic group, a carboxylate reactive group, a phenol reactive group, an amino reactive group, a hydroxyl reactive group, or a thiol reactive group, under the provision that X is no acrylester,
$L_1$ is a bond or a spacer,
Y is a neutral ion loss unit which, under conditions of mass spectrometry, is capable of fragmentation, whereby a neutral species, particularly a low-molecular weight neutral species, is released,
$L_2$ is a bond or a spacer,
Z is a charge unit comprising at least one permanently positively charged moiety,
including any salt thereof, or a composition or kit comprising at least one compound (Ia).

In a further aspect, the invention relates to a compound of formula (Ia), $$X\text{-}L_1\text{-}Y\text{-}L_2\text{-}Z \quad (Ia)$$

wherein
X is a carbonyl reactive group, dienophilic group, a carboxylate reactive group, a phenol reactive group, an amino reactive group, or a hydroxyl reactive group, $L_1$ is a bond or a spacer,
Y is a neutral ion loss unit which, under conditions of mass spectrometry, is capable of fragmentation, whereby a neutral species, particularly a low-molecular weight neutral species is released,
$L_2$ is a bond or a spacer,
Z is a charge unit comprising at least one negatively charged moiety, including any salt thereof, or a composition or kit comprising at least one compound (Ia).

The invention also relates to a reagent composition or reagent kit comprising at least one compound (Ia) and particularly a plurality of isotopically different species of compound (Ia).

According to a further aspect of the present invention, a covalent adduct of the compound of formula (I) and the analyte molecule, particularly an analyte molecule comprising a carbohydrate moiety may be used for the mass spectrometric determination. The adduct may be generated by reacting the analyte molecule present in a sample with compound (I). The adduct, however, may also be provided as a pure substance for use as a calibrator and/or standard.

Still a further aspect of the invention is a covalent adduct formed by reaction of compound (I) and an analyte molecule. The adduct may be a compound of the general formula (II):

$$T\text{-}X'\text{-}L_1\text{-}Y(\text{-}L_2\text{-}Z)_r \qquad (II)$$

wherein
T is an analyte molecule,
X' is a moiety resulting from the reaction of a reactive group X on compound (I) with an analyte molecule
X is a reactive group capable of reacting with an analyte molecule, whereby a covalent bond with the analyte molecule is formed,
$L_1$ is a bond or a spacer,
Y is a neutral ion loss unit which, under conditions of mass spectrometry, is capable of fragmentation, whereby a neutral species, particularly a low-molecular weight neutral species is released,
$L_2$ is a bond or a spacer,
Z is a charge unit comprising at least one charged moiety,
r is 0 or 1,
including any salt thereof.

A particular embodiment is a covalent adduct formed by reaction of compound (Ia) and an analyte molecule is represented by formula (IIa):

$$T\text{-}X'\text{-}L_1\text{-}Y\text{-}L_2\text{-}Z \qquad (IIa)$$

wherein
T is an analyte molecule,
X' is a moiety resulting from the reaction of a reactive group X on compound (Ia) with an analyte molecule
X is a reactive group capable of reacting with an analyte molecule, whereby a covalent bond with the analyte molecule is formed,
$L_1$ is a bond or a spacer,
Y is a neutral ion loss unit which, under conditions of mass spectrometry, is capable of fragmentation, whereby a neutral species, particularly a low-molecular weight neutral species is released,
$L_2$ is a bond or a spacer, and
Z is a charge unit comprising at least one charged moiety, including any salt thereof.

EMBODIMENTS

The present invention relates to the determination of an analyte molecule by MS. The analyte molecule may be any substance capable of forming a covalent bond with a reactive group X on the compound (I) of the present invention. For example, the analyte may be a biomolecule selected from carbohydrates including modified carbohydrates, e.g. carbohydrates with amino, N-acetyl, sulphate and/or carboxylate groups as well as deoxy- or methyl-modified carbohydrates, amino acids, peptides, proteins, fatty acids, lipids, steroids, ketosteroids, secosteroids, nucleosides, nucleotides, nucleic acids and other biomolecules including small molecule metabolites and cofactors as well as drugs, agricultural agents, toxins or metabolites thereof. Such analyte molecules may be present in biological, clinical or environmental samples such as body liquids, e.g. blood, serum, plasma, urine, saliva, spinal fluid, etc., tissue or cell extracts, etc. In some embodiments, the analyte molecules may be present in a sample which is a purified or partially purified sample, e.g. a purified or partially purified protein mixture or extract.

According to the present invention, analyte molecules selected from carbohydrates, and compounds containing phenolic groups and keto groups like steroids such as testosterone and estradiol, ketosteroids and secosteroids such as vitamin D are of particular relevance and can be determined using the reagents described herein.

The analyte molecule may be derivatized at different stages within the sample preparation workflow. In the context of the present disclosure, the term "derivatized" or "derivatization" refers to the reaction of an analyte with a chemical compound such as the compound of formula (I) of the present invention. Accordingly, the term "derivatization reagent" refers to the compound which is used to derivatize the analyte. The analyte molecule may be derivatized subsequent to the pre-treatment of the sample, subsequent to a first enrichment of the sample, or subsequent to a second enrichment of the sample.

The samples comprising an analyte molecule may be pre-treated and/or enriched by various methods. The pre-treatment method is dependent upon the type of sample, such as blood (fresh or dried), plasma, serum, cerebrospinal fluid (CSF), tissue, urine, or saliva.

In particular, in case the sample is a whole blood sample, it is assigned to one of two pre-defined sample pre-treatment (PT) workflows, both comprising the addition of an internal standard (IS) and a hemolysis reagent (HR) followed by a pre-defined incubation period (Inc), where the difference between the two workflows is the order in which the internal standard (IS) and a hemolysis reagent (HR) are added. In an additional step a derivatization reagent such as compounds of the present invention as disclosed herein above or below, is added followed by an incubation period. An internal standard (IS) is typically a known amount of the same analyte(s) of interest that may be for example isotopically labeled. This allows relative comparison, and may enable unambiguous identification and quantification of the analyte(s) of interest present in the sample when the analyte(s) reach the mass spectrometer.

In case the sample is a urine sample, it is assigned to one of other two pre-defined sample PT workflows, both comprising the addition of an internal standard (IS) and an enzymatic reagent (E) followed by a pre-defined incubation period (Inc), where the difference between the two workflows is the order in which the internal standard (IS) and a enzymatic reagent (HR) are added. An enzymatic reagent is typically a reagent used for glucuronide cleavage or protein cleavage or any pre-processing of analyte or matrix. In an additional step a derivatization reagent such as compounds of the present invention as disclosed herein above or below, is added followed by an incubation period.

If the sample is plasma or serum it is assigned to another pre-defined PT workflow including only the addition of an internal standard (IS) followed by a pre-defined incubation time (Inc). In an additional step the derivatization reagent such as compounds of the present invention as disclosed herein above or below, is added followed by an incubation period.

Such a pre-treated sample may be further subjected to an analyte enrichment workflow.

In particular, the analyte enrichment workflow may comprises addition of magnetic beads (MB) carrying analyte-selective groups, and optionally a bead binder, to the pre-treated sample followed by a pre-defined incubation period (Inc) for capturing the analyte(s) of interest, where the addition of the magnetic beads (MB) may include agitation or mixing. After incubation with the magnetic beads (MB) the workflow may comprise a washing step (W1) and depending on the analyte(s) possibly one or more additional washing steps (W2). A washing step (W1, W2) comprises a series of steps including magnetic bead separation (B sep) by a magnetic bead handling unit comprising magnets or electromagnets, aspiration of liquid (Asp.), addition of a washing buffer (W. Buffer), resuspension of the magnetic beads (Res.), another magnetic bead separation step (B Sep) and another aspiration of the liquid (Asp.). Moreover washing steps may differ in terms of type of solvent (water/organic/salt/pH), apart from volume and number or combination of washing cycles.

The last washing step (W1, W2) is followed by the addition of an elution reagent (ER) followed by resuspension (Res.) of the magnetic beads and a pre-defined incubation period (Inc.) for releasing the analyte(s) of interest from the magnetic beads. The bound-free magnetic beads are then separated (B Sep.) and the supernatant containing derivatized analyte(s) of interest is directly transferred to the LC station or is transferred to the LC station after a dilution step by addition of a dilution liquid (Dil.). Different elution procedures/reagents may also be used, by changing e.g. the type of solvents (water/organic/salt/pH) and volume.

In case, the derivatisation of the analyte of interest did not take place after the pre-treatment method, derivatization of the analytes in the sample may take place after the first enrichment workflow using magnetic beads. Herein, a derivatization reagent such as compounds of the present invention as disclosed herein above or below, is added to the sample of interest after the washing steps (W1, W2) are concluded either prior to, together with or subsequent with the elution reagent, which is followed by an incubation period (defined time and temperature). The bound-free magnetic beads are then separated (B Sep.) and the supernatant containing the derivatized analyte(s) of interest is directly transferred to the LC station or after a dilution step by addition of a dilution liquid (Dil.). Different elution procedures/reagents may also be used, by changing e.g. the type of solvents (water/organic/salt/pH) and volume.

A further option covers derivatization of the analytes after a second analyte enrichment workflow including chromatographic-separation (including but not limited to liquid chromatography or gas chromatography), in particular liquid chromatography, using post column infusion of the derivatization reagent such as compounds of the present invention as disclosed herein above or below.

In particular embodiments, the analyte molecule is a carbohydrate or substance having a carbohydrate moiety, e.g. a glycoprotein or a nucleoside. For example, the analyte molecule may be a monosaccharide such as ribose, desoxyribose, arabinose, ribulose, glucose, mannose, galactose, fucose, fructose, N-acetylglucosamine, N-acetylgalactosamine, neuraminic acid, N-acetylneurominic acid, etc., or an oligosaccharide, e.g. a disaccharide such as sucrose, maltose or lactose or a tri- or tetrasaccharide as well as a polysaccharide, or substance comprising such a mono-, oligo- or polysaccharide moiety.

Preferably, the analyte molecule comprises a carbonyl group, e.g. an aldehyde or a keto group, or a masked aldehyde or keto group, e.g. a hemiacetal group, particularly a cyclic hemiacetal group, which is capable of forming a covalent bond with reactive group X of compound (I). The analyte molecule may also comprise an acetal group, which can be converted into an aldehyde, keto or hemiacetal group before reaction with the compound (I).

In other embodiments, the analyte molecule may comprise a group selected from amino, thiol, hydroxy, vicinal diol, conjugated diene, phenol, nucleobase, carboxyl, terminal cysteine, and terminal serine, which is capable of forming a covalent bond with reactive group X of compound (I). Further, it is also contemplated within the scope of the present invention that a group present on an analyte molecule would be first converted into another group that is more readily available for reaction with reactive group X of compound (I).

Analytes containing one or more phenolic groups are of particular interest. By way of example, the analyte may be selected from steroids, steroid-like compounds, estrogen, estrogen-like compounds, estrone (EI), estradiol (E2), 17a-estradiol, 17p-estradiol, estriol (E3), 16-epiestriol, 17-epiestriol, and 16, 17-epiestriol, and/or metabolites thereof. In various embodiments, the metabolites can be, for example, estriol, 16-epiestriol (16-epiE3), 17-epiestriol (17-epiE3), 16,17-epiestriol (16,17-epiE3), 16-ketoestradiol (16-ketoE2), 16a-hydroxyestrone (16a-OHEI), 2-methoxyestrone (2-MeOEI), 4-methoxyestrone (4-MeOEI), 2-hydroxyestrone-3-methyl ether (3-MeOEI), 2-methoxyestradiol (2-MeOE2), 4-methoxyestradiol (4-MeOE2), 2-hydroxyestrone (2OHE1), 4-hydroxyestrone (4-OHE1), 2-hydroxyestradiol (2-OHE2), estrone (EI), estrone sulfate (EIs), 17a-estradiol (E2a), 17p-estradiol (E2b), estradiol sulfate (E2s), equilin (EQ), 17a-dihydroequilin (EQa), 17p-dihydroequilin (EQb), Eqilenin (EN), 17-dihydroequilenin (ENa) 17β-dihydroequilenin (ENb), A8,9-dehydroestrone (dEI), A8,9-dehydroestrone sulfate (dEIs). In some embodiments, the phenolic analyte can be a steroid or a steroid-like compound having an A-ring which is sp$^2$ hybridized and an OH group at the 3-position of the A-ring.

Analytes containing one or more keto groups are of further interest. Preferred examples are ketosteroids including but not limited to DHT, testosterone, epitestosterone, desoxymethyltestosterone (DMT), tetrahydrogestrinone (THG), aldosterone, estrone, 4-hydroxyestrone, 2-methoxyestrone, 2-hydroxyestrone, 16-ketoestradiol, 16 alpha-hydroxyestrone, 2-hydroxyestrone-3-methylether, prednisone, prednisolone, pregnenolone, progesterone, DHEA (dehydroepiandrosterone), 17 OH pregnenolone, 17 OH progesterone, 17 OH progesterone, androsterone, epiandrosterone, and delta 4 androstenedione) 11-desoxycortisol corticosterone, 21 deoxycortisol, 11 deoxycorticosterone, allopregnanolone, and aldosterone.

To facilitate and improve the MS measurement of analytes, the present invention relates in a first aspect to the use of a compound of general formula (I):

$$X\text{-}L_1\text{-}Y(\text{-}L_2\text{-}Z)_r \qquad (I)$$

wherein

X is a reactive group capable of reacting with an analyte molecule, whereby a covalent bond with the analyte molecule is formed, $L_1$ is a bond or a spacer, Y is a neutral ion loss unit which, under conditions of mass spectrometry, is capable of fragmentation, whereby a neutral species, particularly a low-molecular weight neutral species is released, $L_2$ is a bond or a spacer, Z is a charge unit comprising at least one charged moiety, in particular a permanently charged moiety, r is 0 or 1, including any salt thereof, or a composition or kit comprising at least one compound (I) for the mass spectrometric determination of an analyte molecule.

Compound (I) for use in MS according to the present invention comprises a reactive group X capable of reacting with an analyte molecule, whereby a covalent bond with the analyte molecule is formed.

In embodiments, the reactive group X of compound (I) may be selected to react with different functional groups on an analyte molecule. It is within common knowledge to decide which reactive groups X will qualify for binding to a functional group of an analyte of interest. Functional groups on an analyte molecule are vicinal diols, phenol groups, nucleobases, amino, mercapto, hydroxy, 1-hydroxy 2-amino alkyl, 1-amino 2-mercapto alkyl, keto, 1,3-dienyl, enyl, allyl, formyl, and carboxylate groups. Reactive groups are summarized in standard text books "Bioconjugate Techniques" 3rd edition: https://doi.org/10.1016/B978-0-12-382239-0.00025-X; and "The Molecular Probes Handbook: A Guide to Fluorescent Probes and Labeling Technologies", 11th Edition ed Iain D. Johnson, Life Technologies Corporation, 2010; and review articles (e.g. X. Chen et al., Org. Biomol. Chem., 2016, 14, 5417-5439; and T. Higashi J Steroid Biochem Mol Biol. 2016 September; 162:57-69).

In particular, the reactive group X is a carbonyl-reactive group, a dienophilic group, a carboxylate reactive group, a phenol reactive group, an amino reactive group, a hydroxyl reactive group, or a thiol reactive group. In particular, the reactive group X is selected from the group consisting of an amine reactive group, a thiol reactive group, a carbonyl reactive group, a dienophilic group, a 1,2 diol reactive group, a carboxylate reactive group, a hydroxyl reactive group, a 1-amino 2-hydroxy alkyl reactive group, an 1-amino 2-mercapto reactive group, and a group reacting at the ortho positions of phenols.

In a preferred embodiment, group X is a carbonyl-reactive group, which is capable of reacting with any type of molecule, e.g. carbohydrate molecule, having a carbonyl group. In particular, the carbohydrate-reactive group X of compound (I) is capable of reacting with all types of sugars including aldoses, such as glucose, mannose, galactose, ribose or fucose, and ketoses such as ribulose or fructose as well as with oligosaccharides such as di-, tri- or tetrasaccharides and polysaccharides having an accessible aldehyde or keto group or a hemiacetal masked aldehyde or keto group. The carbonyl-reactive group may have either a supernucleophilic N atom strengthened by the α-effect through an adjacent O or N atom $NH_2$—N/O or a dithiol molecule. It may be selected from:

(i) a hydrazine group, e.g. a $H_2N$—NH—, or $H_2N$—$NR^1$— group, wherein $R^1$ is aryl, or $C_{1-4}$ alkyl, particularly $C_1$ or $C_2$ alkyl, optionally substituted e.g. with halo, hydroxyl, and/or $C_{1-3}$ alkoxy, (ii) a hydrazone group, e.g. a $H_2N$—NH—C(O)—, or $H_2N$—$NR^2$—C(O)— group, wherein $R^2$ is aryl or $C_{1-4}$ alkyl, particularly $C_1$ or $C_2$ alkyl, optionally substituted e.g. with halo, hydroxyl, and/or $C_1$-3 alkoxy, (iii) a hydroxylamino group, e.g. a $H_2N$—O— group, and (iv) a dithiol group, particularly a 1,2-dithiol or 1,3-dithiol group.

In a preferred embodiment, reactive group X is a keto reactive group, which is capable of reacting with an analyte comprising a keto group e.g. ketosteroids like DHT, testosterone, epitestosterone, desoxymethyl testosterone (DMT), tetrahydrogestrinone (THG), aldosterone, estrone, 4-hydroxyestrone, 2-methoxyestrone, 2-hydroxyestrone, 16-ketoestradiol, 16 alpha-hydroxyestrone, 2-hydroxyestrone-3-methylether, prednisone, prednisolone, pregnenolone, progesterone, DHEA (dehydroepiandrosterone), 17 OH pregnenolone, 17 OH progesterone, 17 OH progesterone, androsterone, epiandrosterone, and delta 4 androstenedione) 11-desoxycortisol corticosterone, 21 deoxycortisol, 11 deoxycorticosterone, allopregnanolone, and aldosterone.

For example, a reactive haloacetyl group as Br/I—$CH_2$—C(O)—, an acrylamide/ester group, an imide such as maleimide or methylsulfonyl phenyloxadiazole may react with nucleophilic groups such as thiol groups on an analyte molecule. An amino-reactive group, e.g. an active ester group such as N-hydroxy succinimide (NHS) ester or sulfo-NHS ester, pentafluoro phenyl ester, quadratic acid esters, a hydroxybenzotriazole (HOBt) ester, or 1-hydroxy-7-azabenzotriazole (HOAt) ester or a sulfonylchloride group may react with amino groups on an analyte molecule. A hydrazine or hydroxyl amino group as described above may also be used to react with other electrophilic groups present on an analyte molecule.

For binding to diols, the reactive group X may comprise boronic acid. Alternatively, diols can be oxidised to the respective ketones or aldehydes and then reacted with ketone/aldehyde-reactive groups X. Dienophils as triazol dione can be selected as the reactive group X for binding to dienes. Phenol groups present on an analyte molecule can be reacted with triazole dione via en reaction (H. Ban et al *J. Am. Chem. Soc.*, 2010, 132 (5), pp 1523-1525) or by diazotization or alternatively by ortho nitration followed by reduction to an amine which could then be reacted with an amine reactive reagent.

Nucleobases can be reacted with 2-chloro acetyl or Pt complexes as the reactive group X. Terminal cysteines can be reacted with heteroaryl/aryl cyanides as the reactive group X. Terminal serines can be oxidized to yield aldehyde groups and the reacted with known aldehyde-reactive groups X.

Depending on the functional groups present on an analyte molecule to be determined, the skilled person will select an appropriate reactive group X for compound (I).

In a further embodiment, the reactive group is a carboxylate reactive group e.g. diazo compound (Chromatographia 2012, 75, 875-881) which can be used for derivatization of prostaglandins. Other well-known carboxylate reactive groups are alkylhalides. Well known is also the activation of the carboxylic acid followed by reaction wth an nucleophile like an amine or hydrazine (A. Kretschmner et al Journal of Chromatography B Volume 879, 17-18, May 2011, Pages 1393-1401).

Hydroxyl reactive groups are (T. Higashi J Steroid Biochem Mol Biol. 2016 September; 162:57-69) sulfonylchlorides, activated carboxylic esters (NHS, or imidazolide), and fluoro aromates/heteroaromates capable for nucleophilic substitution of the fluorine.

In a preferred embodiment, reactive group X is a phenol-reactive group, which is capable of reacting with any type of molecule having a phenol group, e.g. steroids, steroid-like compounds, estrogen, estrogen-like compounds, estrone (E1), estradiol (E2), 17a-estradiol, 17p-estradiol, estriol (E3), 16-epiestriol, 17-epiestriol, and 16, 17-epiestriol, and/or metabolites thereof. By way of example, the phenol-reactive group may be a 1,2,4-triazolin-3,5-dione group, 1,2,4-triazolin-3,5-diones are also capable to act as a dienophile and are therefore useful for detection of vitamin D $1\alpha,25(OH)_2VitD_3$, $1\alpha,25(OH)_2VitD_2$, $25(OH)VitD_2$, $25(OH)VitD_3$ and $24R,25(OH)_2VitD_3$.

The compound (I) further comprises a neutral ion loss unit Y. In the context of the present application, the term "neutral ion loss unit" refers to a unit, which is able to lose a moiety having no charge. Said moiety includes, but is not limited to ions, atoms and a plurality of atoms. The unit Y is neutral, i.e. it does not carry a positive or negative charge and it is linked to the reactive group X via a linker $L_1$ as defined herein below. The neutral unit Y is, under conditions of MS, e.g. when subjected to collision-induced dissociation (CID), for example in triple quadrupole MS, capable of fragmentation, whereby a neutral species is released. After release of the first neutral species, the remainder of unit Y still remains neutral. Typically, but not necessarily, one neutral species is released, i.e. a first neutral species is released. In particular embodiments, two neutral species are released.

The first neutral species may be a low molecular weight neutral species, e.g. a neutral molecule having a molecular weight of 100 or less, more particularly of 80 or less. Further, the first neutral species may be an inorganic molecule such as SO, $SO_2$, CO, $CO_2$, NO, $NO_2$ or $N_2$. In particular, the neutral species is $N_2$ or $SO_2$. More particularly, the first neutral species is $N_2$. The reaction that leads to the loss of the neutral molecule may be preferentially a cycloreversion reaction, in particular a 1,3-dipolar cycloreversion. In the context of the present disclosure, the term "cycloreversion" refers to the reversal of any cycloaddition reaction.

In particular embodiments, the neutral ion loss unit Y comprises or consists of a cyclic moiety (e.g. cyclic ketones like bicyclo[2.2.1]heptadien-7-one are known to lose CO), particularly a heterocyclic moiety, more particularly a 6-, 5-, or 4-membered heterocyclic moiety, which is capable of fragmentation, whereby the first neutral species as described above is released. Such (hetero)cyclic groups readily show fragmentation by means of a retro (hetero)cycloaddition reaction, whereby the neutral species is released.

Preferably, the neutral ion loss unit Y comprises or consists of a 5- or 6-membered heterocyclic moiety having at least two hetero atoms, such as N, O and/or S atoms, particularly N atoms, adjacent to each other, e.g. in 1,2-position, such as cyclic azo compounds and 5-membered rings selected form triazole, in particular 1,2,3-triazole, tetrazole, tetrazine, 1,2,3 oxa- or thia-diazole, or hydrogenated derivatives thereof. To the above mentioned heterocycles a further ring can be annealed e.g. benzothiadiazol, or benzotriazol. Heterocycles can be partially hydrogenated e.g. 2,5 dihydro pyrrol, and 2,5 dihydrothiophen 1,1 dioxide.

In an especially preferred embodiment, the 5-membered heterocyclic moiety is a triazole moiety, which may be synthesized via a cycloaddition or click reaction of an alkyne and an azide possibly but not necessarily in the presence of Cu (I) as a catalyst. Under conditions of MS, fragmentation of a triazole moiety causes a release of $N_2$ via a 1,3 dipolar cycloreversion reaction leading to a reduction of the mass/charge ratio (m/z) of 28 in the mass spectrometer.

The skilled person is well aware that neutral ion loss units may be identified using commercially available software, e.g. ACD/MS Fragmenter (ACD Labs). Further reactions and species which lead to neutral losses are described in the following references:

Carey, Sundberg: Organische Chemie, Ein weiterführendes Lehrbuch Korrigierter Nachdruck VCH 1995; ISBN: 3-527-29217-9; and Fred W. McLafferty, Frantisek Turecek, Interpretation von Massenspektren Springer Spektrum 1995, Softcover: ISBN978-3-642-39848-3).

In particular embodiments, but not necessarily, the compound (I) has a charge unit Z comprising at least one charged moiety, i.e. a moiety which is predominantly present in a charged state under substantially neutral conditions. For example, the charge unit Z comprises (i) at least one positively charged moiety such as a primary, secondary, tertiary or quaternary ammonium group or a phosphonium group, particularly having a $pK_a$ of 10 or higher, more particularly having a $pK_a$ of 12 or higher, or (ii) at least one negatively charged moiety such as a phosphate, sulphate, sulphonate or carboxylate group, particularly having a $pK_b$ of 10 or higher, more particularly having a $pK_b$ of 12 or higher.

In the context of the present application, the term "having a $pK_a$ of" refers to the fact that a charged moiety provides the overall molecule with a certain $pK_a$ value which differs from the $pK_a$ value of the molecule without the charged moiety. Exemplified, the term "at least one positively charged moiety having a $pK_a$ of 10 or higher" specifies that the overall molecule comprising said at least one positively charged moiety, exhibits a $pK_a$ of 10 or higher. The same also applies analogously to $pK_b$ values.

The charge unit Z most preferably consists of one charged moiety.

If a charge unit Z is present, it is linked to the neutral ion loss unit Y via a linker $L_2$ as defined herein. Accordingly, charge and ability to undergo a neutral loss are provided by different units. Even under conditions where the neutral ion loss unit Y is fragmented leading to a release of a (low molecular weight) neutral species, the charge unit Z remains unchanged. This means that the state of charge of the remaining residue does not change. If the compound was previously positively charged due to a positive charge in the charge unit Z, it remains positively charged even after release of the low molecular weight neutral species.

Preferably, the compound (I) has a charge unit Z comprising at least one positively charged moiety. Most preferably, the charge unit Z consists of one positively charged moiety and lacks any groups capable to undergo an alternative fragmentation.

The reagent compound (I) may have a charged moiety resulting from the presence of charge unit Z. The charge may be permanent, e.g. when using a quaternary ammonium group, or may be generated by protonation (positive charge) or deprotonation (negative charge). According to the invention, a permanent charge is preferred. The presence of a charged moiety in compound (I) is, preferred, however, not necessarily required. Preferred permanent positive charge units are tetralkylammonium, 1 alkyl pyridinium, and 1,3 dialkyl imidazolium units.

In addition to the release of the first neutral species, the compound (I) may be capable of an alternative fragmentation under conditions of mass spectrometry, e.g. via CID. Thereby a second neutral species different from the first neutral species is released. For example, the second neutral species may comprise an aryl-radical, e.g. a phenyl- or substituted phenyl-radical or a halogen radical (Cl, Br, I). The alternative fragmentation leading to release of a second neutral species preferably takes place only under conditions of higher energy than required for release of the first neutral species from neutral ion loss unit Y.

In particular embodiments, the compound exhibits the general formula (Ia)

X-$L_1$-Y-$L_2$-Z    (Ia)

wherein

X is a carbonyl reactive group, dienophilic group, a carboxylate reactive group, a phenol reactive group, an amino reactive group, a hydroxyl reactive group, or a thiol reactive group, and wherein X is no acrylester, $L_1$ is a bond or a spacer, Y is a neutral ion loss unit which, under conditions of mass spectrometry, is capable of fragmentation, whereby a neutral species, particularly a low-molecular weight neutral species, is released, $L_2$ is a bond or a spacer, Z is a charge unit comprising at least one permanently positively charged moiety, including any salt thereof.

In particular embodiments, the compound exhibits the general formula (Ia)

X-$L_1$-Y-$L_2$-Z    (Ia)

wherein

X is a carbonyl reactive group, dienophilic group, a carboxylate reactive group, a phenol reactive group, an amino reactive group, or a hydroxyl reactive group, $L_1$ is a bond or a spacer, Y is a neutral ion loss unit which, under conditions of mass spectrometry, is capable of fragmentation, whereby a neutral species, particularly a low-molecular weight neutral species, is released, $L_2$ is a bond or a spacer, Z is a charge unit comprising at least one negatively charged moiety, including any salt thereof, or a composition or kit comprising at least one compound (Ia).

In a preferred embodiment, the compound of formula (I) is suitable as a reagent for the determination of carbohydrates and ketosteroids and may be a compound of the general formula (Ib):

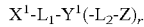

$X^1$-$L_1$-$Y^1$(-$L_2$-Z)$_r$ wherein $X^1$ is a carbonyl-reactive group as described above, $Y^1$ is a neutral ion loss unit comprising (i) a heterocyclic moiety which, under conditions of mass spectrometry, is capable of fragmentation, whereby a first neutral species is released, and (ii) optionally a moiety, which under conditions of mass spectrometry, is capable of an alternative fragmentation, whereby a second neutral species different from the first neutral species is released, $L_1$ is a bond or a spacer, $L_2$ is a bond or a spacer, Z is a charge unit comprising at least one charged moiety, in particular a permanently charged moiety, and r is 0 or 1.

Groups $L_1$ and $L_2$ in general formula (I), (Ia) or (Ib) independently represent a bond, i.e. a covalent bond, or a spacer, i.e. a linear or branched spacer having a chain length from 1 up to usually 4, 6, 8 or 10 atoms or even more, e.g. C-atoms optionally including at least one heteroatom. Preferably, groups $L_1$ and $L_2$ are short spacers, having a length of 1, 2 or 3 atoms and most preferably lacking any moieties which may be subject to alternative fragmentation. Further, it is preferred for the groups $L_1$ and $L_2$ not to include any stereocenters. In case stereoisomers are present, only one species of stereoisomer is present, but no mixture of two or more species of stereoisomers. For use in MS, compound (I) is preferably provided in stereoisomerically pure form.

In particular embodiments, $L_1$ or $L_2$ are independently of each other C1-C4 alkyl spacers, optionally comprising at least one heteroatom. In further embodiments, one of $L_1$ and $L_2$ includes an aryl group, such as a phenyl group, which may be subject to alternative fragmentation as described above.

In particular embodiments, the adduct formed by a reaction of the compound of the present invention with a given analyte exhibits only one mass transition when subjected to mass spectrometry measurement.

A specific example of a compound according to the present invention is a compound of formula (Ic):

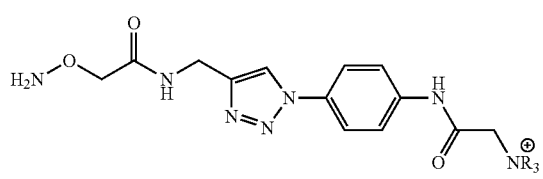

wherein R is in each case independently H or $C_{1-4}$ alkyl, particularly methyl, and A is an anion, e.g. formate.

A further embodiment of the present invention relates to a compound of formula (I) which is an isotopologue. The term "isotopologue" relates to a compound (I) wherein at least one of the main isotopes is replaced by a stable minor isotope of the respective element, having a molecular mass, which is different from the molecular mass of the respective main isotope. Thus, the resulting isotopologue of (I) has a molecular mass which is different from the molecular mass of the respective compound consisting of the main isotopes here referred to isotopically neutral. This difference in molecular mass allows mass spectrometric differentiation of an isotopically neutral compound and an isotopologue thereof. In a preferred embodiment, the isotopologue comprises at least one isotope selected from D (as replacement of H), $^{13}C$ (as replacement of $^{12}C$), $^{15}N$ (as replacement of $^{14}N$) and $^{18}O$ (as replacement of $^{16}O$).

In an isotopologue, one or more and up to all of the respective isotopically neutral atoms may be replaced by isotopes. Thereby, a great number of different isotopologues of a single compound may be provided.

For example, in a compound of formula (Ic) as shown above, one or more or all H, $^{14}N$ and $^{12}C$ atoms in the aromatic unit or in the glycine units may be replaced by D, $^{15}N$ or $^{13}C$. The N atoms at position 2 and 3 of the triazole ring will not be replaced by $^{15}N$ since they will be cleaved off as neutral species $N_2$.

In a specific embodiment of the compound of formula (Ic), wherein R=methyl, all three CH$_3$ groups are replaced by CD$_3$ groups. This isotopologue is nine mass units heavier and thus MS-distinguishable from the respective isotopically neutral compound with three CH$_3$ groups.

The compound (I) may be provided as an isotopically neutral compound or as an isotopologue which is MS-distinguishable from the respective isotopically neutral compound or as a composition comprising a plurality of different MS-distinguishable isotopologues of the same compound or as a kit comprising a plurality of different MS-distinguishable isotopologues of the same compound in separate form. Composition or kits comprising a plurality of different MS-distinguishable isotopologues of a reagent are particularly suitable for multiplexing applications as described below.

The synthesis of preferred compounds of formula (I) including isotopologues thereof is described below in the Examples section.

Still a further aspect of the invention relates to the use of the compound of formula (I) for the mass spectrometric determination of an analyte molecule, particularly for the determination of a carbohydrate analyte molecule as described above. This use involves a derivatization of the analyte molecule by means of a reaction with compound (I), whereby a covalent adduct is formed and subsequently subjected to analysis by MS.

A general scheme involving the use of compound (I) as a reagent for the determination of an analyte molecule by MS comprises the following steps:

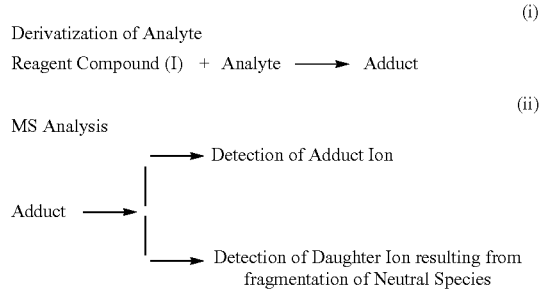

Fragmentation of a neutral species from the adduct ion, i.e. neutral ion loss does not change the overall charge. Thus, the daughter ion has the same charge as the molecule ion.

In case the adduct comprises a positive charge, MS detection occurs in the positive mode. In case the adduct has a negative charge, the detection will be performed in the negative MS mode.

Mass spectrometric determination may be combined by additional analytic methods including chromatographic methods such as gas chromatography (GC), liquid chromatography (LC), particularly HPLC, rapid LC, or micro LC (μLC), and/or ion mobility-based separation techniques.

A further aspect of the invention is the use of an adduct formed by reaction of the compound of general formula (I) as described above and an analyte molecule for the mass spectrometric determination of an analyte molecule. By means of this reaction, a covalent bond between compound (I) and the analyte molecule is formed. In a particular preferred embodiment, the mass spectrometric determination comprises tandem mass spectrometric determination, more particularly in a triple quadrupole device, wherein the molecule ion of the analyte adduct is subjected to fragmentation, e.g. by collision-induced dissociation (CID), and a daughter ion is generated from the molecule ion. By detecting the adduct molecule ion and the daughter ion in parallel, a highly sensitive determination of the analyte is possible.

In a preferred embodiment, the adduct used for the MS determination is a compound of the general formula (II):

$$T\text{-}X'\text{-}L_1\text{-}Y(\text{-}L_2\text{-}Z)_r \qquad (II)$$

wherein
T is an analyte molecule,
X' is a moiety resulting from the reaction of a reactive group X on compound (I) with an analyte molecule and L$^1$, Y, L$_2$, Z and r are as defined above.

The adduct compound of formula (II) carries a positive or negative charge which allows mass spectrometric detection. This charge may be provided by the charge unit Z of compound (I). The presence of a charge unit in compound (I) is preferred, however, is not necessary since a charge can be provided by other means, e.g. when the analyte molecule itself carries a charge and/or when the adduct can be provided with a charge by means of a protonation or deprotonation.

In one embodiment, the adduct compound (II) may be generated by reaction of an analyte molecule present in a sample to be analysed with compound (I) which has been added to the sample.

Still a further aspect of the invention is an adduct compound (IIa)

$$T\text{-}X'\text{-}L_1\text{-}Y\text{-}L_2\text{-}Z \qquad (IIa)$$

wherein
T, X', L$_1$, Y, L$_2$, and Z are as defined herein above, including any salt thereof, or a composition or kit comprising at least one adduct of formula (IIa).

In particular, the adduct is a compound of formula (IIa)

$$T\text{-}X'\text{-}L_1\text{-}Y\text{-}L_2\text{-}Z \qquad (IIa)$$

wherein
X' is a moiety resulting from the reaction of a reactive group X on compound (I), X is a carbonyl reactive group, a dienophilic group, a carboxylate reactive group, a phenol reactive group, an amino reactive group, a hydroxyl reactive group, or a thiol reactive group, under the provision that X is no acrylester,
L$_1$ is a bond or a spacer,
Y is a neutral ion loss unit which, under conditions of mass spectrometry, is capable of fragmentation, whereby a neutral species, particularly a low-molecular weight neutral species, is released,
L$_2$ is a bond or a spacer,
Z is a charge unit comprising at least one permanently positively charged moiety as defined above, preferably tetralkylammonium, 1 alkyl pyridinium, or 1,3 dialkyl imidazolium unit,
including any salt thereof, or a composition or kit comprising at least one adduct of formula (IIa).

In particular, the adduct is a compound of formula (IIa), $$T\text{-}X'\text{-}L_1\text{-}Y\text{-}L_2\text{-}Z \qquad (IIa)$$

wherein
X' is a moiety resulting from the reaction of a reactive group X on compound (I), X is a carbonyl reactive group, a dienophilic group, a carboxylate reactive group, a phenol reactive group, an amino reactive group, or a hydroxyl reactive group, $L_1$ is a bond or a spacer, Y is a neutral ion loss unit which, under conditions of mass spectrometry, is capable of fragmentation, whereby a neutral species, particularly a low-molecular weight neutral species is released, $L_2$ is a bond or a spacer, Z is a charge unit comprising at least one negatively charged moiety, including any salt thereof, or a composition or kit comprising at least one adduct of formula (IIa).

An adduct compound may also be provided as a pure substance for use as a calibrator and/or as a standard. Use of the adduct compound (II) or (IIa) as a calibrator may involve generating a calibration curve for a specific analyte molecule, wherein different known amounts of adduct compound (II) or (IIa) are subjected to MS analysis and the respective signal intensities are measured in order to allow an accurate quantitative determination of an unknown amount of the analyte molecule present in a sample.

Use of the adduct compound (II) as a standard may involve adding known amounts of the reagent-analyte adduct, e.g. in the form of an isotopologue to individual portions, e.g. aliquots, of a sample and separate mass spectrometric analysis of these individual sample portions. The resulting different signal intensities for the analyte-reagent adduct in these sample portions allow an accurate quantitative determination of an unknown amount of the analyte molecule present in the sample.

Further, a known analyte can be provided as the standard, which may be added in a known amount, e.g. in the form of an isotopologue, to a sample or to individual portions, e.g. aliquots, of a sample. Treating a sample with a reagent of formula (I) or (Ia) then yields a mixture of a standard adduct and an adduct formed from the reagent of formula (I) or (Ia) and the analyte to be determined.

According to a preferred embodiment, either the known analyte of the standard, the reagent of formula (I) or (Ia) or both can be used in the form of an isotopologue.

The mixture of the standard adduct and the adduct formed by reaction of the analyte to be determined with a reagent of formula (I) can then be analyzed using mass spectrometry. In some embodiments, a relative concentration of an analyte can be obtained. In other embodiments, absolute quantitation of an analyte can be obtained by using a known concentration of a standard.

The standard may be added to the sample before, during or after the adduct between the analyte molecule in the sample and the reagent compound (I) is formed. Preferably, the internal standard is added before the adduct between the analyte molecule in the sample and the reagent compound (I) or (Ia) is formed.

Preferably, the standard adduct is MS-distinguishable from the adduct generated by reaction of a reagent compound (I) or (Ia) and the analyte molecule present in the sample. For this purpose, the standard adduct may be generated from an isotopologue of the reagent compound (I) or (Ia) whereas the adduct of the analyte molecule in the sample may be generated by using an isotopically neutral, i.e. non-labelled, reagent compound (I) or (Ia) or an isotopologue different from the standard. Alternatively or additionally, the analyte of the standard can be an isotopologue.

During chromatographic separation, such as gas or liquid chromatography, the isotopologue standard adduct has the same retention time as the analyte adduct from the sample. Thus, both the analyte adduct and the isotopologue standard adduct enter the mass spectrometer at the same time.

The isotopologue standard adduct, however, exhibits a different molecular mass than the analyte adduct from the sample. This allows a mass spectrometric distinction between ions from the added standard adduct and ions from the analyte adduct by means of their different mass/charge (m/z) ratios. Both adducts are subject to fragmentation by release of the first neutral species as described above and provide daughter ions. These daughter ions can be distinguished by means of their m/z ratios from each other and from the respective adduct ions. Consequently, a separate determination and quantification of the signals from the isotopologue standard adduct and the analyte adduct can be performed. Since the isotopologue standard adduct has been added in known amounts, the signal intensity of the analyte adduct from the sample can be attributed to a specific quantitative amount of the analyte.

Still a further aspect of the present invention relates to a method for the mass spectrometric determination of an analyte molecule comprising the steps:

(a) covalently reacting the analyte molecule with a reagent compound of formula (I) as described above, whereby an adduct of the analyte molecule and the reagent compound is formed, and (b) subjecting the adduct from step (a) to a mass spectrometric analysis.

In particular embodiments, the reaction of the compound of formula (I) and the analyte molecule of step a) takes place before any enrichment process of the analyte molecule, takes place subsequent to a first enrichment process, or takes place subsequent to a second enrichment process. in the context of the present disclosure, the term "first enrichment process" or "first enrichment workflow" refers to an enrichment process which occurs subsequent to the pre-treatment of the sample and provides a sample comprising an enriched analyte relative to the initial sample. In the context of the present disclosure the term "second enrichment process" or "second enrichment workflow" refers to an enrichment process which occurs subsequent to the pre-treatment and the first enrichment process of the sample and provides a sample comprising an enriched analyte relative to the initial sample and the sample after the first enrichment process. In particular embodiments, the first enrichment process includes the use of analyte selective magnetic beads. In particular embodiments, the second enrichment process includes the use of chromatographic separation, in particular using liquid chromatography.

In particular embodiment, wherein the reaction of the compound of formula (I) and the analyte molecule of step a) takes place before any enrichment process, the compound of formula (I) is added to the pre-treated sample of interest. The term "pre-treated sample" refers to the treatment of a blood sample with an internal standard (IS) and a hemolysis reagent (HR) as described in detail above, or to the treatment of a urine sample with an internal standard (IS) and an enzymatic reagent (E) as described in detail above. Accordingly, the adduct of the analyte molecule and the reagent compound of formula (I) is formed after the pre-treatment and prior to the first enrichment process. The adduct is thus, subjected to the first enrichment process and to the second enrichment process before being subjected to the mass spectrometric analysis of step b).

In particular embodiment, wherein the reaction of the compound of formula (I) and the analyte molecule of step a) takes place subsequent to a first enrichment process, the compound of formula (I) is added to the sample of interest after the first enrichment process using magnetic beads is concluded. Accordingly, in this case, the sample is first pre-treated as described herein above, is then subjected to magnetic beads carrying analyte selective groups as described herein above, and prior to, simultaneously with or subsequently to the elution from the beads, the compound of formula (I) is added. Accordingly, the adduct of the analyte molecule and the reagent compound of formula (I) is formed after the first enrichment process and prior to the second enrichment process. The adduct is thus, subjected to the second enrichment process before being subjected to the mass spectrometric analysis of step b).

In particular embodiment, wherein the reaction of the compound of formula (I) and the analyte molecule of step a) takes place subsequent to a second enrichment process, the compound of formula (I) is added to the sample of interest after the second enrichment process using chromatography, in particular liquid chromatography, is concluded. Accordingly, in this case, the sample is first pre-treated as described herein above, is then subjected to a magnetic bead workflow as described herein above, followed by chromatographic separation, in particular using liquid chromatography, particularly HPLC, rapid LC, or micro LC (μLC), and subsequent to chromatographic separation the compound of formula (I) is added. Accordingly, the adduct of the analyte molecule and the reagent compound of formula (I) is formed after the second enrichment process. The adduct is thus, not subjected to a enrichment process before being subjected to the mass spectrometric analysis of step b).

Preferably, the mass spectrometric analysis step (b) comprises:
(i) subjecting an ion of the adduct to a first stage of mass spectrometric analysis, whereby the ion of the adduct is characterised according to its mass/charge (m/z) ratio,
(ii) causing fragmentation of the adduct ion, whereby a first neutral species, particularly a low-molecular weight neutral species is released and a daughter ion of the adduct is generated, wherein the daughter ion of the adduct differs in its m/z ratio from the adduct ion, and
(iii) subjecting the daughter ion of the adduct to a second stage of mass spectrometric analysis, whereby the daughter ion of the adduct is characterized according to its m/z ratio.

Optionally, the adduct ion is subject to alternative fragmentation, whereby a second neutral species different from the first neutral species is released and a second alternative daughter ion of the adduct is generated. In this case, both the first and second daughter ions of the adduct may be subjected to the second stage of mass spectrometric analysis, whereby both the first and second daughter ions of the adduct are characterized according to their m/z ratios. The use of a reagent compound (I) which allows a second alternative neutral ion loss, e.g. by release of an aryl or halogen radical, provides additional information on the presence and/or amount of the analyte molecule in the sample. This is particularly relevant for the analysis of complex biological samples.

The present invention allows determination of a single analyte or a plurality of different analyte molecules in a sample. The present invention, however, also allows multiplexing, i.e. determination of a plurality of different analyte molecules in a plurality of samples.

Particular compounds are considered to be advantageous when used in mass spectrometry. Accordingly, in further aspects, the present invention relates to the compounds disclosed below:

In a further aspect, the present invention provides a reagent for use in mass spectrometry, which is a compound of formula (Ia)

$$X\text{-}L_1\text{-}Y\text{-}L_2\text{-}Z \tag{Ia}$$

wherein X, Y, Z, $L_1$ and $L_2$ are as defined above.

In particular, the present invention relates to a reagent which is a compound of formula (Ia)

$$X\text{-}L_1\text{-}Y\text{-}L_2\text{-}Z \tag{Ia}$$

wherein
X is a carbonyl reactive group, a dienophilic group, a carboxylate reactive group, a phenol reactive group, an amino reactive group, a hydroxyl reactive group, or a thiol reactive group, under the provision that X is no acrylester,
$L_1$ is a bond or a spacer,
Y is a neutral ion loss unit which, under conditions of mass spectrometry, is capable of fragmentation, whereby a neutral species, particularly a low-molecular weight neutral species, is released,
$L_2$ is a bond or a spacer,
Z is a charge unit comprising at least one permanently positively charged moiety as defined above, preferably tetralkylammonium, 1 alkyl pyridinium, or 1,3 dialkyl imidazolium unit,
including any salt thereof, or a composition or kit comprising at least one compound (Ia).

In particular, the present invention relates to a reagent which is a compound of formula (Ia), $$X\text{-}L_1\text{-}Y\text{-}L_2\text{-}Z \tag{Ia}$$

wherein
X is a carbonyl reactive group, a dienophilic group, a carboxylate reactive group, a phenol reactive group, an amino reactive group, or a hydroxyl reactive group,
$L_1$ is a bond or a spacer,
Y is a neutral ion loss unit which, under conditions of mass spectrometry, is capable of fragmentation, whereby a neutral species, particularly a low-molecular weight neutral species is released,
$L_2$ is a bond or a spacer,
Z is a charge unit comprising at least one negatively charged moiety,
including any salt thereof, or a composition or kit comprising at least one compound (Ia).

In embodiments, the reactive group X of compound (Ia) as specified above may be selected to react with different functional groups on an analyte molecule as disclosed herein above. It is within common knowledge to decide which reactive groups X will qualify for binding to a functional group of an analyte of interest. Functional groups on an analyte molecule are vicinal diols, phenol groups, nucleobases, amino, mercapto, hydroxy, 1-hydroxy 2-amino alkyl, 1-amino 2-mercapto alkyl, keto, 1,3-dienyl, enyl, allyl, formyl, and carboxylate groups. Reactive groups are summarized in standard text books "Bioconjugate Techniques" 3rd edition: https://doi.org/10.1016/B978-0-12-382239-0.00025-X; and "The Molecular Probes Handbook: A Guide to Fluorescent Probes and Labeling Technologies", 11th Edition ed Iain D. Johnson, Life Technologies Corporation, 2010; and review articles (e.g. X. Chen et al., Org. Biomol. Chem., 2016, 14, 5417-5439; and T. Higashi J Steroid Biochem Mol Biol. 2016 September; 162:57-69).

In particular, the reactive group X is a carbonyl-reactive group, a dienophilic group, a carboxylate reactive group, a phenol reactive group, an amino reactive group, a hydroxyl reactive group, or a thiol reactive group. In particular, the reactive group X is selected from the group consisting of an amine reactive group, a thiol reactive group, a carbonyl reactive group, a dienophilic group, a 1,2 diol reactive group, a carboxylate reactive group, a hydroxyl reactive group, a 1-amino 2 hydroxy alkyl reactive group, an 1-amino 2 mercapto reactive group, and a group reacting at the ortho positions of phenols.

In a preferred embodiment, group X is a carbonyl-reactive group, which is capable of reacting with any type of molecule, e.g. carbohydrate molecule, having a carbonyl group. In particular, the carbohydrate-reactive group X of compound is capable of reacting with all types of sugars including aldoses, such as glucose, mannose, galactose, ribose or fucose, and ketones such as ribulose or fructose as well as with oligosaccharides such as di-, tri- or tetrasaccharides and polysaccharides having an accessible aldehyde or keto group or a hemiacetal masked aldehyde or keto group. The carbonyl-reactive group may have either a super-nucleophilic N atom strengthened by the α-effect through an adjacent O or N atom $NH_2$—N/O or a dithiol molecule. It may be selected from:
(i) a hydrazine group, e.g. a $H_2N$—NH—, or $H_2N$—$NR^1$— group, wherein $R^1$ is aryl, or $C_{1-4}$ alkyl, particularly $C_1$ or $C_2$ alkyl, optionally substituted e.g. with halo, hydroxyl, and/or $C_{1-3}$ alkoxy,
(ii) a hydrazone group, e.g. a $H_2N$—NH—C(O)—, or $H_2N$—$NR^2$—C(O)— group, wherein $R^2$ is aryl or $C_{1-4}$ alkyl, particularly $C_1$ or $C_2$ alkyl, optionally substituted e.g. with halo, hydroxyl, and/or $C_{1-3}$ alkoxy,
(iii) a hydroxylamino group, e.g. a $H_2N$—O— group, and
(iv) a dithiol group, particularly a 1,2-dithiol or 1,3-dithiol group.

In a preferred embodiment, reactive group X is a keto reactive group, which is capable of reacting with each analyte comprising a keto group eg ketosteroids like DHT, testosterone, epitestosterone, desoxymethyl testosterone (DMT), tetrahydrogestrinone (THG), aldosterone, estrone, 4-hydroxyestrone, 2-methoxyestrone, 2-hydroxyestrone, 16-ketoestradiol, 16 alpha-hydroxyestrone, 2-hydroxyestrone-3-methylether, prednisone, prednisolone, pregnenolone, progesterone, DHEA (dehydro epiandrosterone), 17 OH pregnenolone, 17 OH progesterone, 17 OH progesterone, androsterone, epiandrosterone, and delta 4 androstenedione) 11-desoxycortisol corticosterone, 21 deoxycortisol, 11 deoxycorticosterone, allopregnanolone, and aldosterone.

For example, a reactive haloacetyl group as Br/I—$CH_2$—C(O)—, an acrylamide/ester group, an imide such as maleimide or methylsulfonyl phenyloxadiazole (N. Toda, et al., Angew. Chem. Int Ed Engl. 2013 Nov. 25; 52(48)) may react with nucleophilic groups such as thiol groups on an analyte molecule. An amino-reactive group, e.g. an active ester group such as N-hydroxy succinimide (NHS) or sulfo-NHS ester, pentafluoro phenyl ester, quadratic acid esters, a hydroxybenzotriazole (HOBt) ester, or 1-hydroxy-7-azabenzotriazole (HOAt) ester group, sulfonylchloride, or an isothiocyanoto or isocyanato group may react with amino groups on an analyte molecule. A hydrazine or hydroxyl amino group as described above may also be used to react with other electrophilic groups present on an analyte molecule.

For binding to vicinal diols, the reactive group X may comprise boronic acid. Alternatively, diols can be oxidized to the respective ketones or aldehydes and then reacted with ketone/aldehyde-reactive groups X. Dienophils as triazol dione can be selected as the reactive group X for binding to dienes. Phenol groups present on an analyte molecule can be reacted with triazole dione via en reaction (H. Ban et al *J. Am. Chem. Soc.*, 2010, 132 (5), pp 1523-1525) or by diazotization or alternatively by ortho nitration followed by reduction to an amine which could than be reacted with an amine reactive reagent. Nucleobases can be reacted with chloro acetyl or Pt complexes as the reactive group X. Terminal cysteines can be reacted with heteroaryl/aryl cyanides as the reactive group X. Terminal serines can be oxidized to yield aldehyde groups and then reacted with known aldehyde-reactive groups X. Depending on the functional groups present on an analyte molecule to be determined, the skilled person will select an appropriate reactive group X for compound (Ia).

In a further embodiment, the reactive group is a carboxylate reactive group e.g. a diazocompound (Chromatographia 2012, 75, 875-881) which can be used for derivatization of prostaglandins. Other well known carboxylate reactive groups are alkylhalides. Well known is also the activation of the carboxylic acid followed by reaction with an nucleophile like an amine or hydrazine (A. Kretschmner et al Journal of Chromatography B Volume 879, 17-18, May 2011, Pages 1393-1401).

Hydroxyl reactive groups are (T. Higashi J Steroid Biochem Mol Biol. 2016 September; 162:57-69) sulfonylchlorides, activated carboxylic esters (NHS, or imidazolide), and fluoro aromates/heteroaromates capable for nucleophilic substitution of the fluorine.

In a preferred embodiment, reactive group X is a phenol-reactive group, which is capable of reacting with any type of molecule having a phenol group, e.g. steroids, steroid-like compounds, estrogen, estrogen-like compounds, estrone (E1), estradiol (E2), 17a-estradiol, 17p-estradiol, estriol (E3), 16-epiestriol, 17-epiestriol, and 16,17-epiestriol, and/or metabolites thereof. By way of example, the phenol-reactive group may be a 1,2,4 triazolin 3,5 dione group. 1,2,4 triazolin 3,5 diones are also capable to act as a dienophile and are therefore useful for detection of vitamin D 1α,25 $(OH)_2VitD_3$, 1α,25$(OH)_2VitD_2$, 25(OH)$VitD_2$, 25(OH)$VitD_3$ and 24R,25$(OH)_2VitD_3$.

The compound (Ia) further comprises a neutral ion loss unit Y. In the context of the present application, the term "neutral ion loss unit" refers to a unit, which is able to lose a moiety having no charge. Said moiety includes, but is not limited to ions, atoms and a plurality of atoms. The unit Y is neutral, i.e. it does not carry a positive or negative charge and it is linked to the reactive group X via a linker $L_1$ as defined herein below. The neutral unit Y is, under conditions of MS, e.g. when subjected to collision-induced dissociation (CID), for example in triple quadrupole MS, capable of fragmentation, whereby a neutral species is released. After release of the first neutral species, the remainder of unit Y still remains neutral. Typically, but not necessarily, one neutral species is released, i.e. a first neutral species is released. In particular embodiments, two neutral species are released.

The first neutral species may be a low molecular weight neutral species, e.g. a neutral molecule having a molecular weight of 100 or less, more particularly of 80 or less. Further, the first neutral species may be an inorganic molecule such as SO, $SO_2$, CO, $CO_2$, NO, $NO_2$ or $N_2$. In particular, the neutral species is $N_2$ or $SO_2$. More particularly, the first neutral species is $N_2$. The reaction that leads to the loss of the neutral molecule may be preferentially a cycloreversion reaction, in particular a 1,3-dipolar cycloreversion. In the context of the present disclosure, the term "cycloreversion" refers to the reversal of any cycloaddition reaction.

In particular embodiments, the neutral ion loss unit Y comprises or consists of a cyclic moiety (e.g. cyclic ketones like bicyclo[2.2.1]heptadien-7-one are known to lose CO), particularly a heterocyclic moiety, more particularly a 6-, 5-, or 4-membered heterocyclic moiety, which is capable of fragmentation, whereby the first neutral species as described above is released. Such (hetero)cyclic groups readily show fragmentation by means of a retro (hetero)cycloaddition reaction, whereby the neutral species is released.

Preferably, the neutral ion loss unit Y comprises or consists of a 5- or 6-membered heterocyclic moiety having at least two hetero atoms, such as N, O and/or S atoms, particularly N atoms, adjacent to each other, e.g. in 1,2-position, such as cyclic azo compounds and 5-membered rings selected form triazole, in particular 1,2,3-triazole, tetrazole, tetrazine, 1,2,3 oxa- or thia-diazole, or hydrogenated derivatives thereof. To the above mentioned heterocycles a further ring can be annealed eg benzothiadiazol, or benzotriazol. Heterocycles can be partially hydrogenated eg, 2,5 dihydro pyrrol, 2,5 dihydrothiophen 1,1 dioxide.

In an especially preferred embodiment, the 5-membered heterocyclic moiety is a triazole moiety, which may be synthesized via a cycloaddition or click reaction of an alkyne and an azide possibly but not necessarily in the presence of Cu (I) as a catalyst. Under conditions of MS, fragmentation of a triazole moiety causes a release of $N_2$ via a 1,3 dipolar cycloreversion reaction leading to a reduction of the mass/charge ratio (m/z) of 28 in the mass spectrometer.

The skilled person is well aware that neutral ion loss units may be identified using commercially available software, e.g. ACD/MS Fragmenter (ACD Labs). Further reactions and species which lead to neutral losses are described in the following references:

Carey, Sundberg: Organische Chemie, Ein weiterführendes Lehrbuch Korrigierter Nachdruck VCH 1995; ISBN: 3-527-29217-9;

Fred W. McLafferty, Frantisek Turecek, Interpretation von Massenspektren Springer Spektrum 1995, Softcover: ISBN978-3-642-39848-3.

In particular embodiments, the compound of formula (Ia) has a charge unit Z comprising at least one charged moiety, i.e. a moiety which is predominantly present in a charged state under substantially neutral conditions. For example, the charge unit Z comprises (i) at least one permanently positively charged moiety such as a primary, secondary, tertiary or quaternary ammonium group or a phosphonium group, particularly having a $pK_a$ of 10 or higher, more particularly having a $pK_a$ of 12 or higher, or (ii) at least one negatively charged moiety such as a phosphate, sulphate, sulphonate or carboxylate group, particularly having a $pK_b$ of 10 or higher, more particularly having a $pK_b$ of 12 or higher.

In the context of the present application, the term "having a $pK_a$ of" refers to the fact that a charged moiety provides the overall molecule with a certain $pK_a$ value which differs from the $pK_a$ value of the molecule without the charged moiety. Exemplified, the term "at least one positively charged moiety having a $pK_a$ of 10 or higher" specifies that the overall molecule comprising said at least one positively charged moiety, exhibits a $pK_a$ of 10 or higher. The same also applies analogously to $pK_b$ values.

The charge unit Z is linked to the neutral ion loss unit Y via a linker $L_2$ as defined herein. Accordingly, charge and ability to undergo a neutral loss are provided by different units. Even under conditions where the neutral ion loss unit Y is fragmented leading to a release of a (low molecular weight) neutral species, the charge unit Z remains unchanged. This means that the state of charge of the remaining residue does not change. If the compound was previously positively charged due to a positive charge in the charge unit Z, it remains positively charged even after release of the low molecular weight neutral species.

Preferably, the compound (I) has a charge unit Z comprising at least one positively charged moiety. Most preferably, the charge unit Z consists of one positively charged moiety and lacks any groups capable to undergo an alternative fragmentation.

A charge is permanent, e.g. when using a quaternary ammonium group, or may be generated by protonation (positive charge) or deprotonation (negative charge). Preferred permanent positive charge units are tetralkylammonium, 1 alkyl pyridinium, and 1,3-dialkyl imidazolium units.

In addition to the release of the first neutral species, the compound (Ia) may be capable of an alternative fragmentation under conditions of mass spectrometry, e.g. via CID. Thereby a second neutral species different from the first neutral species is released. For example, the second neutral species may comprise an aryl-radical, e.g. a phenyl- or substituted phenyl-radical or a halogen radical (Cl, Br, I). The alternative fragmentation leading to release of a second neutral species preferably takes place only under conditions of higher energy than required for release of the first neutral species from neutral ion loss unit Y.

Groups $L_1$ and $L_2$ in general formula (Ia) independently represent a bond, i.e. a covalent bond, or a spacer, i.e. a linear or branched spacer having a chain length from 1 up to usually 4, 6, 8 or 10 atoms or even more, e.g. C-atoms optionally including at least one heteroatom. Preferably, groups $L_1$ and $L_2$ are short spacers, having a length of 1, 2 or 3 atoms and most preferably lacking any moieties which may be subject to alternative fragmentation. Further, it is preferred for the groups $L_1$ and $L_2$ not to include any stereocenters. In case stereoisomers are present, only one species of stereoisomer is present but no mixture of two or more species of stereoisomers. For use in MS, compound (I) is preferably provided in stereoisomerically pure form. In particular embodiments, $L_1$ and $L_2$ are independently of each other C1-C4 alkyl spacers, optionally comprising at least one heteroatom. In further embodiments, one of $L_1$ or $L_2$ includes an aryl group, such as a phenyl group, which may be subject to alternative fragmentation as described above.

The reagent of formula (Ia) is advantageously designed so that under conditions of mass spectrometry, only at one position in the resulting adduct (H), namely the neutral ion loss unit Y, one single neutral loss takes place. If the adduct includes any further groups which may be subject to alternative fragmentation, e.g. in the spacers $L_1$ and/or $L_2$, said alternative fragmentation preferably takes place under conditions of higher energy than required for the release of the first neutral species from the neutral ion loss unit Y. Examples for alternative fragmentations include release of a second neutral species different from the first neutral species such as an aryl or halogen radical.

In a first embodiment of formula (Ia), the charge unit Z comprises or consists of a positively charged moiety such as a primary, secondary, tertiary or quaternary ammonium group or a phosphonium group. While the charge may in principle be permanent or may be generated by protonation, permanent charges are preferred, particularly those wherein the overall compound has a $pK_a$ of 10 or higher, more particularly having a pK$_a$ of 12 or higher. A particularly preferred reagent according to this embodiment is represented by formula (Ic):

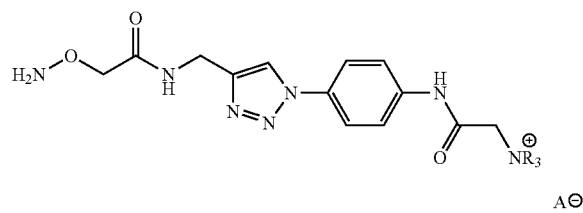

wherein R is in each case independently H or 01-4 alkyl, particularly methyl, and A is an anion, e.g. formate.

In another embodiment, the charge unit Z comprises or consists of a negatively charged moiety such as a phosphate, sulphate, sulphonate or carboxylate group. Particularly, a unit Z having a pK$_b$ of 10 or higher, more particularly having a pK$_b$ of 12 or higher, is preferred.

FIG. 1 shows an exemplary protocol for the quantitative determination of a single analyte molecule in a sample which comprises six different analyte molecules. The analyte molecules in the sample are reacted with a reagent compound (R), whereby six different analyte-reagent adducts are obtained. For the quantitative determination of one of the analyte molecules in the sample, a standard is added which has been prepared by reaction of the respective analyte molecule with a reagent isotopologue compound (R*). After chromatographic separation of the sample, e.g. by liquid chromatography (LC), the adduct of the analyte of interest with the unlabelled reagent (R) and the isotopologue thereof (R*) are not distinguishable. Thus, six signals derived from each of the different analytes are observed after chromatography. Mass spectrometric analysis, however, provides different signals from the unlabelled reagent (R) and the isotopologue (R*) due to the mass difference between both reagents. Due to the loss of a neutral species (here N$_2$) two daughter ions are generated which also provide different signals. Since the amount of added isotopologue adduct is known, an exact quantification of the analyte from the signal intensity of the unlabelled reagent is possible by means of calibration. Correspondingly, an accurate quantitative determination of other analytes in the sample is possible.

Figure 2:
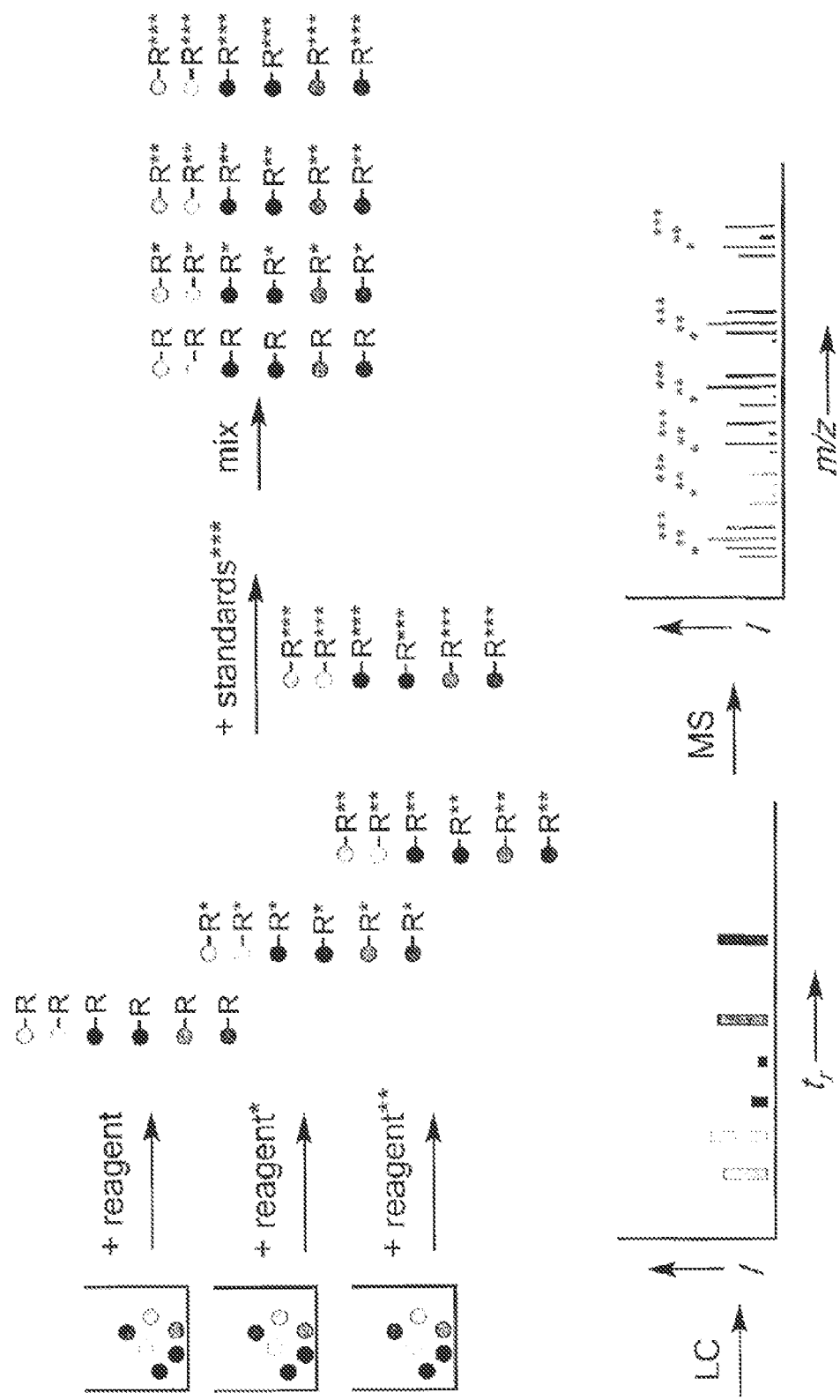

The use of a plurality of different isotopologues enables multiplexing. Thus, a direct comparison of a plurality of different samples or different amounts of analytes is possible. A respective exemplary protocol is shown in FIG. 2. Each sample comprises six different analyte molecules. In order to compare the quantitative amount of the six analyte molecules in three different samples, a different isotopologue reagent compound (R, R* and R**) is added to each sample. From this, three different sets of analyte-reagent adducts (R, R* and R) are obtained. Then, standards, e.g. adducts of the respective analyte and a further isotopically distinguishable reagent R* are added. After chromatographic separation, e.g. by LC, six signals, i.e. one signal for each analyte, are obtained. After MS analysis, 6×4 signals are obtained. Since the exact amount of the adduct of analyte and reagent R*** is known, a quantitative determination of all signals is possible.

Especially preferred embodiments of the present invention comprise a reaction of analyte molecules, preferentially of carbohydrates comprising at least one reactive aldehyde-, ketone- or semiacetal-group with the reagent or an isotopologue of the reagent and analysis of the formed adducts by GC or LC combined with MS, particularly by HPLC-triple quadrupole mass spectrometry.

The procedures of the present invention have two major advantages compared to common procedures. Because of the neutral ion loss in the mass spectrometer, detection of analyte molecules is possible with unprecedented sensitivity allowing diagnostics with minimum sample material. Upon addition of synthetic isotopically modified adducts as internal standards quantitative information about the analyte molecules can be obtained. This allows direct comparison of two and more samples e.g. tissue samples and multiplexing.

The present invention is suitable for clinical applications such as providing diagnostic and/or prognostic information on a subject, particularly a human subject. Specific applications are diagnosis of diseases associated with, accompanied by or caused by an alteration in the glycostructure of biomolecules, particularly of glycoproteins, for example the diagnosis of hyperproliferative diseases such as cancer, e.g. determination of the aggressiveness and invasiveness of tumors, characterization of platelets as well as measurement of the level of liver fibrosis, investigation of antibody characteristics and characteristics of immune cells such as T-cells. In general, the reagent (I) and its isotopologues can be used to obtain quantitative information about the presence and levels of specific glycobiomarkers in the field of glycomedicine.

FIGURE LEGENDS

FIG. 1: Schematic depiction of an embodiment of the invention.

A protocol for the quantitative determination of an analyte molecule comprises reacting the analyte molecules in a sample with a reagent (R) thereby forming covalent analyte adducts. Addition of a standard adduct comprising an isotopologue reagent (R*) allows quantitative determination of the analyte molecule by LC and subsequent MS.

FIG. 2: Schematic depiction of a further embodiment of the invention.

A protocol for the parallel quantitative determination of multiple analytes comprises reacting the analyte molecules in multiple samples with isotopically different reagents (R, R*, R) in each sample thereby forming covalent analyte adducts. Addition of a standard adduct comprising a further isotopologue reagent (R*) allows a parallel quantitative determination of each analyte molecule in each sample by LC and subsequent MS.

FIG. 3: Mechanism of the base excision repair process.
a Chemistry of base excision repair (BER) with formation of AP- and βE sites.
b Overview of epigenetic modifications at dC and possible removal of fdC and cadC through BER.
c Depiction of reagent 1 and of reaction products that are formed when 1 reacts with AP- and βE-sites.

Figure 4:
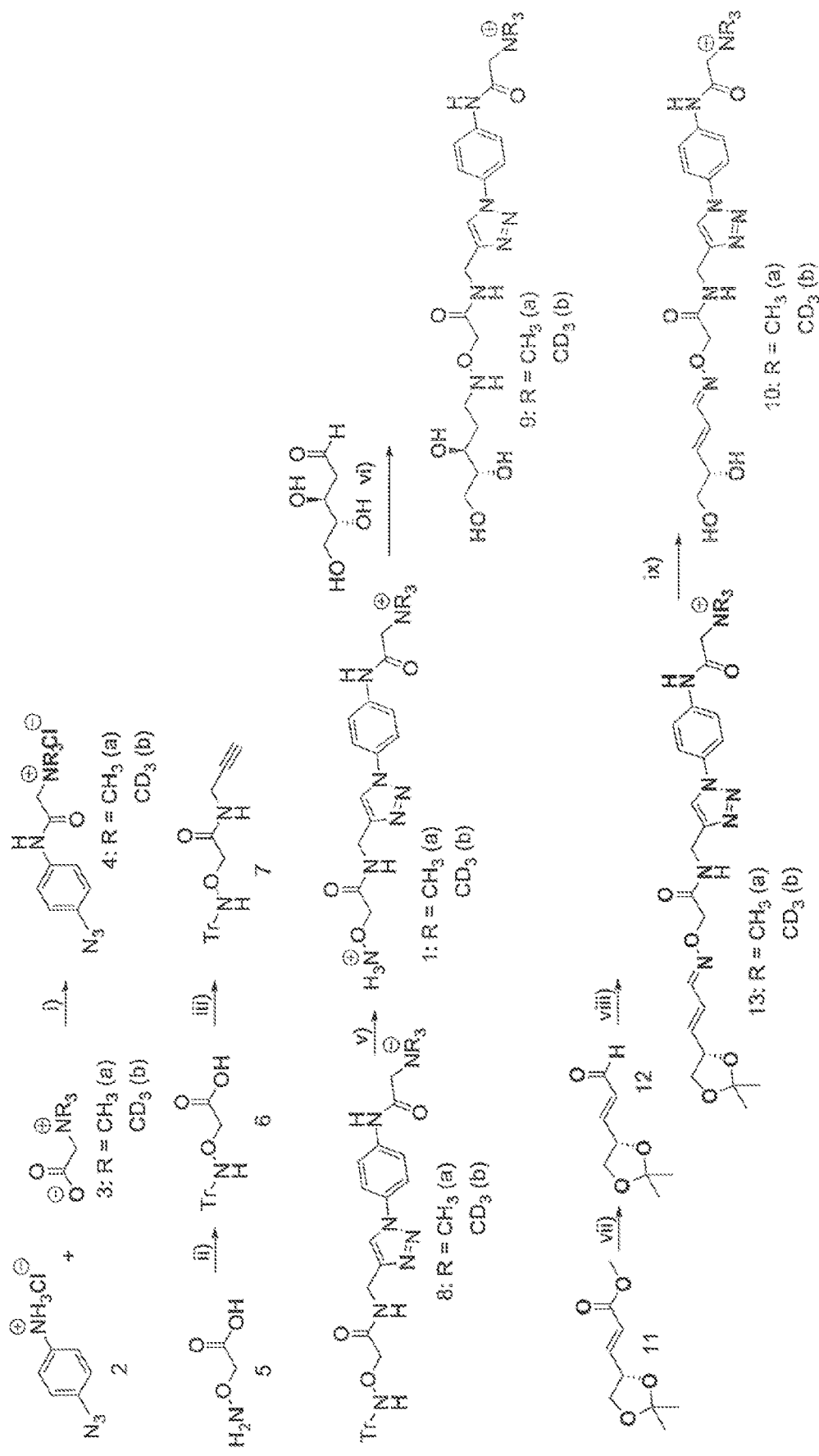

FIG. 4: Synthesis of reagent 1 in a light (a) and heavy (b) form and of internal standards 9a/b and 10a/b.
(i) TBTU, DIPEA, DMF, rt, 16 h, 90%;
(ii) Trt-Cl, NEt$_3$, pyridine, rt, 22 h, 74%;
(iii) propargylamine, TBTU, DIPEA, DCM, rt, 15 h, 92%;
(iv) 7+4a/b, CuBr.SMe$_2$, H$_2$O/DCM (1:1), rt, 16 h, 77%;
(v) 6M HCl, DCM/H$_2$O (1:1), rt, 1 h, quant.;
(vi) H$_2$O, 30° C., 16 h, HPLC, 15%;
(vii) 1) DIBAL-H, DCM, −78° C. to rt, (2) DMP, DCM, 0° C. to rt, o/n, 47% over two steps;

(viii) (1) 1a/b, CHCl$_3$/H$_2$O (1:1), rt, 16 h, 68%, (2) pTSA.H$_2$O, H$_2$O, 25° C., o/n, HPLC (2×), 14%.

Figure 5:
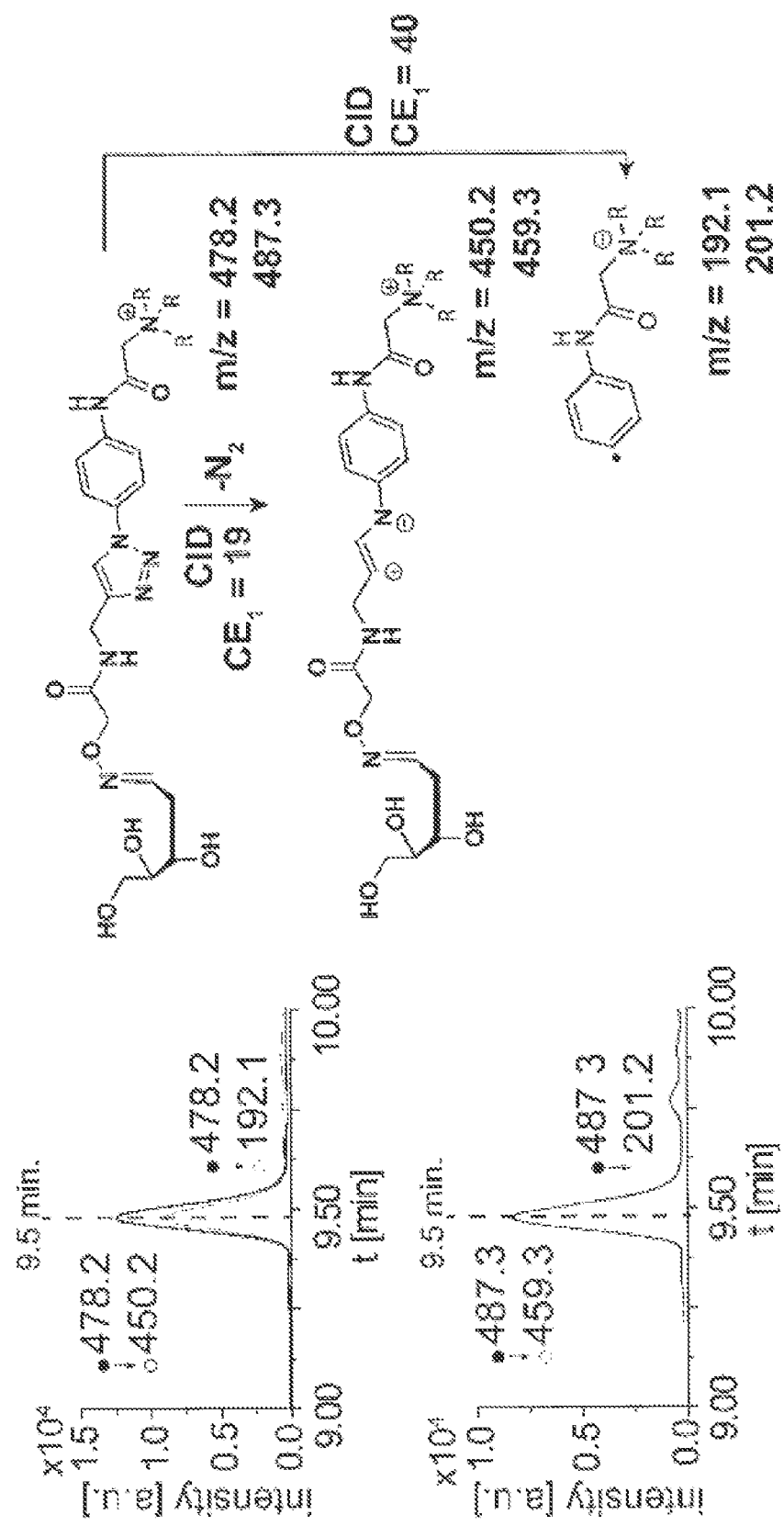
Figure 5:
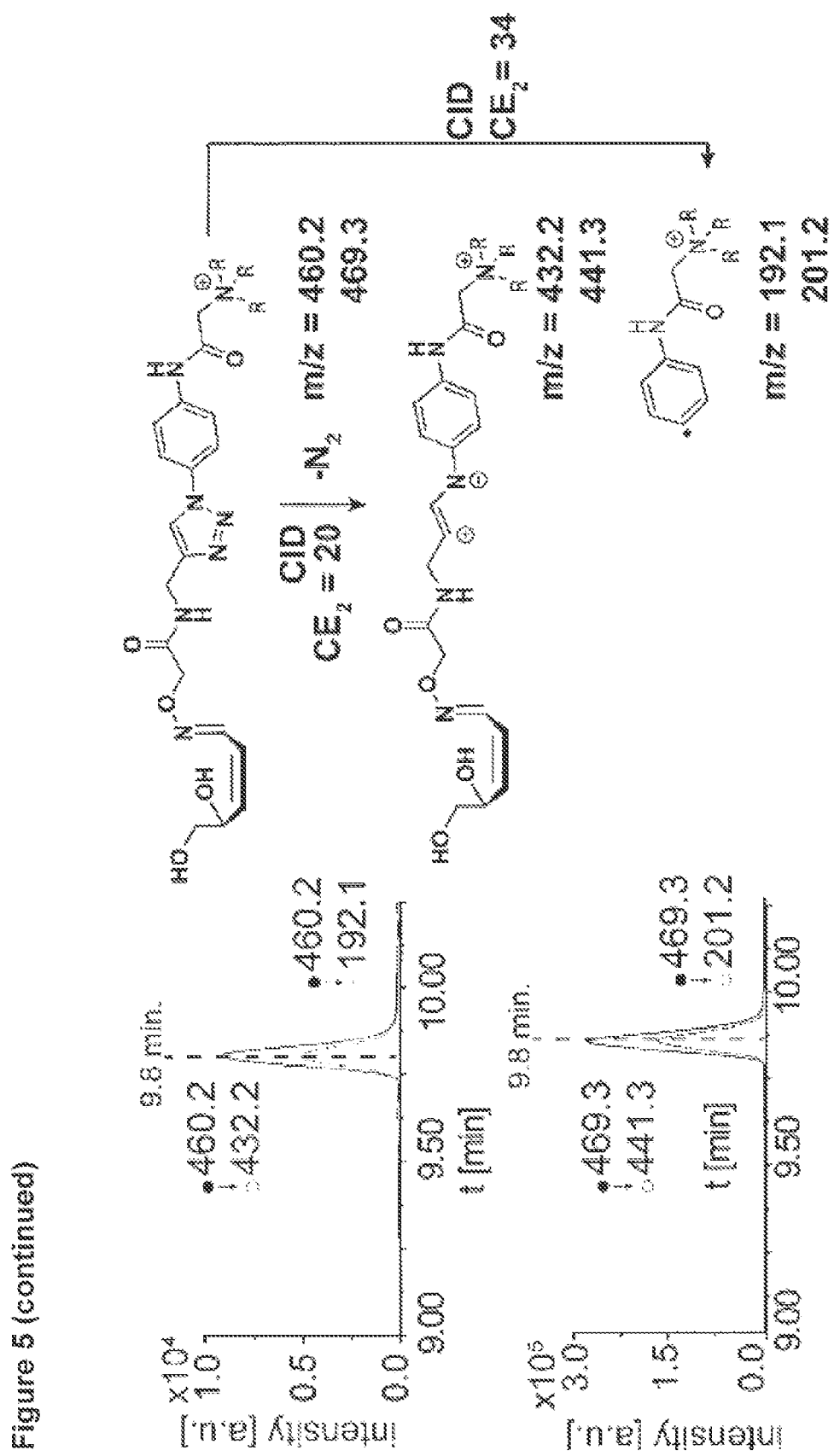

FIG. 5: MS/MS based method for the quantification of AP- and βE-sites.

Fragmentation patterns of AP (9)- and βE-site (10) standards in the MS/MS experiment yielding highly sensitive signals.

Figure 6A:
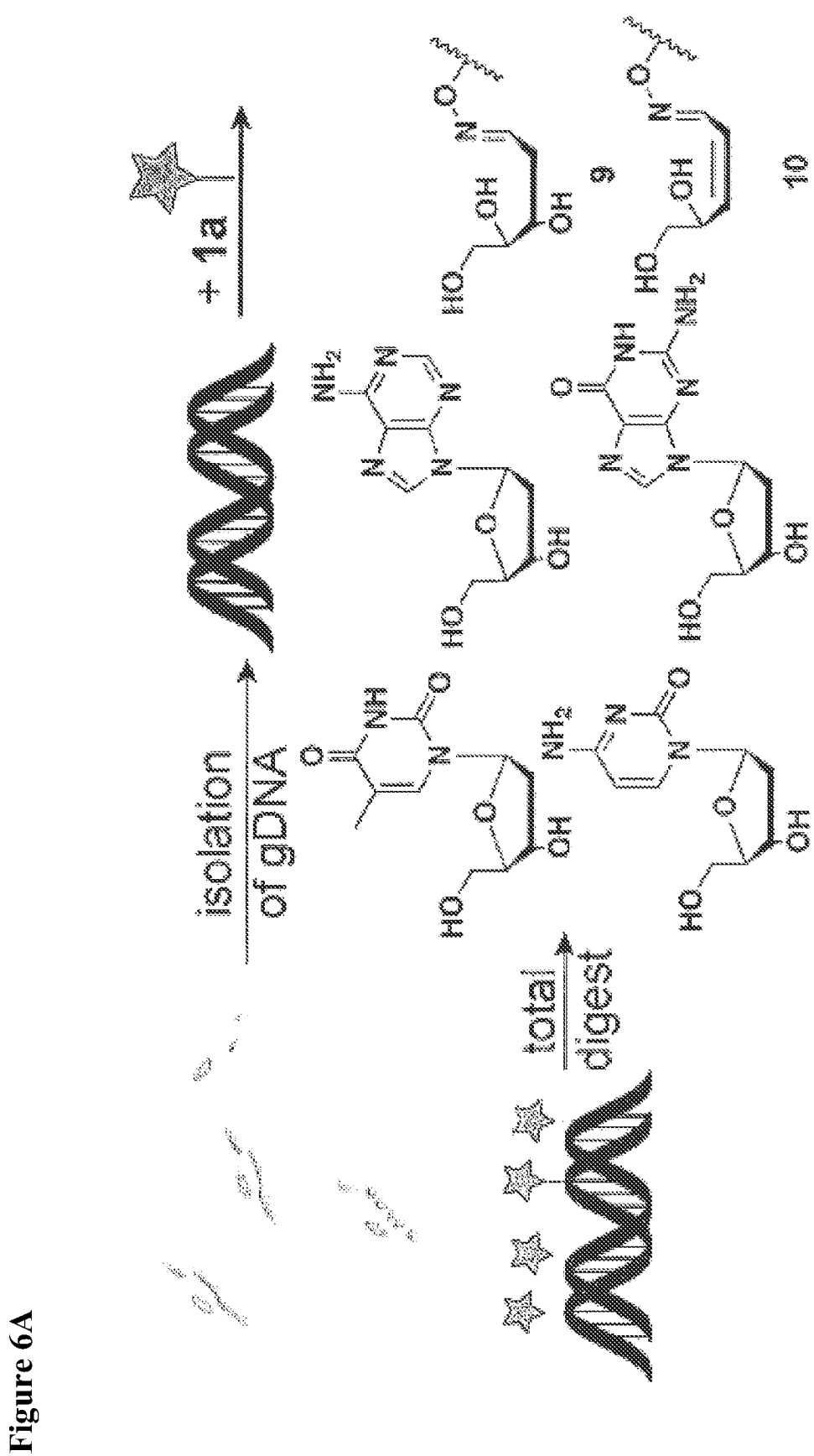

FIG. 6: Quantification of BER intermediates and isotope tracing studies.

a General workflow for the derivatization and analysis of AP- and βE-sites.

b Feeding of mESC cultures with labelled nucleosides results in the formation of ribose-labelled AP- and βE-site products 9 and 10 which are 5 mass units heavier than unlabelled products.

c Quantitative data of the different labelled adducts and DNA-modifications.

FIG. 7:

Calibration curve for a AP-(9) and b βE-site (10).

Figure 8A:
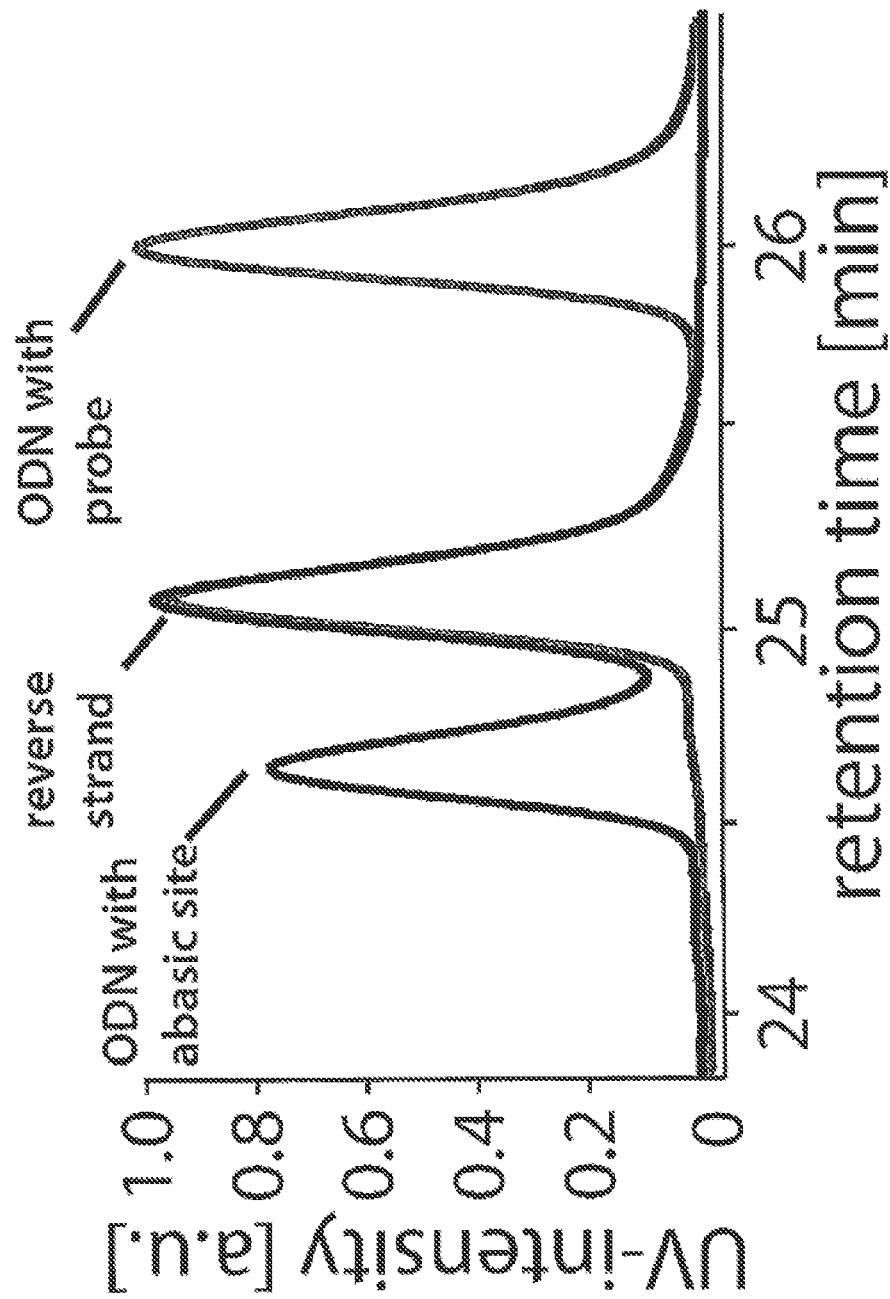
Figure 8B:
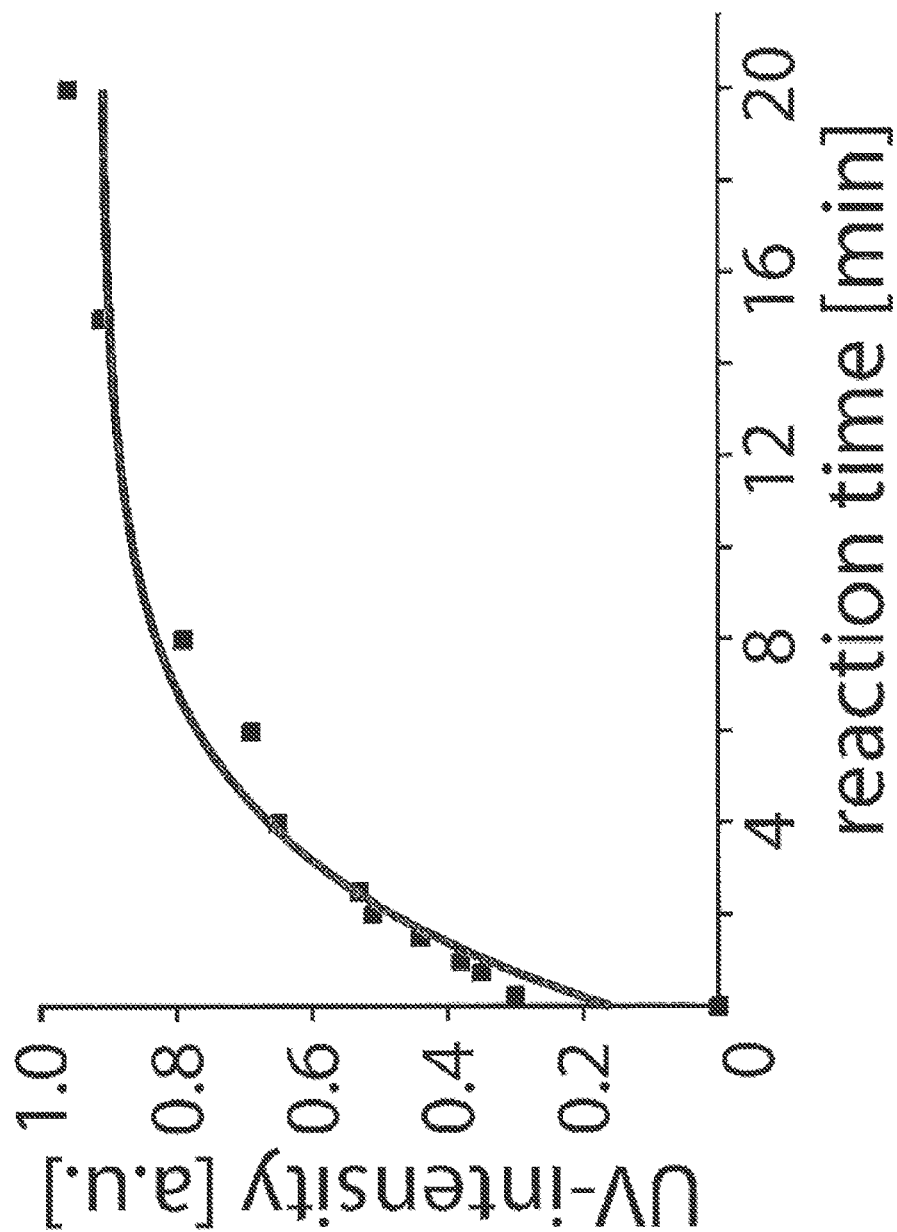

FIG. 8: Reaction kinetics on an oligodeoxy nucleotide (ODN) with a defined abasic site.

a Obtained UV-signals of an ODN with an abasic site and reverse strand before (black lines) and after derivatization with 1a.

b Normalized UV signals of an ODN+1 after specific time points.

FIG. 9:

Derivatization of gDNA with 1 shows that the derivatization reaction is fast and does not artificially generate abasic sites.

FIG. 10:

Scheme of the reaction of an acrylamide reagent with a thiole such as glutathione (GSH) and N$_2$-loss in MS analysis.

Figure 11:
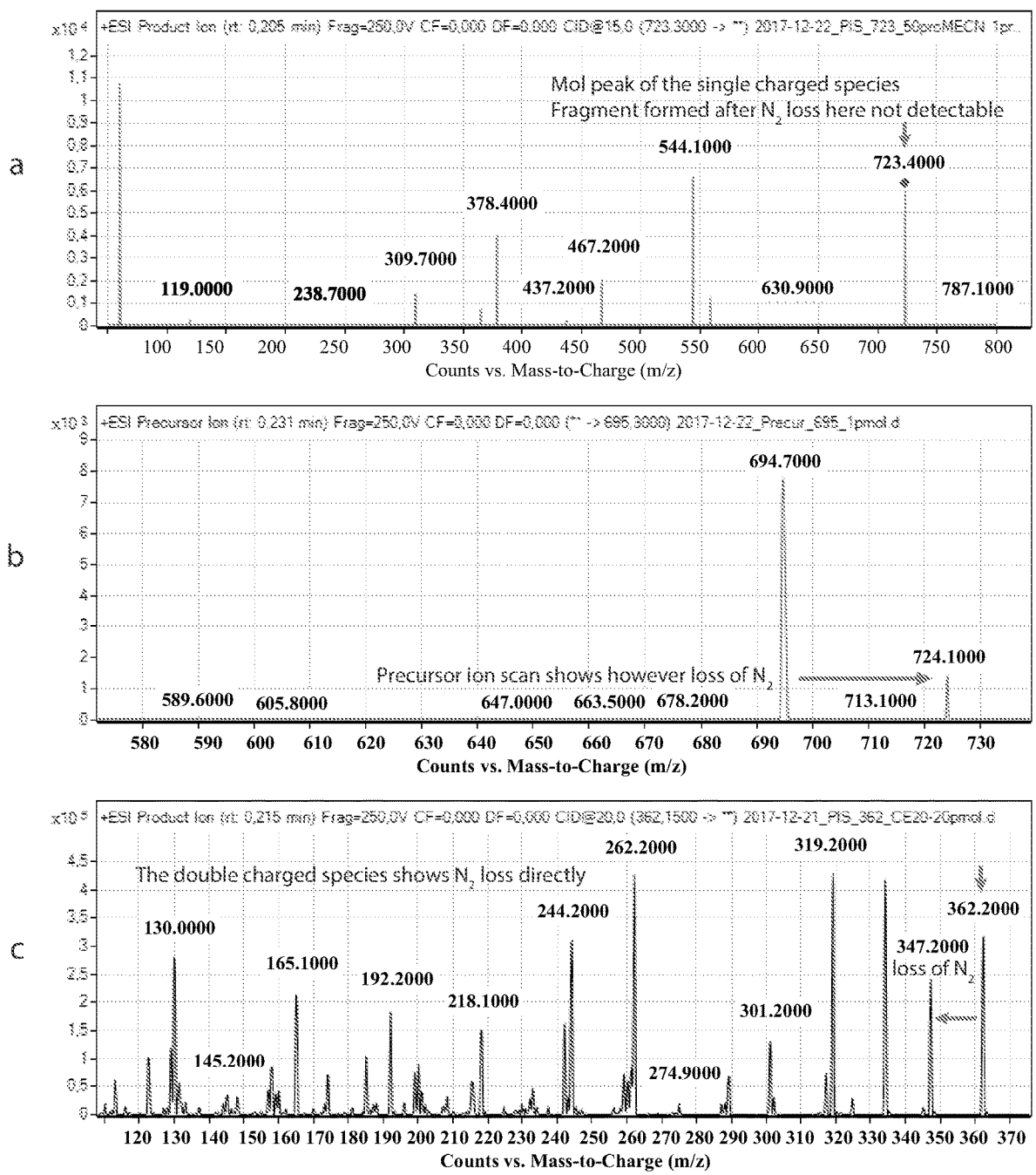

FIG. 11: MS analysis of a GSH adduct with an acrylamide probe.

a Mol peak of the single-charged species is indicated with ♦. Fragment formed after N$_2$ loss is not detectable.

b Precursor ion scan shows loss of N$_2$.

c The double-charged species shows N$_2$ loss directly.

Figure 12:
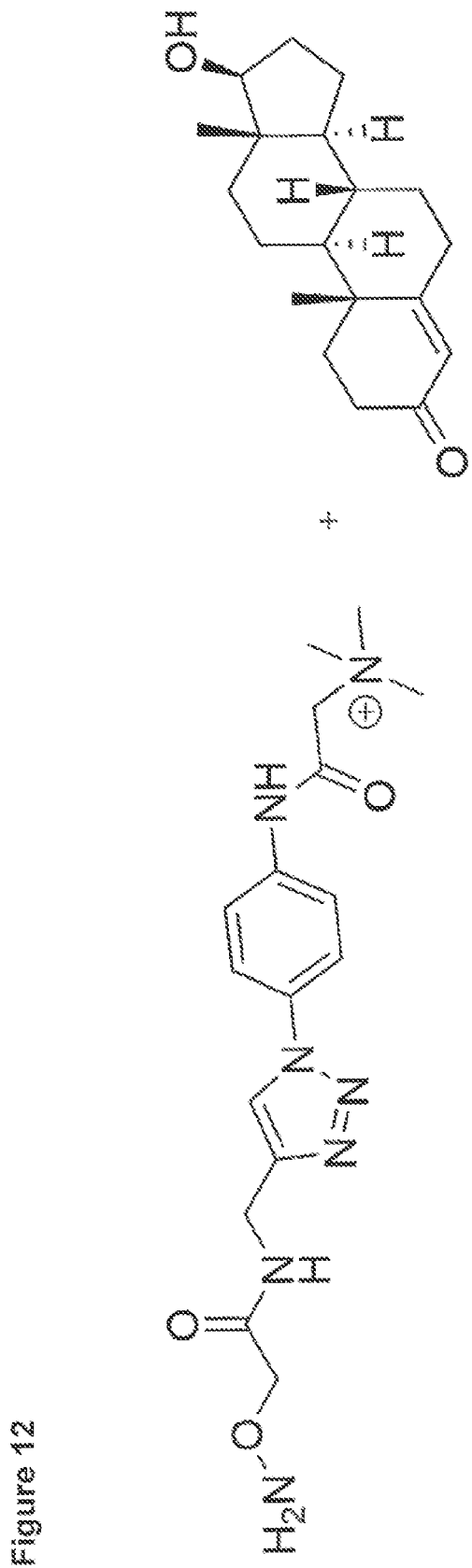

FIG. 12: Scheme of the reaction of a hydroxylamine reagent with testosterone FIG. 13: MS analysis of a testosterone adduct with a hydroxylamine probe MS experiments show the molecule peak at 632.5 and the fragments at 604.4 after N$_2$ loss as well as the second fragment at 192.1

Figure 14:
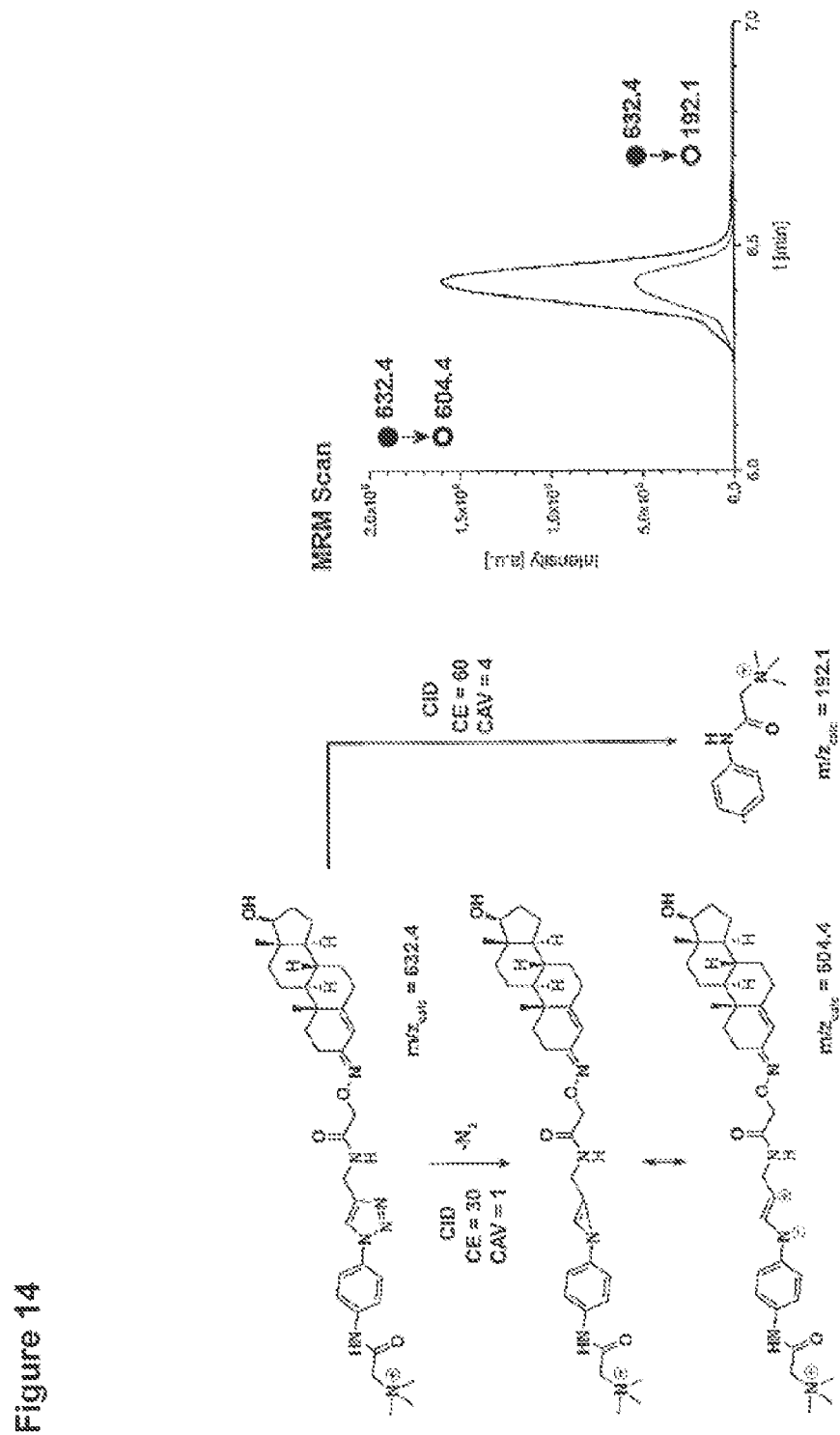

FIG. 14: MRM scan showing fragmentation of the testosterone adduct by loss of N$_2$ FIG. 15: Mass spectrometric analysis of testosterone using a hydroxylamine reagent The following peaks are shown:

a testosterone (110 amol)
b testosterone (22 amol)
c adduct N$_2$ loss (0.12 amol)
d adduct phenyl loss qualifier (0.12 amol)
e adduct N$_2$ loss (3.6 amol)
f adduct phenyl loss qualifier (3.6 amol)
g testosterone (11 fmol)

Figure 16:
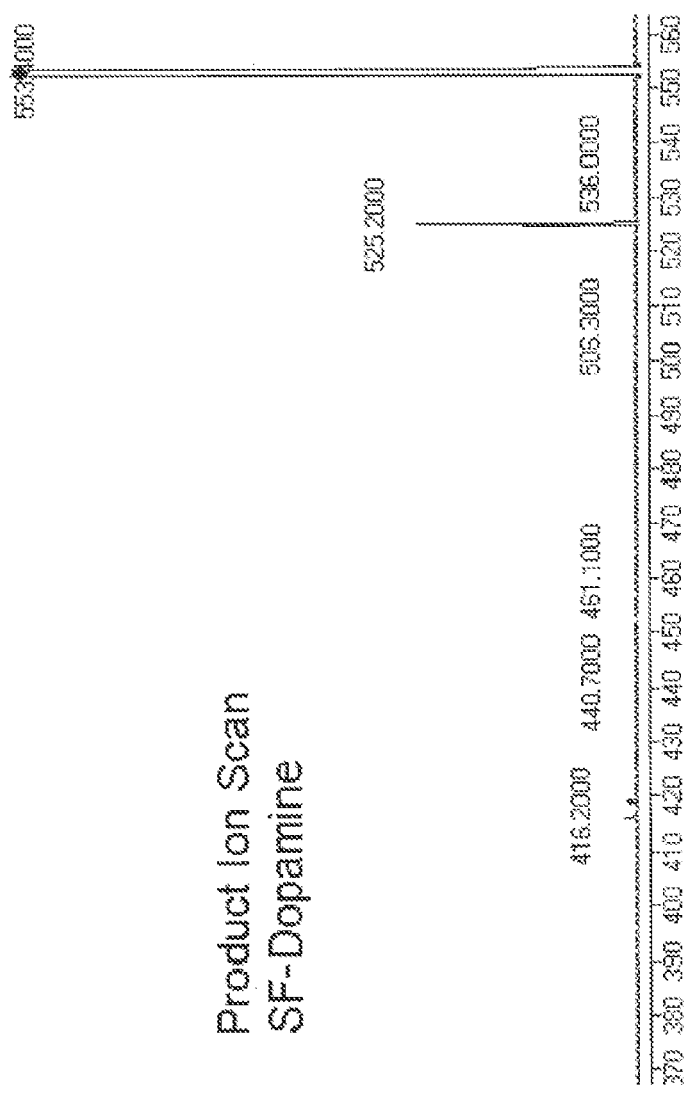

FIG. 16: MS analysis of dopamine using a reactive ester reagent

UHPLC-triple/quadrupole MS spectrum of the dopamine adduct. Clearly visible is the molecule peak at m/z=553 and the N$_2$ loss signal at m/z=525.

Further, the present invention shall be described in more detail by the following Examples:

EXAMPLES

1. Introduction

Base excision repair (BER) is a major DNA maintenance process that allows cells to remove damaged bases from the genome (1, 2). The process requires the action of specific DNA glycosylases, which recognize the non-canonical base (FIG. 3a)(3). Two different types of DNA glycosylases are known. They both catalyze the cleavage of the glycosidic bond to give initially abasic (AP)-site intermediates (step a, FIG. 3a). Mono-functional glycosylases subsequently need endonucleases such as APE-1 (step b, FIG. 3a) to hydrolyse the phosphodiester bonds to create a single strand break. Bi-functional glycosylases in contrast catalyze a β-elimination (βE) reaction (step c, FIG. 3a), which gives a defined βE-intermediate. This βE-intermediate can then be converted into a single nucleotide gap by a subsequent β-elimination reaction (step d, FIG. 3a)(2, 3). BER goes consequently in hand with the formation of single and, if the repaired bases are on opposite strands, also double strand breaks.

Current approaches to measure BER intermediates such as the commercially available aldehyde reactive probe are chemical probes containing an hydroxylamine, which reacts with the open chain aldehydic form of the AP-site (FIG. 3a), and mostly use affinity groups for enrichment and detection. Major drawbacks of these approaches are that in principle the probes react non-selectively with every aldehyde and ketone and that the identity of the derivatized products remains uncharacterized, preventing the distinction between AP- and βE-sites.

Recently it was discovered that BER removes not only damaged bases from the genome, but also the epigenetically relevant bases 5-formyl-cytosine (fdC)(4) and 5-carboxy-cytosine (cadC) can be cleaved by thymine DNA glycosylase (Tdg)(5). Both are formed by oxidation of 5-methyl-cytosine (mdC) via 5-hydroxymethyl-cytosine (hmdC) with the help of β-ketoglutarate dependent Tet oxygenases (FIG. 3b)(5, 6). Although the exact function of the new bases is not known, removal of fdC and cadC seems to be part of a long searched for active demethylation reaction (FIG. 3b).

Here we report the development of a new reagent that in combination with highly sensitive UHPLC-triple quadrupole mass spectrometry and isotope feeding allows exact quantification of AP- and βE-sites with a limit of detection that goes down to 100 intermediates per genome. This new technology allowed us to uncover that both types of intermediates do not accumulate at pyrimidines showing that BER at epigenetic sites is not the expected harmful event in the genome of stem cells.

2. Results and Discussion

The basis for the new technology is reagent 1 (FIG. 3c), which contains a reactive hydroxylamine unit, able to form stable and defined reaction products with both AP-sites and the βE intermediate (7). We showed that the formed adducts (FIG. 3c) do not disturb the action of hydrolytic enzymes (cf. infra) so that the reaction products can be excised from the genome for sensitive mass spectrometric detection and quantification. Importantly, reagent 1 contains a triazole unit that easily fragments in the triple quadrupole MS via collision induced dissociation (CID) to yield intensive daughter ions through the loss of $N_2$. This allows rapid and reliable detection. The permanent positive charge at the quaternary ammonium centre of 1 ensures furthermore highest possible sensitivity and a defined charged state. It also accelerates the reaction with the AP- and βE-sites embedded in the negatively charged DNA duplex.

The synthesis of the reagent is shown in FIG. 4. It started with p-azidoaniline 2, which is reacted with trimethylamino glycine 3 using TBTU (N,N,N',N'-tetramethyl-O-(benzotriazol-1-yl)uronium tetrafluoro-erorate) as the coupling reagent to give the azido-amide 4. A stable isotopologue of reagent 1, needed for the intended exact MS-based quantification (cf. infra), is at this step accessed via a $(CD_3)_3$-glycine derivative allowing the introduction of 9 D-atoms.

O-(Carboxymethyl)hydroxylamine 5 was in parallel Trt (trityl)-protected to $6^8$ and 6 was reacted with propargyl amine using again TBTU as the coupling reagent to give the alkyne 7. Reaction of 4 with 7 via a Cu(I) catalyzed azide-alkyne click reaction furnished the triazole 8. Cleavage of the Trt-group under harsh acidic conditions provided the reagents 1 in a light ($CH_3$, a) and a heavy version ($CD_3$, b), with a Δm/z=9) in just 5 steps with a total yield of 47%. The reagent was purified two times by reversed phase HPLC to ensure purities of >99.9% as needed for the study.

For the planned exact mass spectrometric quantification, the expected AP- and βE-site reaction products were prepared as normal (a) and heavy isotope (b) labelled compounds for the generation of calibration curves and as internal standards. We therefore reacted reagent 1a/b with ribose to obtain the expected AP-site reaction product 9a/b. In order to prepare the needed β-elimination products 10a/b, we reduced the acetonide protected methylester 11 with DIBAL-H to the allyl alcohol, which was selectively oxidized to aldehyde 12 using the Dess-Martin reagent. Reaction of 12 with reagent 1a/b and final cleavage of the acetal protecting group furnished the desired compound 10a/b, again in a light and heavy form, respectively. Compounds 9a/b and 10a/b were finally purified by reversed phase HPLC to purities >99.9%.

We next developed the mass spectrometry based AP- and βE-site detection procedure using an UHPLC-ESI-triple quadrupole (QQQ) machine (FIG. 5). Analysis of the AP-site reaction product 9a showed a clean symmetric signal (at t=9.5 min, for gradient see SI) for the MS transitions m/z=478.2→450.2 (quantifier) and m/z=478.2→192.1 (qualifier) caused by the two molecular fragments formed after the expected $N_2$-loss and the second fragmentation under formation of a arylic radical. The first MS transition (quantifier) was used for the exact quantification of the adducts and the second MS transition (qualifier) was applied for the structure validation. The isotopologue 9b showed the expected mass shifted transitions m/z=487.3→459.2 and m/z=487.3→201.2 at the same retention time. Similarly, high quality data were obtained for the βE-reaction product 10a and its isotopologue 10b (FIG. 5).

We next performed a dilution experiment with the synthetic AP-site reaction product 9a, and monitored the MS-signal. We were able to detect the AP-site 9a/b in the attomolar (LOD of AP-site=110 amol) range. For the quantification of global AP and βE-levels we needed only 5 μg of genomic DNA per sample, which provides a sensitivity that is three orders of magnitude higher compared to previously published methods (9). The sensitivity gained with reagent 1 enabled also the detection of the βE-intermediates formed by bifunctional glycosylases. Here again the detectability extended into the attomolar range (LOD of βE-site=110 amol).

We then started to quantify the intermediates of BER. During embryonic development, BER in combination with the removal of fdC and cadC by the monofunctional DNA glycosylase Tdg was reported to be a major process (4, 5, 10, 11). For the study, naïve cultures of mouse embryonic stem cells (mESCs) were grown under priming conditions (FBS/LIF) conditions for five days. We subsequently isolated genomic DNA using a standard protocol (cf. infra) and incubated it with reagent 1a.

To show that the derivatization reaction of genomic DNA with 1a does not introduce abasic sites artificially and that the quantified levels are endogenous, we added 1a to stem cell DNA and stopped the reaction at several time points using our established protocol (cf. infra). Quantification of the obtained AP-sites in the mixture showed that the reaction was already complete after only one minute and even extended incubation time for up to 60 minutes showed no increase in the amount of abasic sites. Subsequently, the reagent was allowed to react for 40 minutes at 37° C. for further studies to ensure full derivatization of abasic sites. The DNA was afterwards digested with a mixture of nuclease S1, antarctic phosphatase and snake venom phosphodiesterase to the single nucleoside level (cf. infra). In order to ensure that the enzymes are able to fully carve out the reaction products, we prepared DNA with a single dU base, added to the DNA the dU-cleaving glycosylase Udg to introduce a defined abasic site followed by incubation with reagent 1a and quantified the amounts of generated AP-sites (cf. infra). We measured exactly the expected levels of AP-sites, showing that our reagent reacts quantitatively in mild conditions and that the reaction product is completely isolated by the enzymatic digestion protocol.

For exact quantification of the BER intermediates in stem cell DNA we again added 9b and 10b as internal standards after DNA digestion and injected the obtained mixture into the UHPLC-QQQ system. Next to the expected signals from the canonical bases we saw two additional signals from the natural AP- and βE-site reaction products 9a and 10a. This shows that the reagent and the MS method is able to detect and quantify these key BER intermediates directly in genomic DNA.

Exact quantification with the help of the isotope standards 9b and 10b allowed us to determine the global steady state levels of AP- and βE-sites to $8.8 \times 10^{-7}$ and $1.7 \times 10^{-6}$ per dN, respectively. This is a very low level, but due to the high sensitivity of the method it is well within the limits of quantification (cf. infra).

In order to study, if these BER adducts are indeed the endogenously present steady state levels or if the adducts are for example formed during DNA isolation and sample preparation (which is hardly possible for the βE-adducts), we systematically increased the incubation time with the reagent up to one hour. Exact quantification, however, showed no increase of the values arguing against this possibility (cf. infra). We also repeated the study with dU-containing DNA and increased both the incubation time with Udg and the handling time afterwards. We saw no increase of the AP-levels, showing that DNA isolation and handling does not increase the levels of BER intermediates.

Figure 6B:
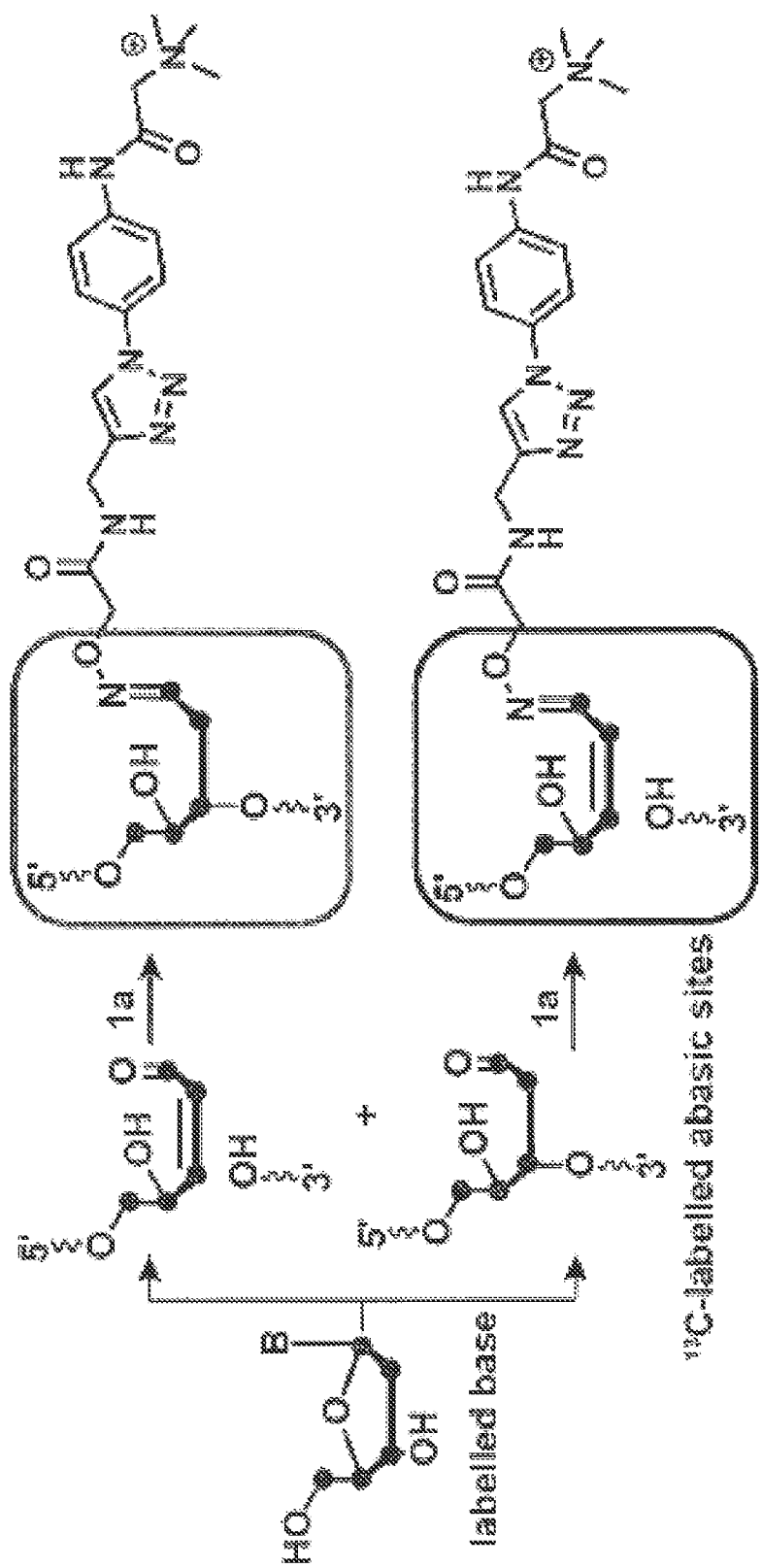
Figure 6C:
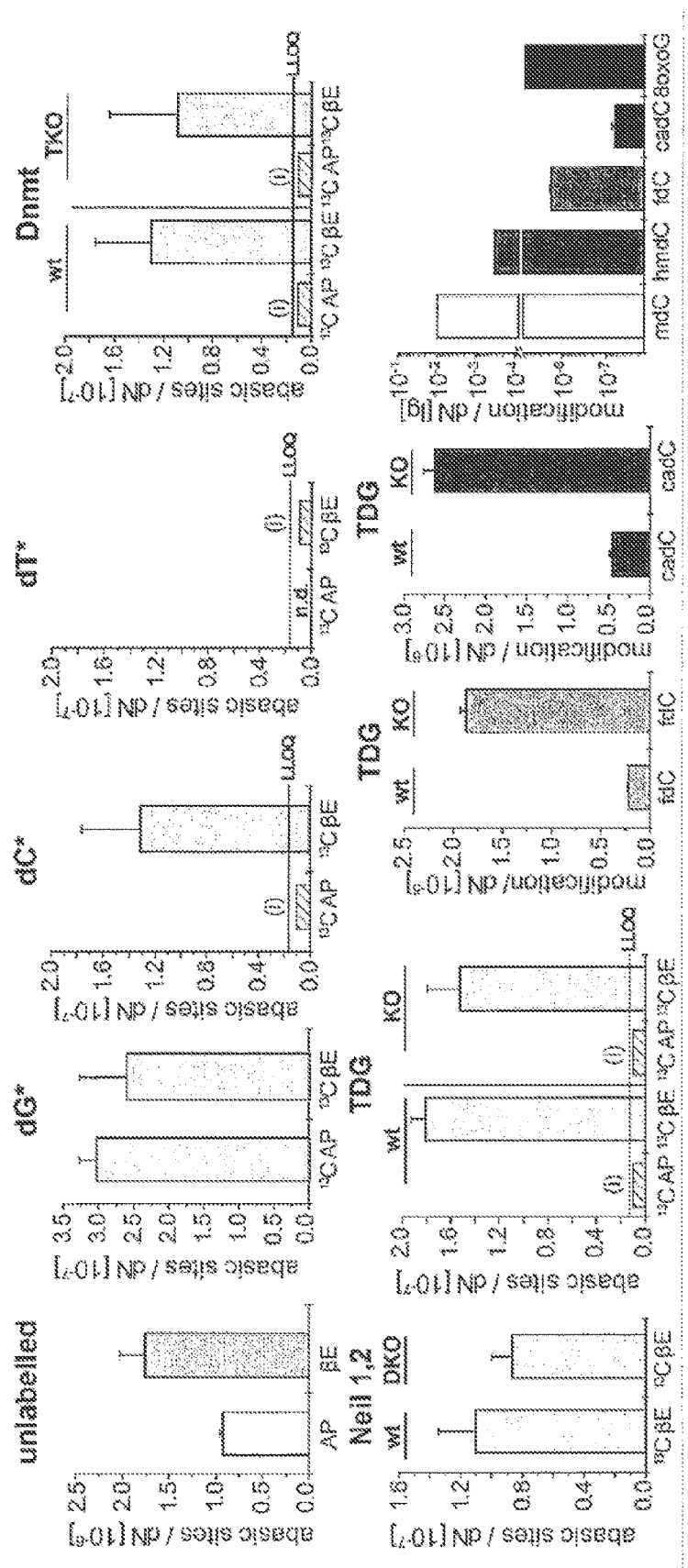

The exact quantification data obtained with genomic DNA show consequently that both βE-sites and AP-sites are present at low steady state levels (FIG. 6c). This confirms constant repair of the genome by both mono- and bifunctional glycosylases. Interestingly we see higher levels of βE-sites, which show either dominant repair by bifunctional glycosylases or that these intermediates have a lower turnover and therefore accumulate to higher steady state levels.

We next wanted to decipher the repair processes at individual DNA bases. To this end we prepared three different mESC cultures and added either isotopically labelled dC*, dG* or dT* nucleosides, in which all the C-atoms of the ribose were exchanged against $^{13}C$ and the in-ring N-atoms against $^{15}N$ as shown in FIG. 6b. BER at these incorporated bases and their derivatives must furnish AP- and βE-reaction products 9* and 10* that are 5 mass units heavier compared to the reaction products 9a and 10a formed at unlabelled AP- or βE-sites and 4 mass units lighter than the internal standards 9b and 10b. First, we monitored the efficiency of incorporation. We saw for $^{13}C_{10}$-dG (dG*) an incorporation of 93%. $^{13}C_9$-dC (dC*) was incorporated to 40% and the $^{13}C_{10}$-dT (dT*) almost fully replaced dT (97% incorporation). Isotopically labelled dA could not be incorporated at levels high enough for subsequent investigation. We next performed exact quantification of the AP- and βE-sites produced at dC*, dG* and dT* and normalized the obtained values to 100% incorporation to get comparable data. The dG base is known to be prone to oxidative damage and the formed lesions are known to be repaired by BER (12, 13). In the dG* experiment we see indeed both AP- and βE-sites (~$2.7 \times 10^{-7}$) at about the same level showing that dG derived base lesions are indeed repaired by BER. Importantly, we see now in contrast to the global data more AP-sites, in full agreement with the idea that the main DNA glycosylase Ogg1 is a bifunctional glycosylase that however has only a slow β-elimination efficiency so that it operates in vivo mostly in combination with APE1 (14, 15).

At dT, which is known to be a rather stable base, both the levels of the AP- and βE-sites are below $10^{-8}$ per dN, which amounts to less than 100 BER intermediates per genome. This level is slightly below the lower level of quantification (LLOQ) (FIG. 6c).

We next studied the BER processes at dC and at epigenetically dC-derived bases. The dC base is known to deaminate to some extend in the genome, which gives dU:dG mismatches (16). In addition, dC is methylated to mdC by DNA methyl transferases (Dnmts), which also deaminates to give dT:dG mismatches (17). Both of these mismatches are known to be repaired by the monofunctional glycosylases Ung2, Smug1, Tdg and Mbd4, which should give detectable AP-sites (18, 19). Furthermore, the dC derivatives fdC and cadC were found to be cleaved by the monofunctional glycosylase Tdg (4, 5). In order to study all these BER events, we fed mESCs, grown under FBS/LIF conditions with 100 μM dC* for 5 days. After DNA isolation, we added reagent 1a, digested the DNA and measured again the levels of labelled AP- and βE-sites. We indeed detected intermediates in contrast to the experiments with dT, but in agreement with the idea that the dC base is less stable due to deamination. Surprisingly, however, we could measure only labelled βE-intermediates generated by bifunctional repair glycosylases, while formation of labelled AP-sites was below LLOQ (FIG. 6c).

This result is in perfect agreement with data from a recent study showing that Tdg might act in a tight complex with the enzymes Neil1-2 (20). The Neil proteins are supposed to bind to the generated AP-sites to catalyse quick β- and δ-elimination reactions in order to keep the steady state levels of AP-sites low and hence bearable.

Further quantification revealed a level of βE-sites at dC* of $1.3 \times 10^{-7}$ per dN. In order to relate the number to the levels of in principle repairable fdC and cadC, we quantified these bases as well. For fdC we measured a level of $2.1 \times 10^{-6}$ and for cadC $1.0 \times 10^{-7}$ was detected. The steady state fdC levels are consequently 1 order of magnitude higher than the βE-site levels, showing that the high levels of fdC do not translate into significant amounts of BER-intermediates, which is in line with the reported stability of fdC.

In order to gain further insight into repair at epigenetic dC sites we studied mESCs lacking either Tdg or both Neil1 and Neil2 proteins and fed both cell lines with dC*. The obtained data are depicted in FIG. 6c. Removing Tdg provides clearly increasing levels of fdC and cadC in agreement with the idea that the protein is involved in the BER based removal. The level of fdC increases by a factor of 10. The cadC level is elevated by a factor of 5. This increase of fdC and cadC does not lead to a substantial change of labelled βE-sites or labelled AP-sites. Surprisingly, even in the experiments with mESC lacking the Neil1/2 proteins, no increase of BER intermediates is observed, suggesting that in this context the Neil proteins do not contribute to β/δ-elimination. We finally studied mESCs lacking the all catalytically active Dnmt proteins so that the mESCs are devoid of mdC, hmdC, fdC and cadC. This too, did not influence the levels of labelled βE sites and no appearance of labelled AP-sites was detected, showing that the quantified βE-sites seen with dC* are all formed directly from dC derived lesions. The data suggest that either BER at xdC sites is of lower importance than so far anticipated or that cells have multiple pathways to control the amount of BER intermediates keeping them at very low steady state levels in order to guarantee that harmful BER intermediates do not accumulate to significant amounts.

3. Conclusion

In conclusion, reagent 1 in combination with a new mass spectrometry based technology (UHPLC-MS) and isotope feeding allows quantification of central BER intermediates at the different canonical bases with unprecedented precision and sensitivity of 100 BER intermediates per genome. Evidence for the BER removal of fdC and cadC in the framework of an active demethylation pathway could not be obtained. Most BER repair processes were detected at dG sites, likely because of oxidative damage at dG.

4. Methods 4.1 Chemical Synthesis Procedures

Unless noted otherwise, all reactions were performed using oven dried glassware under an atmosphere of nitrogen. Molsieve-dried solvents were used from Sigma Aldrich and chemicals were bought from Sigma Aldrich, TCI, Carbolution and Carbosynth. Isotopically labelled trimethylamino glycine was obtained from Eurisotop. For extraction and chromatography purposes, technical grade solvents were distilled prior to their usage. Reaction controls were performed using TLC-Plates from Merck (Merck 60 F254), flash column chromatography purifications were performed on Merck Geduran Si 60 (40-63 μM). Visualization of the TLC plates was achieved through UV-absorption or through staining with Hanessian's stain. NMR spectra were recorded in deuterated solvents on Varian VXR400S, Varian (nova 400, Bruker AMX 600, Bruker Ascend 400 and Bruker Avance III HD. HR-ESI-MS spectra were obtained from a Thermo Finnigan LTQ FT-ICR. IR-measurements were performed on a Perkin Elmer Spectrum BX FT-IR spectrometer with a diamond-ATR (Attenuated Total Reflection) unit. HPLC purifications were performed on a Waters Breeze system (2487 dual array detector, 1525 binary HPLC pump) using a Nucleosil VP 250/10 C18 column from Macherey Nagel, HPLC-grade MeCN was purchased from VWR. For HPLC purifications of compounds 1a/b, 9a/b and 10a/b a buffer system of 0.25 mM ammonium formate in H₂O (referred to as buffer A) and 0.25 mM ammonium formate in 80% MeCN/H₂O (referred to as buffer B) was used.

4.2 Synthesis of Hydroxylamine 1 and Internal Standards 9a/b and 10a/b

4.2.1 (N-Tritylaminooxy)acetic Acid (6)

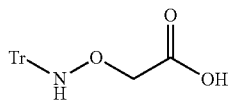

(N-Tritylaminooxy)acetic acid was synthesized according to Kojima et al. (8)

4.2.2 N-(prop-2-ene-1-yl)-2-((tritylamino)oxy)acetamide (7)

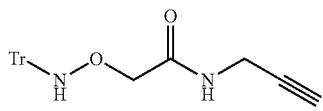

N-trityl protected aminooxyacetic acid 6 (2.50 g, 7.50 mmol, 1.0 eq) was suspended in DCM (40 mL) and was subsequently charged with TBTU (2.89 g, 9.00 mmol, 1.2 eq), DIPEA (1.60 mL, 9.00 mmol, 1.2 eq) and propargylamine (1.40 mL, 22.6 mmol, 3.0 eq). The suspension was stirred at rt (room temperature), whereas after 15 hours a clear yellowish solution was formed. The mixture was diluted with EtOAc (300 mL), the organic phase was washed with NH₄Cl (300 mL) and NaHCO₃ (300 mL) and then dried over Na₂SO₄. Volatiles were finally removed in vacuo and the crude mixture was purified through column chromatography (10% EtOAc-->40% EtOAc/iHex). 7 (2.57 g, 6.93 mmol, 92%) was yielded as a colourless solid.

$^1$H-NMR (300 MHz, CDCl₃): δ/ppm=7.37-7.22 (m, 15H, (C₆H₅)₃C), 6.59 (s, 1H, (C₆H₅)₃C—NH—O), 5.81 (bs, 1H, O=C—NH), 4.25 (s, 2H, O—CH₂C=O), 3.85 (dd, $^3$J=5.5 Hz, $^4$J=2.6 Hz, 2H, HN—CH₂), 2.15 (t, $^4$J=2.6 Hz, 1H, C≡C—H). $^{13}$C-NMR (75 MHz, CDCl₃): δ/ppm=169.1 (C=O), 143.9 (3C, 3×O—NH—C—C), 129.0 (6C, $C_{Ar}$—H), 128.2 (6C, $C_{Ar}$—H), 127.4 (3C, $C_{tert}$—H), 79.3 (C≡C—H), 74.6 (C(C₆H₅)₃), 73.4 (O—CH₂), 71.7 (C≡C—H), 28.8 (NH—CH₂). HRMS (ESI⁺): calc. for C₂₄H₂₂N₂NaO₂ [M+Na]⁺: 393.1573; found: 393.1571. IR (ATR): ṽ (cm⁻¹)=3288 (w), 3222 (w), 3056 (w), 2913 (w), 2359 (w), 2339 (w), 1635 (m), 1542 (m), 1489 (m), 1065 (m), 996 (m), 763 (m), 747 (s), 707 (s), 697 (s), 685 (s), 627 (s). Melting Range: 157-158° C.

4.2.3 2-((4-Azidophenyl)amino-N,N,N-trimethyl-2-oxoethaneaminium Chloride (4a)

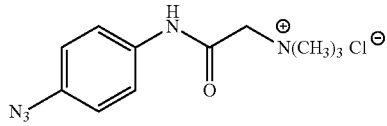

Betaine 3a (0.30 g, 2.56 mmol, 1.0 eq) was first dried on high vacuum at 180° C. for 20 minutes. After cooling to rt, the colourless solid was suspended in DMF (25 mL). 4-Azidoaniline hydrochloride 2 (0.54 g, 3.17 mmol, 1.2 eq), TBTU (0.99 g, 3.07 mmol, 1.2 eq) and DIPEA (1.10 mL, 6.32 mmol, 2.4 eq) were added whereas a yellow brownish solution formed gradually. After stirring for one hour at rt all solids were dissolved and the reaction was further stirred at rt over night. DMF was then removed in vacuo and the crude mixture was purified by column chromatography (DCM/MeOH/H₂O/7N NH₃ in methanol=90:10:0.6:0.6) and 4a was yielded as the corresponding triazolate salt. The salt was then redissolved in H₂O (50 mL) and was acidified to pH=1. The aqueous phase was then extracted with Et₂O until TLC analysis of the organic phase fractions showed no UV absorption anymore. The aqueous layer was then neutralized with conc. NH₃ and the chloride salt of 4a (0.62 g, 2.30 mmol, 90%) was yielded as a brownish powder.

$^1$H-NMR (300 MHz, DMSO d⁶): δ/ppm=11.22 (s, 1H, NH), 7.69 (d, $^3$J=8.9 Hz, 2H, CH=C—NH), 7.12 (d, $^3$J=8.4 Hz, 2H, CH=C—N₃), 4.42 (s, 2H, CH₂), 3.30 (s, 9H, N(CH₃)₃). $^{13}$C-NMR (101 MHz, dmso d⁶): δ/ppm=162.0 (C=O), 135.0 (NH—C=CH), 134.9 (N₃—C=CH), 121.2 (2C, NH—C=CH), 119.5 (2C, N₃—C=CH), 64.3 (CH₂), 53.4 (3C, N(CH₃)₃). HRMS (ESI⁺): calc. for C₁₁H₁₆N₅O⁺ [M⁺]: 234.1349; found: 234.1348. IR (ATR): ṽ (cm⁻¹)=3348 (w), 2983 (w), 2118 (s), 2083 (m), 1692 (s), 1676 (m), 1615 (m), 1549 (m), 1508 (s), 1287 (s), 1256 (m), 1050 (s), 1038 (s), 922 (s), 833 (s). Melting Range: 144-146° C.

4.2.4 N,N,N-trimethyl-2-oxo-2-((4-(4-((2-((tritylamino)oxy)acetamido) methyl)-1H-1,2,3-triazole1-yl)phe-nyl)amino)ethanaminium Chloride/Bromide (8a)

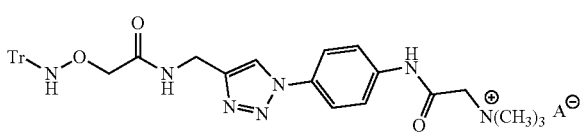

A = Cl, Br

First, a mixture of DCM and H₂O (à 5 mL) was freeze-pump-thaw degassed (3×) and then azide 4a (0.18 g, 0.65 mmol, 1.0 eq), alkyne 7 (0.24 g, 0.65 mmol, 1.0 eq) and CuBr.SMe₂ (40 mg, 0.20 mmol, 0.3 eq) were added. The suspension was stirred vigorously over night at rt whereas a colourless emulsion formed. The mixture was then concentrated under reduced pressure and purified by column chromatography using a short plug of silica (DCM/MeOH/H₂O/7N NH₃ in methanol=80:20:0.6:0.6). 8a was yielded as a slightly yellow brownish solid (0.32 g, 0.50 mmol, 77%).

$^1$H-NMR (300 MHz, DMSO d$^6$): δ/ppm=11.67 (s, 1H, NH—C$_6$H$_4$), 8.55 (s, 1H, CH$_2$—C=CH—N), 8.34 (s, 1H, Ph$_3$C—NH), 8.32 (t, $^3$J=5.8 Hz, 1H, O=C—NH—CH$_2$), 7.91-7.84 (m, 4H, C$_6$H$_4$), 7.34-7.19 (m, 15H, C(C$_6$H$_5$)$_3$), 4.53 (s, 2H, (CH$_2$—N(CH$_3$)$_3$), 4.45 (d, $_3$J=5.8, 2H, NH—CH$_2$), 3.85 (s, 2H, N—O—CH$_2$), 3.33 (s, 9H, N(CH$_3$)$_3$). $^{13}$C-NMR (101 MHz, dmso d$^6$): δ/ppm=169.7 (O=C—NH—CH$_2$), 162.4 (O=C—CH$_2$—N), 146.0 (CH$_2$—C=C), 144.1 (3C, O—NH—C—C), 138.1 (N—C=CH—CH), 132.6 (N—C=CH—CH), 128.9 (6C, C$_{Ar}$—H), 127.6 (6C, C$_{Ar}$—H), 126.7 (3C, C—H), 121.0 (CH$_2$—C=CH—N), 120.5 (4C, N—C=CH—CH=C—N), 73.7 (C(C$_6$H$_6$)$_3$), 73.2 (O—CH$_2$), 64.4 (CH$_2$—N(CH$_3$)$_3$), 53.4 (N(CH$_3$)$_3$), 33.8 (NH—CH$_2$). HRMS (ESI$^+$): calc. for C$_{36}$H$_{38}$H$_7$O$_3$+ [M$^+$]: 604.3031; found: 604.3026. IR (ATR): v˜ (cm$^{-1}$)=3387 (w), 3054 (w), 2923 (w), 1685 (m), 1613 (m), 1558 (m), 1519 (s), 1490 (m), 1446 (m), 1413 (m), 1312 (m), 1265 (m), 1224 (m), 1192 (m), 1085 (m), 1045 (m), 1002 (m), 990 (m), 948 (m), 922 (m), 876 (m), 838 (m), 757 (s), 698 (s), 627 (s). Melting Range: 142-152° C.

4.2.5 2-((4-(4-((2-(Aminooxy)acetoamido)methyl)-1H-1,2,3-triazole-1-yl)phenyl-amino)-N,N,N-trimethyl-2-oxoethanaminium Formate (1a)

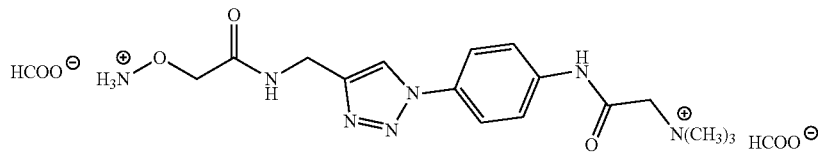

Trityl protected compound 8a (0.24 g, 0.38 mmol) was dissolved in DCM (6 mL) and 6M HCl (6 mL) was added. The mixture was rigorously stirred at rt for one hour until phase separation was visible. The aqueous phase was then extracted with DCM (5×5 mL) until TLC analysis of the organic phase fractions showed no UV absorption anymore. The pH was adjusted to 9-10 using 2M NH$_3$ and the aqueous phase was removed in vacuo. 75 mg of 1a were then further purified by preparative HPLC (0%-->20% buffer B) and yielded 23 mg (0.05 mmol, 26%) of X as the colourless formiate salt.

$^1$H-NMR (400 MHz, D$_2$O): δ/ppm=8.40 (s, 1H, CH$_2$—C=CH—N), 8.21 (s, 1H, HCOO), 7.58 (d, $^3$J=9.2 Hz, 2H, CH—CH=C—N$_3$), 7.52 (d, $^3$J=9.2 Hz, 2H, CH—CH=C—NH), 4.53 (s, 2H, N—O—CH$_2$), 4.27 (s, 2H, NH—CH$_2$), 4.22 (s, 2H, CH$_2$—N(CH$_3$)$_3$), 3.36 (s, 9H, N(CH$_3$)$_3$). $^{13}$C-NMR (101 MHz, D$_2$O): δ/ppm=169.7 (O=C—NH—CH$_2$), 162.4 (O=C—CH$_2$—N), 146.0 (CH$_2$—C=C), 144.1 (3C, O—NH—C—C), 138.1 (N—C=CH—CH), 132.6 (N—C=CH—CH), 128.9 (6C, C$_{Ar}$—H), 127.6 (6C, C$_{Ar}$—H), 126.7 (3C, C—H), 121.0 (CH$_2$—C=CH—N), 120.5 (4C, N—C=CH—CH=C—N), 73.7 (C(C$_6$H$_6$)$_3$), 73.2 (O—CH$_2$), 64.4 (CH$_2$—N(CH$_3$)$_3$), 53.4 (N(CH$_3$)$_3$), 33.8 (NH—CH$_2$). HRMS (ESI$^+$): calc. for C$_{16}$H$_{24}$N$_7$O$_3$$^+$ [M$^+$]: 362.1935; found: 362.1935. IR (ATR): v˜ (cm$^{-1}$)=3130 (m), 3037 (s), 2807 (m), 2649 (m), 2363 (w), 1684 (s), 1610 (m), 1556 (s), 1517 (s), 1487 (m), 1475 (m), 1442 (m), 1403 (s), 1312 (m), 1262 (m), 1193 (m), 1128 (w), 1083 (w), 1048 (m), 991 (m), 967 (w), 921 (s), 837 (s).

4.2.6 N,N,N-Trimethyl-2-oxo-2-((4-(4-((2-((((3S,4R)-3,4,5-trihydroxy-pentyliden)amino)oxy)acetamido)-methyl)-1H-1,2,3-triazol-1-yl)phenyl)-amino)ethanaminium Formate (9a)

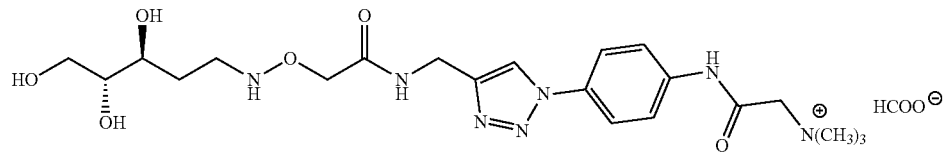

1a (50.0 mg, 0.12 mmol, 1-0 eq) and 2'-desoxyribose (182 mg, 1.36 mmol, 11.8 eq) were dissolved in H$_2$O (2.7 mL) and incubated over night at 30° C. and 1400 rpm in a Eppendorf comfort thermomixer. The mixture was filtered over a 0.2 μm syringe filter and was subsequently purified by HPLC twice (0-->15% buffer B). Pure product 9a (9.1 mg, 17 μmol, 15%) was obtained as a colourless foam. The compound was present as a mixture of E/Z isomers in aqueous solution that were not assigned.

$^1$H-NMR (600 MHz, D$_2$O): δ/ppm=8.46 (s, 1H, HCOO), 8.34 (s, 1H, CH$_2$—C=CH—N), 7.79 (d, J=9.0 Hz, 2H, CH—CH=C—N$_3$), 7.74-7.71 (m, 8H, CH—CH=C—NH, C1'—H$^A$), 7.08 (t, $^3$J=5.4 Hz, 1H, C1'—H$^B$), 4.67 (s, 2H, NO—CH$_2$$^B$), 4.63 (s, 2H, NH—CH$_2$), 4.62 (s, 2H, N—O—CH$_2$$^A$), 4.35 (s, 2H, CH$_2$—N(CH$_3$)$_3$), 3.92-3.87 (m, 1H, C3'-H$^B$), 3.85-3.80 (m, 1H, C3'—H$^A$), 3.78-3.69 (m, 1H, C5'-H), 3.66-3.53 (m, 2H, C5'-H, C4'-H), 3.42 (s, 9H, N(CH$_3$)$_3$), 2.79-2.69 (m, 2H, C2'-H$^B$), 2.58-2.54 (m, 1H, C2'-H$^A$), 2.41-2.35 (m, 1H, C2'-H$^A$). $^{13}$C-NMR (150 MHz, D$_2$O): δ/ppm=172.4 (O=C—NH—CH$_2$), 170.9 (HCOO), 162.7 (O=C—CH$_2$—N), 153.5 (C1'$^A$), 153.1 (C1'$^B$), 145.1 (CH$_2$—C=C), 136.8 (N—C=CH—CH), 133.5 (N—C=CH—CH), 122.5 (2C, CH=C—NH), 122.3 (CH$_2$—C=CH—N), 121.9 (2C, CH=C—N$_3$), 74.2 (C4'), 74.0 (C4'), 71.7 (NO—CH$_2$$^B$), 71.5 (N—O—CH$_2$$^A$), 69.0 (C3'$^A$), 68.8 (C3'$^B$), 65.1 (CH$_2$—N(CH$_3$)$_3$), 62.3 (C5'), 54.3 (N(CH$_3$)$_3$), 34.1 (NH—CH$_2$), 32.4 (C$_2$·A), 29.2 (C2'B). HRMS (ESI$^+$): calc. for C$_{21}$H$_{32}$N$_7$O$_6$+[M]+: 478.2409; found: 478.2404.

4.2.7 (S,E)-3-(2,2-Dimethyl-1,3-dioxolan-4-yl)acrylaldehyd (12)

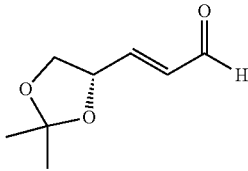

Methyl (2E)-3-[(4S)-2,2-dimethyl-1,3-dioxolan-4-yl] prop-2-enoate 11 (0.20 g, 1.08 mmol, 1.0 eq) was dissolved in DCM (2.0 mL) and cooled to −78° C. DIBAL-H (diisobutylaluminium hydride) (2.20 mL, 2M in toluene, 2.1 eq) was added and the yellowish mixture was slowly warmed to rt. After 90 minutes, DCM (5.0 mL) and $H_2O$ (4.0 mL) and NaOH (2M, 2.0 mL) were added. After stirring for an additional hour at rt, the organic phase was separated from the aqueous and dried over $Na_2SO_4$. Volatiles were removed under reduced pressure and the allylic alcohol was yielded in quantitative yield and used without further purification.

$^1$H-NMR (400 MHz, $CDCl_3$): δ/ppm=5.88 (dt, $^3J$=15.4 Hz, $^4J$=5.0 Hz, 1H, 5'-H) 5.65 (dd, $^3J$=15.6 Hz, $^4J$=7.6 Hz, 1H, 5'-H), 4.47 (q, $^3J$=7.3 Hz, 1H, 4'-H), 4.08 (d, $^3J$=5.1 Hz, 2H, 1'-H), 4.30 (dd, $^3J$=8.2 Hz, $^4J$=6.1 Hz, 1H, 3'-H), 3.53 (t, $^3J$=7.9 Hz, 1H, 2'-H), 2.34 (br s, 1H, $CH_2$—OH), 1.36 (s, 3H, O—C($CH_3$)($CH_3$)—O), 1.32 (s, 3H, O—C($CH_3$)($CH_3$)—O).

The allylic alcohol was dissolved in DCM (2.0 mL) and cooled to 0° C. and was charged with Dess-Martin-periodinan (0.45 g, 1.08 mmol, 1.0 eq). The milky suspension was slowly warmed to rt and stirred over night. After the addition of saturated $Na_2SO_4$ (10 mL) and a solution of $Na_2S_2O_3$ (171 mg, dissolved in 10 mL $H_2O$), the mixture was extracted with DCM (3×15 mL) and dried over $Na_2SO_4$. Organic solvents were removed in vacuo and the crude mixture was purified via column chromatography (2.5% MeOH/DCM). Aldehyde 12 (80 mg, 0.51 mmol, 47%) was isolated as a colourless oil.

$^1$H-NMR (400 MHz, $CD_2Cl_2$): δ/ppm=9.50 (d, $^3J$=7.6 Hz, 1H, 1'-CHO), 6.70 (dd, $^3J$=15.6 Hz, $^4J$=5.3 Hz, 1H, 3'-H), 6.23 (dt, $^3J$=15.6 Hz, $^4J$=5.8 Hz, 1H, 2'-H), 4.73 (q, $^3J$=6.8 Hz, 1H, 4'-H), 4.18 (dd, $^3J$=8.4 Hz, $^4J$=6.8 Hz, 1H, 5'-H), 3.67 (dd, $^3J$=8.4 Hz, $^4J$=6.8 Hz, 1H, 5'-H), 1.39 (s, 3H, O—C($CH_3$)($CH_3$)—O), 1.35 O—C($CH_3$)($CH_3$)—O). $^{13}$C-NMR (101 MHz, $CD_2Cl_2$): δ/ppm=193.0 (—CHO), 153.4 (3'-C), 132.1 (2'-C), 110.3 (C), 74.9 (4'-C), quart, 68.7 (5'-C), 26.2 (O—C($CH_3$)($CH_3$)—O), 25.4 (O—C($CH_3$)($CH_3$)—O). HRMS (EI): calc. for $C_8H_{11}O_3$. [M-H]': 155.0708; found: 155.0707.

4.2.8 2-((4-(4-((2-(((((1E,2E)-3-((S)-2,2-Dimethyl-1,3-dioxolane-4-yl)-allylidene)-amino)oxy)acetamido)me-thyl)-1H-1,2,3-triazole-1-yl)phenyl)-amino)-N,N,N-trimethyl-2-oxoethane-1-aminium Formate (10a)

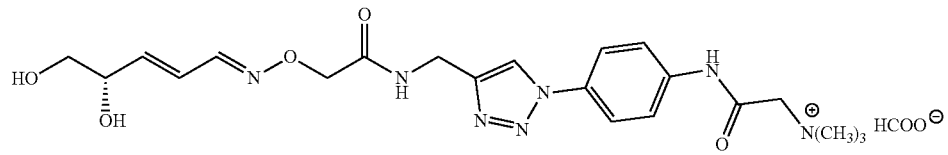

Aldehyde 12 (20 mg, 0.13 mmol, 9.0 eq) was dissolved together with hydroxylamine 1a in a 1:1 mixture of $H_2O$ and $CHCl_3$ (à 2.5 mL) and was stirred at rt. The course of the reaction was monitored by HPLC (0-->30% buffer B) whereas it was determined that after one hour the reaction was done. The aqueous phase was then washed with DCM (3×10 mL) and concentrated in vacuo. 13a (5.10 mg, 9.50 μmol, 68%) was yielded as a brownish viscous oil that was used without further purification.

$^1$H-NMR (400 MHz, $D_2O$): δ/ppm=8.31 (s, 1H, HCOO), 8.12 (s, 1H, $CH_2$—C=CH—N), 7.84 (d, 1H, 1'-H), 7.59-7.53 (m, 4H, CH—CH=C—$N_3$, CH—CH=C—NH), 6.20-6.03 (m, 2H, 2'+3'-H's), 4.54-4.52 (m, 1H, 4'-H), 4.50 (s, 2H, NO—$CH_2$), 4.47 (s, 2H, NH—$CH_2$), 4.20 (s, 2H, $CH_2$—N($CH_3$)$_3$), 4.02-3.98 (m, 1H, 5'-H), 3.45-3.50 (m, 1H, 5'-H), 3.27 (s, 9H, $CH_2$—N($CH_3$)$_3$), 1.26 (s, 3H, O—C($CH_3$)($CH_3$)—O), 1.24 (s, 3H, O—C($CH_3$)($CH_3$)—O). HRMS (ESI$^+$): calc. for $C_{24}H_{34}N_7O_5$+[M$^+$]: 500.2616; found: 500.2617.

Deprotection of acetonide 13a (4.00 mg, 7.50 μmol, 1.0 eq) was dissolved in MeOH and $PTSA.H_2O$ (1.40 mg, 7.50 μmol, 1.0 eq) was added. The mixture was incubated in a Eppendorf comfort thermomixer (1300 rpm, 25° C.) over night and the solvent was removed in vacuo by lyophylization. The crude product was finally purified by preparative HPLC (0-->35% buffer B in 45 minutes) and pure 10a was yielded as a colourless foam.

$^1$H-NMR (400 MHz, $D_2O$): δ/ppm=8.53 (s, 1H, HCOO), 8.30 (s, 1H, $CH_2$—C=CH—N), 8.01 (s, d, $^3J$=8.9 Hz, 1H, 1'-H), 7.78-7.70 (m, 4H, CH—CH=C—$N_3$, CH—CH=C—NH), 6.31-6.32 (m, 2H, 2'+3'-H's), 4.63 (s, 2H, N—O—$CH_2$), 4.62 (s, 2H, NH—$CH_2$), 4.35-4.32 (m, 3H, $CH_2$—N($CH_3$)$_3$+4'-H), 3.61 (dd, $^1J$=11.7 Hz, $^3J$=4.4, 1H, 5'-H), 3.51 (dd, $^1J$=11.7 Hz, $^3J$=6.5, 1H, 5'-H), 3.22 (s, 9H, $CH_2$—N($CH_3$)$_3$). $^{13}$C-NMR (101 MHz, $D_2O$): 15/ppm=172.3 (O=C—NH—$CH_2$), 170.9 (HCOO), 162.7 (O=C—$CH_2$—N), 153.7 (1'-C), 144.5 ($CH_2$—C=C), 142.8 (3'-C), 136.9 (N—C=CH—CH), 133.6 (N—C=CH—CH), 123.0 (2'-C), 122.5 (2C, CH=C—NH), 122.3 ($CH_2$—C=CH—N), 122.0 (2C, CH=C—$N_3$), 72.0, (N—O—$CH_2$) 71.6 (4'-C), 64.4 (5'-C), 65.1 ($CH_2$—N($CH_3$)$_3$), 54.3 (N($CH_3$)$_3$), 34.1 (NH—$CH_2$). HRMS (ESI$^+$): calc. for $C_{21}H_{30}N_7O_5^+$ [M]$^+$: 460.2303; found: 460.2305.

4.2.9 2-((4-Azidophenyl)amino-N,N,N-tri(methyl-d3)-2-oxoethaneaminium Chloride (4b)

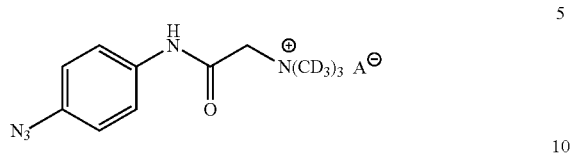

A = Cl, Br 4b was synthesized analogous to 4a whereas [$d_{11}$]-betaine (98% deuterium, Euriso-Top GmbH) was used to introduce isotopic labels. Deuterium labels from the methylene group were not stable under the reaction conditions and a complete D/H exchange was observed. Thus, a [$d_9$]-labelled product was obtained.

$^1$H-NMR (600 MHz, D$_2$O): δ/ppm=7.39 (d, $^3$J=8.6, 2H, CH—CH=C—NH), 7.04 (d, $^3$J=8.5, 2H, CH—CH=C—N$_3$), 4.18 (s, 2H, CH$_2$). $^{13}$C-NMR (150 MHz, D$_2$O, ppm): δ/ppm=162.7 (C=O), 137.5 (NH—C=CH), 132.5 (N$_3$—C=CH), 123.5 (2C, NH—C=CH), 119.6 (2C, N$_3$—C=CH), 65.0 (CH$_2$). HRMS (ESI$^+$): calc. for C$_{11}$H$_7$D$_9$N$_5$O$^+$ [M]$^+$: 243.1914; found: 243.1916.

4.2.10 2-((4-(4-((2-(Aminooxy)acetoamido)methyl)-1H-1,2,3-triazole-1-yl)phenyl-amino)-N,N,N-tri(methyl-d3)-2-oxoethanaminium Formate (1b)

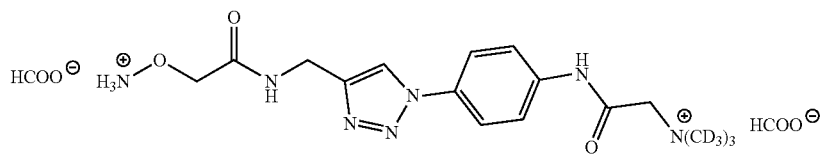

Isotopologue 1b was synthesized according to 1a with the slight modification that the trityl protected intermediate 8b was not isolated and deprotected without further purification.

4.2.11 N,N,N-Tri(methyl-d3)-2-oxo-2-((4-(4-((2-((((3S,4R)-3,4,5-trihydroxy-pentyliden)amino)oxy)acet-amido)-methyl)-1H-1,2,3-triazol-1-yl)phenyl)-amino)ethanaminium Formate (9b)

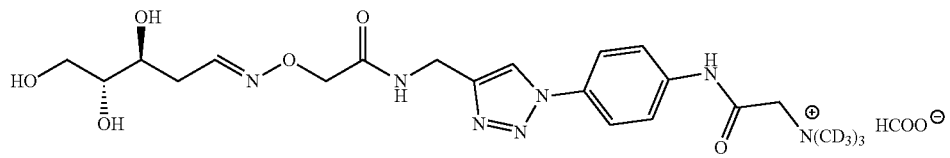

Internal standard 9b was synthesized analogous to 9a, whereas a mixture of (E)/(Z)-isomers was obtained (depicted as A and B).

$^1$H-NMR (600 MHz, D$_2$O): δ/ppm=8.46 (s, 2H, HCOO), 8.35 (s, 1H, CH$_2$—C=CH—N), 7.81 (d, $^3$J=7.5 Hz, 2H, CH—CH=C—N$_3$), 7.75-7.73 (m, 8H, CH—CH=C—NH, C1'-H$^A$), 7.08 (t, $^3$J=5.4 Hz, 0.1H, C1'-H$^B$), 4.67 (s, 2H, N—O—CH$_2^B$), 4.64 (s, 2H, NH—CH$_2$), 4.62 (s, 2H, N—O—CH$_2^A$), 4.34 (s, 2H, CH$_2$—N(CH$_3$)$_3$), 3.93-3.87 (m, 1H, C3'-H$^B$), 3.86-3.79 (m, 1H, C3'-H$^A$), 3.78-3.69 (m, 1H, 1×C5'-H$_2$), 3.67-3.53 (m, 2H, 1×C5'-H$_2$, C4'-H), 2.80-2.68 (m, 2H, C2'-H$_2^B$), 2.59-2.54 (m, 1H, C2'-H$^A$), 2.43-2.34 (m, 1H, C2'-H$^A$). $^{13}$C-NMR (150 MHz, D$_2$O, ppm): δ/ppm=172.4 (O=C—NH—CH$_2$), 170.9 (HCOO), 162.8 (O=C—CH$_2$—N), 153.5 (C1'$^A$), 153.1 (C1'$^B$), 145.1 (CH$_2$—C=C), 136.8 (N—C=CH—CH), 133.6 (N—C=CH—CH), 122.6 (2C, CH=C—NH), 122.4 (CH$_2$—C=CH—N), 122.0 (2C, CH=C—N$_3$), 74.2 (C4'), 74.0 (C4'), 71.7 (N—O—CH$_2^B$), 71.5 (N—O—CH$_2^A$), 69.0 (C3'$^A$), 68.8 (CP), 64.9 (CH$_2$—N(CD$_3$)$_3$), 62.3 (05'), 53.3 (N(CD$_3$)$_3$), 34.1 (NH—CH$_2$), 32.4 (C2'A), 29.2 (C2'B). HRMS (ESI$^+$): calc. for C$_{21}$H$_{23}$D$_9$N$_7$O$_6^+$ [M]$^+$: 487.2973; found: 487.2967.

4.2.12 2-((4-(4-((2-((((1E,2E)-3-((S)-2,2-Dimethyl-1,3-dioxolane-4-yl)-allylidene)-amino)oxy)acetamido)me-thyl)-1H-1,2,3-triazole-1-yl)phenyl)-amino)-N,N,N-tri(methyl-d3)-2-oxoethane-1-aminium Formate (10b)

1000 U/mL LIF (ORF Genetics), 3.0 μM GSK3 inhibitor CHIR99021 and 1.0 μM Mek inhibitor PD0325901 (2i; Selleckchem). Metabolic labelling experiments with isotope-labelled nucleosides were performed by plating mESCs in priming conditions, consisting of basal mESC medium supplemented with 1000 U/mL LIF. Labelled nucleosides (B.A.C.H. UG) were added to the culture medium at the following concentrations: dG [$^{15}$N$_5$;$^{13}$C$_{10}$], 100 μM for three days, followed by treatment with 200 μM labelled dG for two days; dC [$^{15}$N$_3$;$^{13}$C$_9$] and dT [$^{15}$N$_2$;$^{13}$C$_{10}$] were both used at a concentration of 100 μM for five days in total. Dnmt TKO J1 mESCs were described in Tsumura et al. (21). and J1 wild type mESCs were obtained from the 12954/SvJae strain (22). For Tdg+/− and the Tdg−/− cell lines reported in Cortazar et al. (11) were used.

4.4 Cell Lysis and DNA Isolation

Isolation of genomic DNA was achieved using the QIAamp DNA Mini Kit from Qiagen. All mESC samples were washed with PBS (Sigma) and directly lysed in the plates by adding G2 buffer containing 400 μM of 2,6-di-tert-butyl-4-methylphenol (BHT) and desferoxamine mesylate (DM). DNA was sheared by bead milling in a microfuge tube using one 5 mm diameter stainless steel bead per tube and MM400 bead mill (Retsch) at 30 Hz for for one minute and subsequently centrifuged at 15000 rpm for ten minutes. Depending on the amount of genomic DNA to isolate, the cell lysate was treated with proteinase K (25 μL for genomic tips 20G or 100 μL for genomic tips 100G) and RNase A (2.0

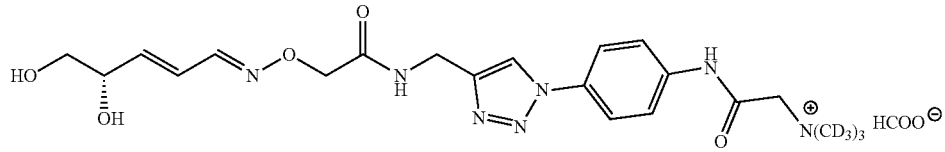

10b was synthesized according to 10a.

$^1$H-NMR (800 MHz, D$_2$O): δ/ppm=8.47 (s, 1H, HCOO), 8.32 (s, 2H, CH$_2$—C=CH—N), 8.02 (d, $^3$J=9.4 Hz, 1H, 1'-H), 7.80-7.71 (m, 4H, CH—CH=C—N$_3$, CH—CH=C—NH), 6.34-6.26 (m, 2H, 2'+3'-H's), 4.65 (s, 2H, N—O—CH$_2$), 4.63 (s, 2H, NH—CH$_2$), 4.35-4.32 (m, 3H, CH$_2$—N(CH$_3$)$_3$+4'-H), 3.63 (dd, $^1$J=11.7 Hz, $^3$J=4.4, 1H, 5'-H), 3.53 (dd, $^1$J=11.7 Hz, $^3$J=6.5, 1H, 5'-H). $^{13}$C-NMR (150 MHz, D$_2$O): δ/ppm=172.3 (O=C—NH—CH$_2$), 170.9 (HCOO), 162.8 (O=C—CH$_2$—N), 153.7 (1'-C), 145.2 (CH$_2$—C=C), 142.8 (3'-C), 136.9 (N—C=CH—CH), 133.6 (N—C=CH—CH), 123.0 (2'-C), 122.5 (2C, CH=C—NH), 122.3 (CH$_2$—C=CH—N), 122.0 (2C, CH=C—N$_3$), 72.1 (N—O—CH$_2$) 71.6 (4'-C), 64.4 (5'-C), 65.1 (CH$_2$—N(CH$_3$)$_3$), 53.3 (N(CD$_3$)$_3$), 34.1 (NH—CH$_2$). HRMS (ESI$^+$): calc. for C$_{21}$H$_{21}$D$_9$N$_7$O$_5^+$ [M]$^+$: 469.2868; found: 469.2874.

4.3 Cell Culture

DMEM high glucose containing 10% FBS (PAN Biotech), 2 mM L-glutamine, 100 U/mL penicillin, 100 μg/mL streptomycin, 1×MEM Non-essential Amino Acid Solution and 0.1 mM β-mercaptoethanol (Sigma Aldrich) was used as basal medium for mESC (mouse embryonic stem cell) cultures. The mESC lines were maintained in naïve state on gelatin coated plates by supplementing basal medium with μL/20G, 10 μL/100G) at 50° C. for one hour. After 30 minutes, additional RNase A (2.0 μL or 10 μL, respectively) was added to the mixture. Genomic tip columns were then equilibrated with loading buffer QBT (1.0 mL/20G or 4.0 mL/100G) and the lysate, which was vortexed for one minute, was applied on the columns. After the entire liquid had entered the column, washing steps were carried out with buffer QC (2.0 mL/20G or 2×7.5 mL/100G) and the genomic DNA was finally eluted with QF buffer (2.0 mL/20G or 5.0 mL/100G) supplemented with 400 μM BHT (butylated hydroxyl-toluene). Precipitation was then achieved through addition of i-PrOH (1.4 mL/20G or 3.5 mL/100G, 70% Vol) and the resulting genomic DNA pellet was centrifuged (15 minutes, 6000 g, 4° C.). The supernatant was discarded washing steps were carried out using 70% EtOH (5.0 mL, 15 minutes, 6000 g, 4° C.). Finally, the pure DNA pellet was resuspended in 1.0 mL 70% EtOH and centrifuged (10 minutes, 15000 rpm, 4° C.). Next, the supernatant was removed and the pellet was re-dissolved in ddH$_2$O (50-100 μL) with 20 μM BHT. The concentration was determined with a NanoDrop (ND 1000, Peqlab).

4.5 Derivatization of Genomic DNA with 1a

Derivatization of abasic sites (5.0 μg for unlabelled gDNA, 20 μg for labelled gDNA) with 1 was carried out in a total volume of 20 μL, whereas the solution was buffered with HEPES (20 mM, pH=7.5) and Na$_2$EDTA (0.1 mM). A stock of 1 in H$_2$O (23.8 mM) was added to the buffered solution (final concentration of 1=1.5 mM) and the reaction was started by vortexing the mixture for 5 seconds. The gDNA was incubated for 40 minutes at 37° C./1400 rpm in an Eppendorf comfort thermomixer. The reaction was stopped through addition of 1-naphthylaldehyde (66.7 µL, 2M in i-PrOH) to quench excess of 1 and incubated again for 10 minutes at 37° C./1400 rpm. Derivatized DNA was then precipitated through addition of NaOAc (3.3 µL, 3M), vortexing and incubation at 37° C./1400 rpm for another 5 minutes. Absolute i-PrOH (66.7 µL) was added, the tubes were inverted several times and then centrifuged (60 minutes, 10° C., 15000 rpm). The supernatant was removed and washing steps were carried out (1×75% i-PrOH, 10° C., 15000 rpm, 30 minutes; 2×75% cold EtOH, 4° C., 15000 rpm, 30 minutes), whereas after each washing step the supernatant was carefully removed. The resulting DNA pellet was finally re-dissolved in 35 µL of ddH$_2$O and then enzymatically digested to the nucleoside level.

4.6 Enzymatic Digestion of Derivatized Genomic DNA

For enzymatic digestion of genomic DNA (5.0 µg for unlabeled gDNA or 20 µg for labelled gDNA in 35 µL H$_2$O) we used an aqueous solution of 480 µM ZnSO$_4$ and incubated the mixture at 37° C. for 3 h. The solution consisted of 5 U Antarctic phosphatase (New England BioLabs), 42 U nuclease S1 (*Aspergillius oryzae*, Sigma-Aldrich) and specific amounts of labeled internal standards for accurate quantification of DNA-modifications and derivatised abasic sites. In the second digestion round we added 0.2 U snake venom phosphodiesterase I (*Crotalus adamanteus*, USB corporation) in 7.5 µl of a 520 µM [Na]$_2$-EDTA and incubated the mixture further 3 h or overnight at 37° C. After digestion, the sample was stored at −20° C. and filtered by using an AcroPrep Advance 96 filter plate 0.2 µm (0.20 µm Supor, Pall Life Sciences) before LC-MS/MS analysis (39 µg injection volume at 4° C.).

4.7 LC-ESI-MS/MS Analysis of DNA Samples

For the LC-MS/MS studies we used triple quadrupole mass spectrometer Agilent 6490 and Agilent 1290 UHPLC system with an UV detector. Based on earlier published work (23-27), we developed a new method and coupled it with isotope dilution technique, which allowed us exact quantification of derivatized abasic sites, all canonical nucleoside and cytosine modifications in one single analytical run.

The chromatographical separation was performed over a Poroshell 120 SB-C8 column (Agilent, 2.7 µm, 2.1 mm×150 mm). Eluting buffers were water and MeCN, each containing 0.0085% (v/v) formic acid, at a flow rate of 0.35 ml/min at 30° C. The gradient was: 0→5 min; 0→3.5% (☐/☐) MeCN, 5→6.9 min; 3.5→5% MeCN, 6.9→13.2 min; 5→80% MeCN, 13.2→14.8 min; 80% MeCN; 14.8→15.3 min; 80→0% MeCN, 15.3→17 min; 0% MeCN. The eluent up to 1.5 min and after 12.2 min was diverted to waste by a Valco valve.

By the direct injection of synthesized internal standards we optimized the source-dependent parameters, which were as follow: gas temperature 50° C., gas flow 15 l/min (N$_2$), nebulizer 30 psi, sheath gas heater 275° C., sheath gas flow 11 l/min (N$_2$), capillary voltage 2500 V (positive mode) and −2250 V (negative ion mode), nozzle voltage 500 V, the fragmentor voltage 380 V, Δ EMV 500 (positive mode) and 800 (negative mode). Compound-dependent parameters which gave highest intensities during method development are summarized in Table 1.

TABLE 1

Compound-dependent LC-MS/MS-parameters used for the analysis of genomic DNA. CE: collision energy, CAV: collision cell accelerator voltage, EMV: electron multiplier voltage. The nucleosides were analyzed in the positive ([M + H])$^+$ species) as well as the negative ([M − H]$^-$ species) ion selected reaction monitoring mode (SRM).

| compound | Precursor ion (m/z) | MS1 Resolution | Product ion (m/z) | MS2 Resolution | Dwell time [ms] | CE (V) | CAV (V) | Polarity |
|---|---|---|---|---|---|---|---|---|
| Time segment 1.5-4.0 min | | | | | | | | |
| [$^{15}$N$_2$]5cadC | 274.08 | wide | 158.03 | wide | 170 | 5 | 5 | Positive |
| 5cadC | 272.09 | wide | 156.04 | wide | 170 | 5 | 5 | Positive |
| [$^{15}$N$_2$, D$_2$]5hmdC | 262.12 | enhanced | 146.07 | enhanced | 40 | 27 | 1 | Positive |
| 5hmdC | 258.11 | enhanced | 142.06 | enhanced | 40 | 27 | 1 | Positive |
| [D$_3$]5mdC | 245.13 | enhanced | 129.09 | enhanced | 30 | 60 | 1 | Positive |
| 5mdC | 242.11 | enhanced | 126.07 | enhanced | 30 | 60 | 1 | Positive |
| dC | 228.12 | enhanced | 112.05 | enhanced | 25 | 5 | 5 | Positive |
| [$^{13}$C$_9$, $^{15}$N$_3$]dC | 240.12 | enhanced | 119.06 | enhanced | 25 | 5 | 5 | Positive |
| Time segment 4.0-5.5 min | | | | | | | | |
| [D$_2$]5hmdU | 259.09 | wide | 216.08 | wide | 48 | 7 | 5 | Negative |
| 5hmdU | 257.08 | wide | 214.07 | wide | 48 | 7 | 5 | Negative |
| [$^{15}$N$_2$]5fdU | 257.06 | wide | 213.05 | wide | 48 | 6 | 5 | Negative |
| 5fdU | 255.06 | wide | 212.06 | wide | 48 | 6 | 5 | Negative |
| Time segment 5.5-8.1 min | | | | | | | | |
| [$^{15}$N$_5$]8oxodG | 289.08 | wide | 173.04 | wide | 90 | 9 | 7 | Positive |
| 8oxodG | 284.1 | wide | 168.05 | wide | 90 | 9 | 7 | Positive |
| dG | 268.1 | wide | 152.06 | wide | 75 | 45 | 3 | Positive |
| [$^{13}$C$_{10}$, $^{15}$N$_5$] dG | 283.12 | wide | 162.06 | wide | 75 | 45 | 3 | Positive |
| [$^{15}$N$_2$]5fdC | 258.09 | wide | 142.04 | wide | 50 | 5 | 5 | Positive |
| 5fdC | 256.09 | wide | 140.05 | wide | 50 | 5 | 5 | Positive |

TABLE 1-continued

Compound-dependent LC-MS/MS-parameters used for the analysis of genomic DNA. CE: collision energy, CAV: collision cell accelerator voltage, EMV: electron multiplier voltage. The nucleosides were analyzed in the positive ($[M + H]^+$ species) as well as the negative ($[M - H]^-$ species) ion selected reaction monitoring mode (SRM).

| compound | Precursor ion (m/z) | MS1 Resolution | Product ion (m/z) | MS2 Resolution | Dwell time [ms] | CE (V) | CAV (V) | Polarity |
|---|---|---|---|---|---|---|---|---|
| Time segment 8.1-12.2 min | | | | | | | | |
| 1-Naphthyl-Oxime | 500.24 | wide | 472.23 | wide | 5 | 19 | 5 | Positive |
| 9b_1 | 487.3 | wide | 459.29 | wide | 38 | 19 | 5 | Positive |
| 9b_2 | 487.3 | wide | 201.18 | wide | 38 | 40 | 5 | Positive |
| [$^{13}C_5$]9a_1 | 483.26 | wide | 455.25 | wide | 38 | 19 | 5 | Positive |
| [$^{13}C_5$]9a_2 | 483.26 | wide | 192.13 | wide | 38 | 40 | 5 | Positive |
| 9a_1 | 478.24 | wide | 450.23 | wide | 38 | 19 | 5 | Positive |
| 9a_2 | 478.24 | wide | 192.13 | wide | 38 | 40 | 5 | Positive |
| 10b_1 | 469.29 | wide | 441.28 | wide | 38 | 19 | 3 | Positive |
| 10b_2 | 469.29 | wide | 201.18 | wide | 38 | 33 | 3 | Positive |
| [$^{13}C_5$]10a_1 | 465.23 | wide | 437.22 | wide | 38 | 20 | 3 | Positive |
| [$^{13}C_5$]10a_2 | 465.23 | wide | 192.13 | wide | 38 | 34 | 3 | Positive |
| 10a_1 | 460.23 | wide | 432.22 | wide | 38 | 20 | 3 | Positive |
| 10a_2 | 460.23 | wide | 192.13 | wide | 38 | 34 | 3 | Positive |
| 1b | 371.25 | wide | 343.24 | wide | 5 | 19 | 5 | Positive |
| 1a | 362.19 | wide | 334.19 | wide | 5 | 19 | 5 | Positive |
| dT | 243.1 | enhanced | 127.05 | enhanced | 35 | 40 | 3 | Positive |
| [$^{13}C_{10}$, $^{15}N_2$]dT | 255.12 | wide | 130.07 | wide | 50 | 8 | 5 | Positive |

4.8 Method Validation and Data Processing

Figure 7A:
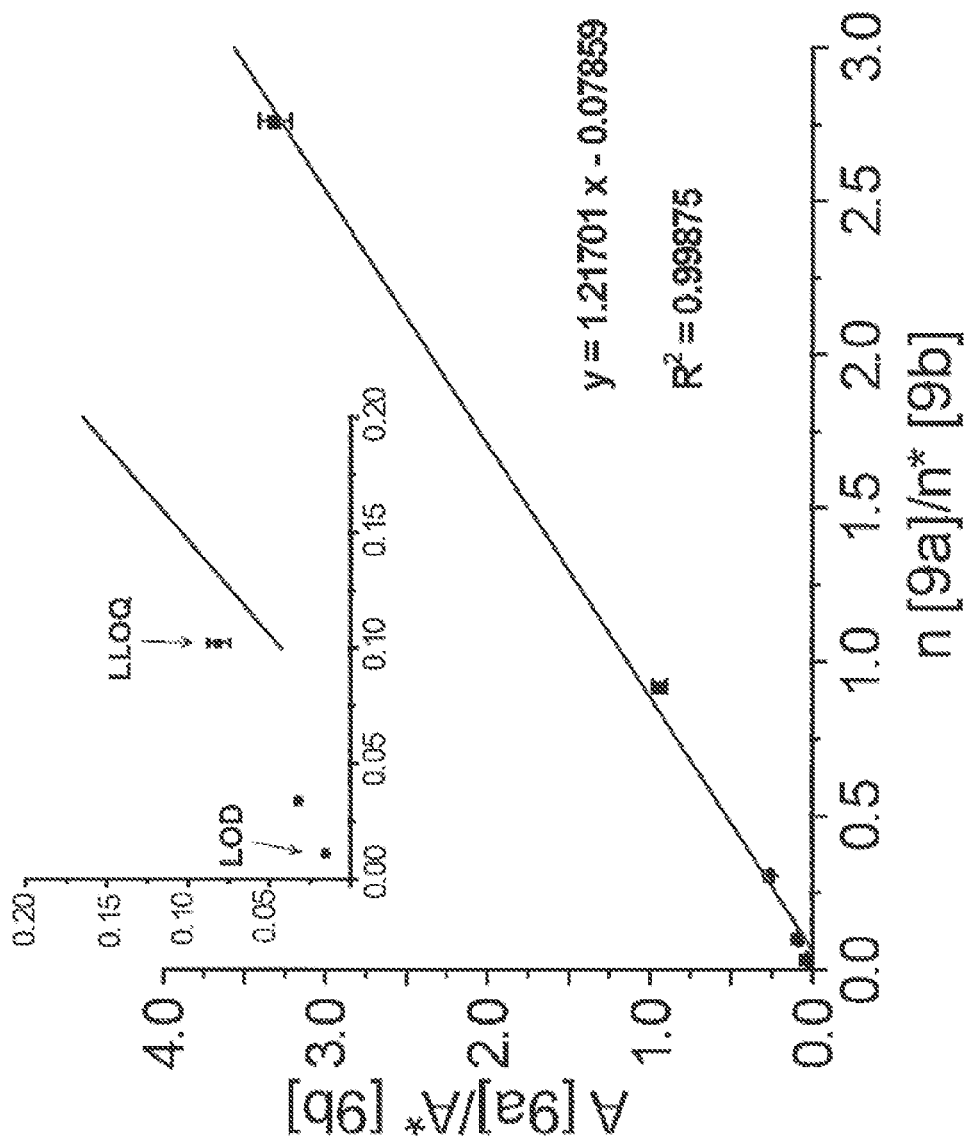
Figure 7B:
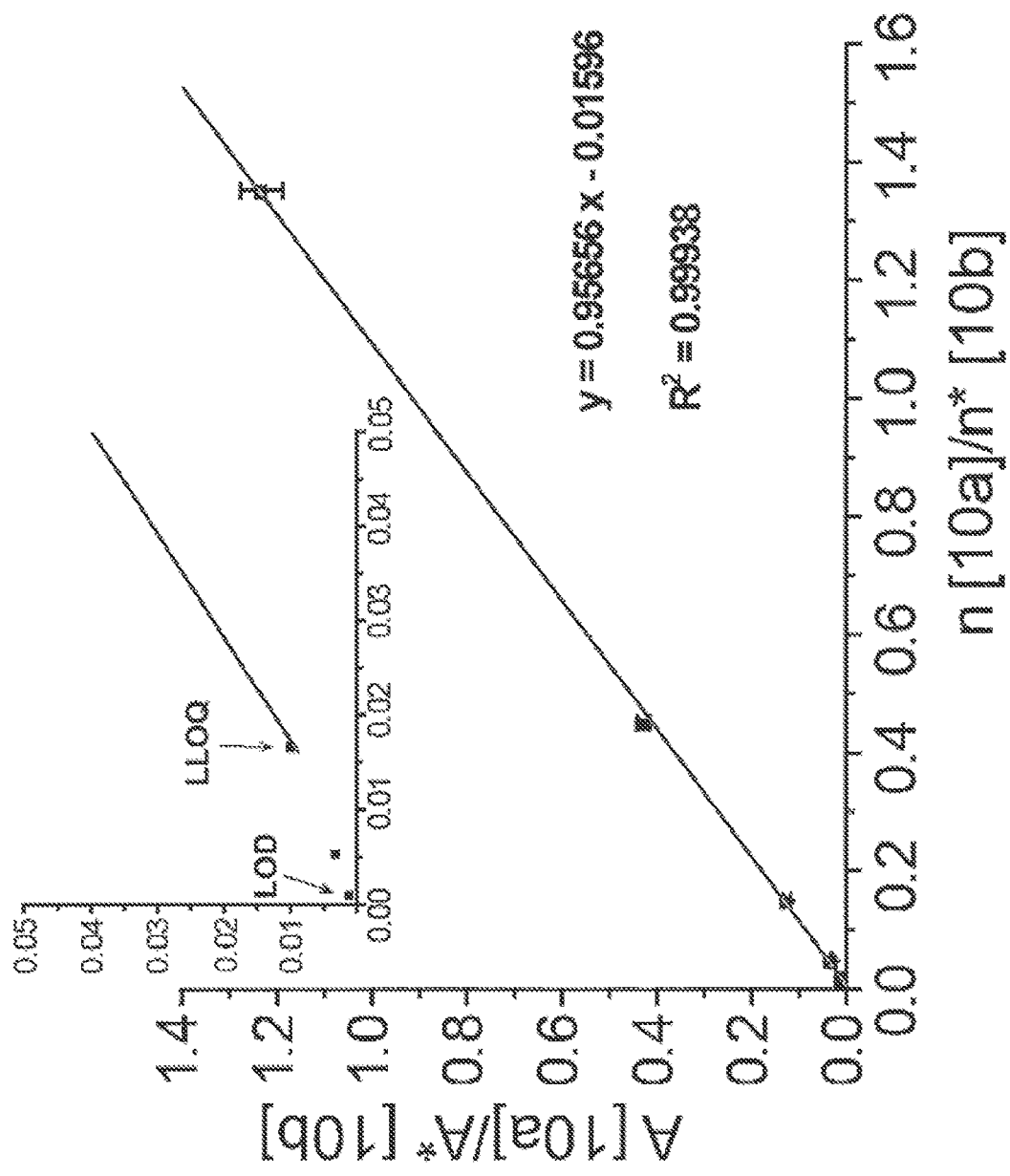

Method validation and data processing were performed as described in earlier published work (24). In order to obtain calibration curves each standard (5-8 standard concentrations) was analyzed as technical triplicate and linear regression was applied using Origin® 6.0 (Microcal™). Therefore, the ratio of the area under the curve (A/A*) of the unlabelled derivatized abasic site 9a and 10a to the internal standard (*) was plotted against the ratio of the amount of substance (n/n*) of the unlabelled derivatized abasic site 9a and 10a, respectively, to the internal standard (*) (see FIG. 7). Calibration functions were calculated without weighing. Acceptable precision (<20% relative s.d.) and accuracy (80-124%) were achieved. The precision was obtained when A/A* ratios, measured in technical triplicates for each calibration standard, had standard deviations <20%. The accuracy was the ratio of the used to the calculated amount of substance in percent for each concentration. To prove the accuracy, we used the respective calibration function for calculation of the substance amount n from A/A* ratio for each calibration standard.

The lower limit of detection (LOD) was defined as thrice the response of the MS-signal of the respective compound obtained at a blank. The lower limit of quantification (LLOQ) was defined as the lowest concentration fulfilling the requirements of accuracy and precision and achieving a response higher than the LOD. A compilation of LLOQs and LOD is shown in Table 2.

TABLE 2

Compilation of absolute lower limits of quantification [fmol] (LLOQ and relative LLOQs [per dN] depending on the amount of DNA digested. The relative LLOQs were calculated by generating ratios of the absolute LLOQ [fmol] to the total amount of nucleosides (N; [fmol]) in the respective amount of DNA [μg]. The total amount of nucleosides were obtained by using the average molar mass of 308.91 g mol$^{-1}$ for the monomeric DNA entity by taking the G-content (21% G) in mESC into account.

| DNA amount | Absolute LOD [fmol] | Absolute LLOQ [fmol] | Relative LLOQ [per dN] 5 μg | Relative LLOQ [per dN] 20 μg |
|---|---|---|---|---|
| 9a | 0.11 | 1.02 | 6.3E–08 | 1.57E–8 |
| 10a | 0.11 | 1.01 | 6.3E–08 | 1.56E–8 |

4.9 Preparation of a Synthetic 13-Mer Oligonucleotide with Defined Abasic Site Oligonucletides (5'-GTA ATG UGC TAG G-3' and 3'-CAT TAC ACG ATC C-5', à 15 nmol, Metabion) were incubated in UDG-buffer (150 μL, 20 mM Tris-HCl, pH=8.0, 1 mM DTT, 1.0 mM EDTA, New England Biolabs) at 95° C. for 5 minutes and then slowly cooled to rt. UDG (5.0 μL, 25 units, New England Biolabs) was added, carefully mixed and the mixture was incubated for 2 hours at 37° C. The oligonucleotide was then isolated through chloroform/phenol extraction as described in the following paragraph. A CHCl$_3$/phenol solution (200 μL, Roti Phenol) was added, vortexed for 30 seconds and centrifuged for 3 minutes at rt and 13400 rpm. The aqueous phase was removed carefully and CHCl$_3$/phenol treatment was repeated twice.

After addition of NaOAc (20 µL, 3M), the oligonucleotide was precipitated with i-PrOH (600 µL). The resulting DNA pellet was centrifuged at rt for 30 (15000 rpm), washed with cold EtOH (300 µL) and centrifuged at 4° C. and 15000 rpm for another 30 minutes. The washing step was repeated once more, the supernatant removed and the pellet was dried on air for five minutes before the oligonucleotide was re-dissolved in ddH$_2$O (150 µL). The identity was finally confirmed by MALDI-TOF analysis.

4.10 Reaction Kinetics on Synthetic Oligo with Defined Abasic Site

In a total reaction volume of 20 µL, of the oligonucleotide (300 pmol) was buffered with HEPES buffer (20 mM, pH=7.5) and Na$_2$EDTA (0.1 mM) and 1 (1.26 µL of 23.8 mM stock) was added. The reaction (37° C., 800 rpm, Eppendorf comfort thermomixer) was started after vortexing the mixture for 5 seconds and after specific time points (t=15 s, 30 s, 45 s, 90 s, 120 s, 150 s, 180 s, 4 min, 6 min, 8 min, 15 min, 20 min) stopped through addition of acetone (200 µL) and freezing the aliquots in liquid nitrogen. Excess of acetone was removed on a speed vac (RVC-2-33 IR, Christ) and was filtered on a AcroPrep Advance 96 filter plate (0.20 µm Supor, Pall Life Sciences). 75 pmol of DNA were subsequently injected into a Dionex micro HPLC system and reaction products were separated using a Zorbax SB-C$_{18}$ column (0.55×250 mm, 5.0 µm pore size) with a flow rate of 350 µL/min. The analysis was run at a column temperature of 60° C. and a gradient of 0%->20% buffer B in 45 min (whereas buffer A=10 mM TEAB, pH=7.5 in H$_2$O and buffer B=10 mM TEAB, pH=7.5 in 80% MeCN/H$_2$O). Integration of the obtained UV signals (FIG. 8) finally showed that the reaction of 1 with abasic sites on an ODN is complete after 20 min and that no other fragments were generated under physiological conditions.

4.11 Efficiency of Enzymatic Digestion

In order to verify if the bulky derivatized abasic site can be excised by the enzyme cocktail described above, we quantified the amount of abasic sites that were formed with the oligo mentioned in the section above. An aliquot of the oligo that was reacted with reagent 1a for 40 minutes was diluted ¼000, a certain amount of labelled internal standard was added and the mixture digested to the nucleoside level. We determined a total amount of 136 pmol of abasic sites. The amount of dG of the same oligo was quantified by its UV trace and was accounted to 762 pmol. Since there are six dG bases in the double stranded construct, one would expect an amount of abasic sites that would constitute to ⅙ of the amount of dG (127 pmol) showing that the digest was complete and the hydrolytic enzymes were not hindered by the abasic site adduct.

4.12 Reaction Kinetics on Abasic Sites in Genomic DNA

Figure 9:
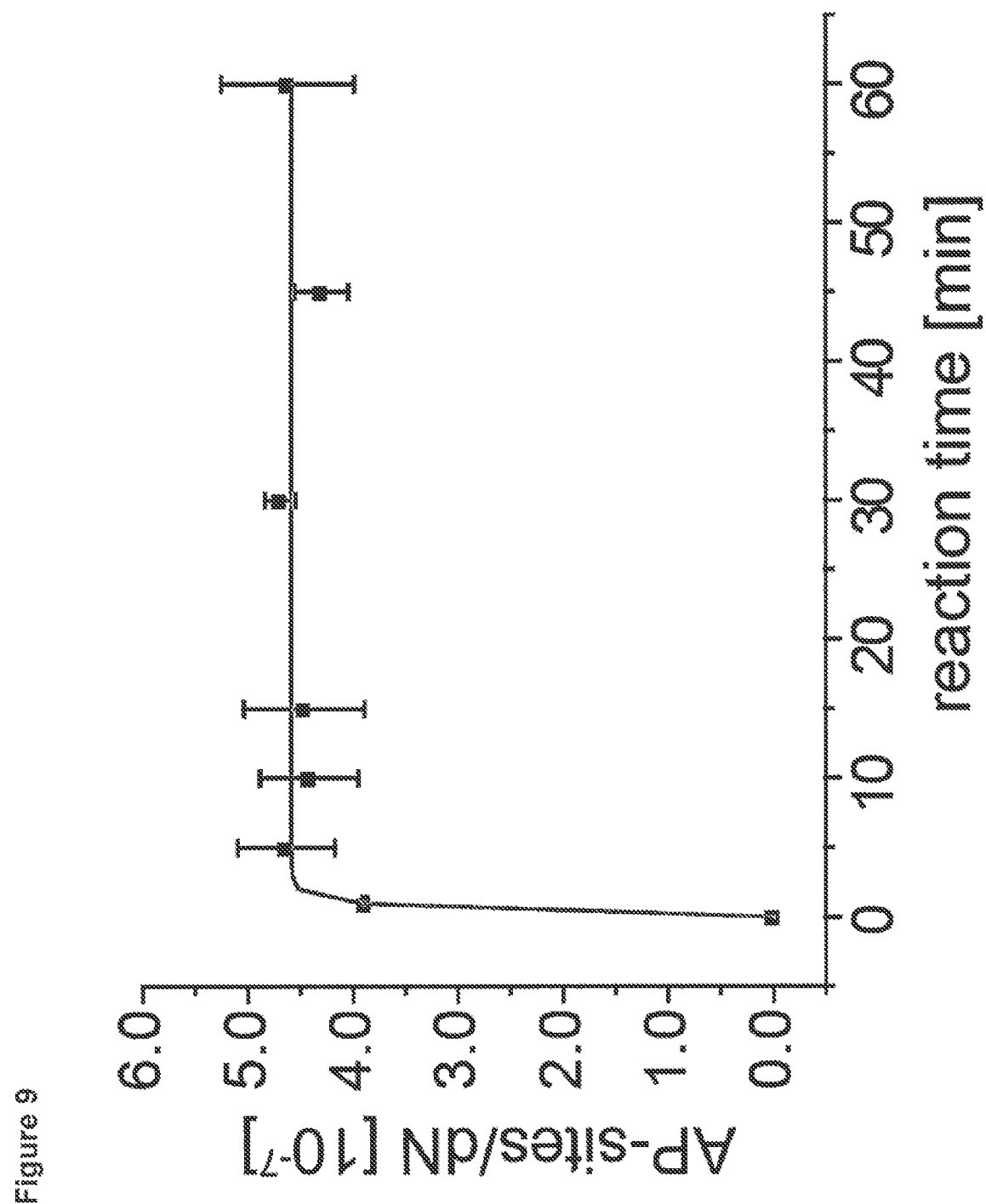

Reactions were carried out by derivatizing 5 µg of gDNA with 1 using the same conditions as mentioned above (Derivatization of genomic DNA with 1). The reaction was stopped through the addition of 1-naphthylaldehyde (66.7 µL, 2M in i-PrOH) at specific time points (t=1 min, 2.5 min, 5 min, 10 min, 20 min, 30 min, 60 min). Reaction aliquots were finally digested to the nucleoside level and quantified (FIG. 9). After 5 min of reaction time, all abasic sites were derivatized and a prolonged incubation up to 60 minutes shows that no abasic sites are generated artificially under the used conditions.

5. Synthesis of a Thiol-Reactive Probe and Use in MS Analysis of Glutathione (GSH)

Figure 10:
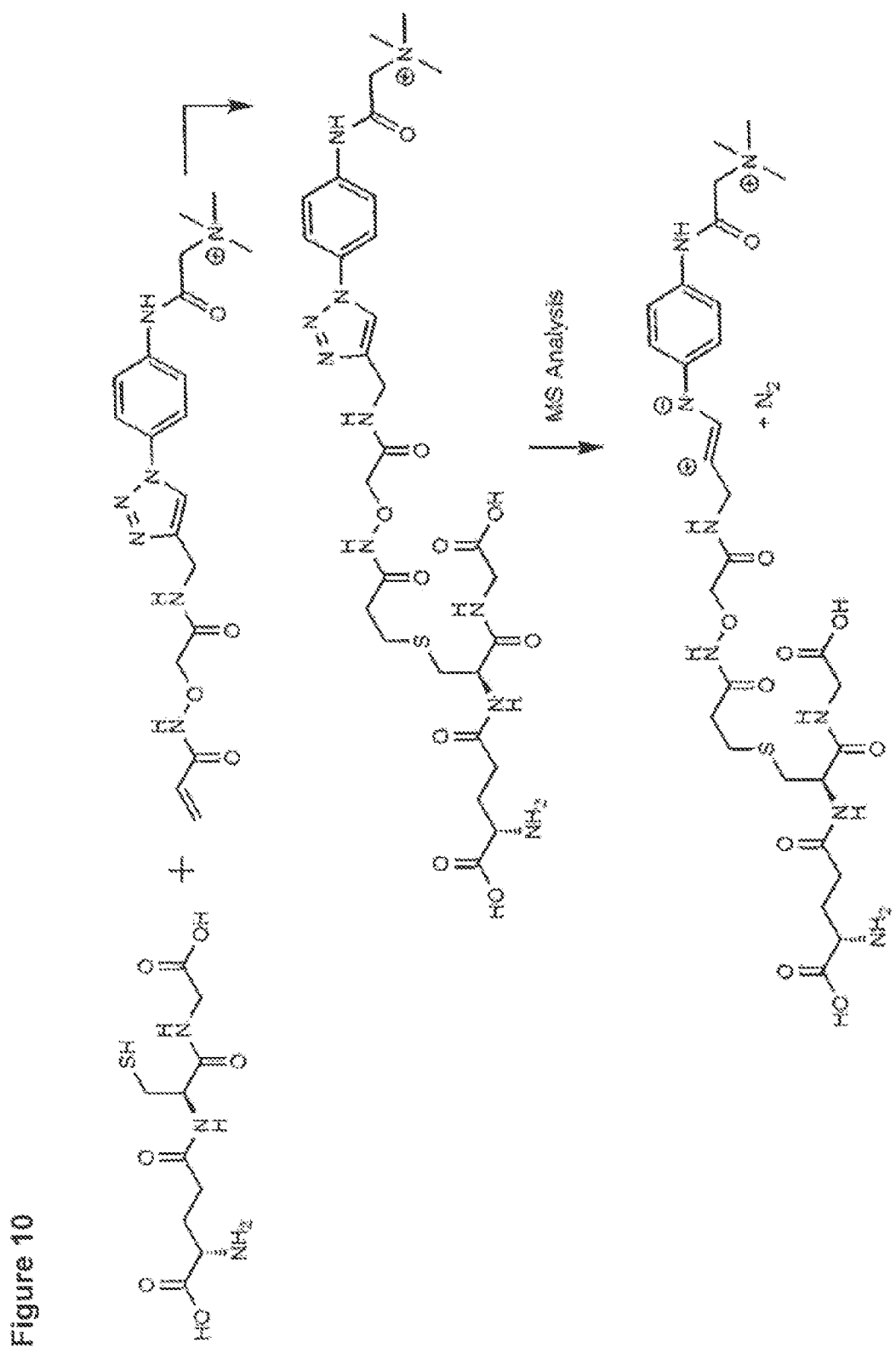

As an example for a probe capable of reacting with a thiol-functional group on an analyte molecule, an acrylamide reagent was synthesized and tested in the MS analysis of glutathione (GSH). The reaction scheme is shown in FIG. 10.

5.1 Synthesis of the Acrylamide Probe

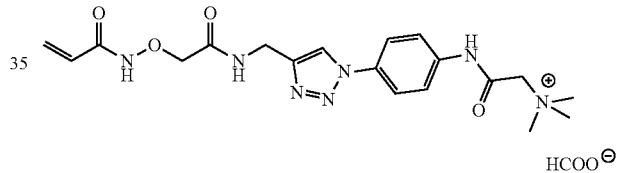

First, hydroxylamine probe (20 mg, 0.044 mmol, 1.0 eq) was dissolved in a mixture of EtOAc/H$_2$O (2:1, 3.0 mL), Na$_2$CO$_3$ (19 mg, 0.176 mmol, 4.0 eq) was added and cooled to 0° C. Acyloyl chloride (120 µL, 1.47 mmol, 33 eq) was added under vigorous stirring and the reaction mixture was kept at 0° C. for 30 minutes. The volatiles were removed through lyophylization and the crude mixture was purified via semi preparative HPLC (0%-->40% buffer B in 40 minutes, buffer A: 25 mM NH$_4$HCOO, pH=4.3 in H$_2$O, buffer B: 20% buffer A in MeCN) using a Nucleodur C18ec column from Machery & Nagel. Fractions containing the desired compound were finally lyophylized to yield the product (6.0 mg, 0.013 mmol, 30%) of a brownish oil.

$^1$H-NMR (400 MHz, D$_2$O), δ (ppm): 8.42 (s, 1H), 8.33 (s, 1H), 7.76 (d, J=9.0 Hz, 2H), 7.69 (d, 9.0 Hz), 6.16 (d, J=16.6 Hz, 1H), 6.10 (d, J=10.4 Hz, 1H), 5.76 (d, J=10.7 Hz), 4.61 (s, 2H), 4.50 (s, 2H), 4.31 (s, 2H), 3.37 (s, 9H).

$^{13}$C-NMR (121 MHz, D$_2$O), δ (ppm): 170.8, 170.4, 162.8, 144.8, 136.8, 128.9, 125.8, 122.5, 121.9, 74.5, 65.1, 54.3, 34.0.

5.2 Synthesis of the GSH Adduct

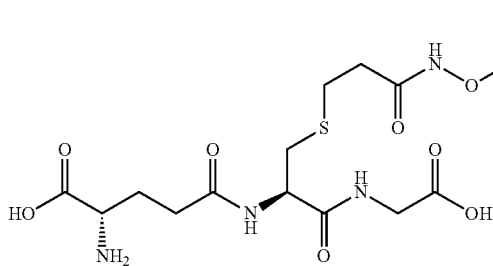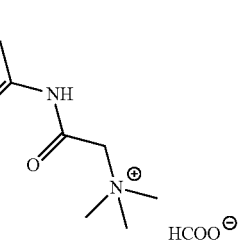

The acryl amide probe (3.0 mg, 0.007 mmol, 1.0 eq) was dissolved in NaHCO$_3$/Na$_2$CO$_3$ buffer (2.0 mL, 60 mM, pH=10). Glutathion (2.0 mg, 0.007 mmol, 1.0 eq) was added and the mixture was incubated at 50° C. for three hours. Volatiles were removed via lyophylization and the crude residue was purified through semipreparative HPLC (0%-->30% buffer B in 40 minutes, buffer A: 25 mM NH$_4$HCOO, pH=4.3 in H$_2$O, buffer B: 20% buffer A in MeCN) using a Nucleodur C18ec column from Machery & Nagel. GSH-adduct was yielded as a colourless solid (4 mg, 0.005 mmol, 74%).

$^1$H-NMR (400 MHz, D$_2$O), δ (ppm): 8.42 (s, 1H), 8.34 (s, 1H), 7.76 (d, J=9.0 Hz, 2H), 7.67 (d, 9.0 Hz), 4.60 (s, 2H), 4.47 (s, 2H), 4.39 (dd, J=8.9 Hz, 4.9 Hz, 1H), 4.31 (s, 2H), 3.72 (t, J=6.3 Hz, 1H), 3.67-3.66 (m, 2H), 3.37 (s, 9H), 2.84 (dd, J=14.1 Hz, 5.0 Hz, 1H), 2.67-2.64 (m, 3H), 2.44 (dd, J=8.6 Hz, 6.7 Hz, 2H), 2.38 (t, J=6.7 Hz, 2H), 2.12-2.05 (m, 2H).

$^{13}$C-NMR (121 MHz, D$_2$O), δ (ppm): 176.0, 174.7, 173.8, 171.6, 171.2, 170.9, 179.4, 162.7, 144.8, 136.9, 133.4, 122.4, 122.4, 121.7, 74.5, 65.1, 54.3, 54.0, 52.9, 43.2, 34.0, 32.5, 32.0, 31.3, 26.9, 26.1.

HRMS: calc. for C$_{29}$H$_{43}$N$_{10}$O$_{10}$S$^+$, [M]$^+$=723.2879, found: 723.2873.

5.3 MS Analysis of the GSH Adduct

The MS analysis shows N$_2$ loss of the single-charged species in the mass spectrometer in the precursor ion scan. The double-charged species shows the N$_2$ loss directly. The results are shown in FIG. 11.

6. Use of a Ketone-Reactive Probe in MS Analysis of Testosterone

As a probe capable of reacting with a ketone-functional group on an analyte molecule, a hydroxylamine reagent was used and tested in the MS analysis of testosterone. The reaction scheme is shown in FIG. 12.

6.1 Synthetic Procedure

Testosterone (20 mg, 0.069 mmol, 1.0 eq) was dissolved in a mixture of H$_2$O/MeCN/MeOH (1:1:1, 1.0 mL containing 0.05% formic acid). The hydroxylamine reagent (28 mg, 0.069 mmol, 1.0 eq) was added and the mixture was incubated at 40° C. over night. Volatiles were removed in vacuo and the crude product was finally purified via semi-preparative HPLC (50% MeCN to 80% MeCN in H$_2$O+ 0.05% formic acid in 40 minutes, 0.5 mL/min). The adduct was yielded as a colourless solid (5 mg, 0.009 mmol, 13%).

Note: The adduct was yielded as a 53/46 mixture of the E/Z isomers which were not assigned.

$^1$H-NMR (400 MHz, CD$_3$CN): δ (ppm)=8.67 (s, 2H), 8.11 (s, 1H), 8.09 (s, 1H), 7.96-7.94 (m, 4H), 7.76-7.73 (m, 4H), 7.10 (s$_t$, J=5.55 Hz, 1H), 7.00 (s$_t$, J=5.68 Hz, 1H), 6.39 (s, 1H), 5.69 (s, 1H), 4.57 (s, 4H), 4.46 (s, 4 h), 4.44 (s, 4H), 3.32 (s, 18H), 1.79-1.20 (m, 30H), 1.07 (s, 3H), 1.06 (s, 3H), 1.03-0.73 (m, 10H), 0.71 (s, 3H), 0.68 (s, 3H).

$^{13}$C-NMR (121 MHz, CD$_3$CN): δ (ppm)=170.5, 170.4, 168.3, 163.0 (2×C), 162.4, 158.8, 158.2, 156.0, 146.7, 146.3, 139.7 (2×C), 133.6, 121.7, 121.6, 121.4, 121.3, 121.1, 116.6, 110.5, 81.3, 81.0, 73.2, 72.9, 65.9, 54.7, 54.5, 51.0, 50.9, 43.1, 43.0, 39.4, 38.4, 37.1, 36.9, 36.6, 36.1, 36.0, 35.0, 34.7, 34.6, 33.1, 32.6, 32.5, 32.2, 30.3, 30.2, 24.8, 23.6, 21.3, 21.1, 19.9, 17.9, 17.7, 11.1, 11.0.

HRMS (ESI): calculated for C$_{35}$H$_{50}$N$_7$O$_4$$^+$ [M$^+$]: 632.3919, found: 632.3915.

6.2 Details of Mass Spectrometry

The testosterone adduct was dissolved in water/acetonitrile (1:1) in a stock concentration of 2.1 mM. A serial dilution with the same solvent mixture finally gave a solution with a concentration of 0.12 pM. The adduct was subjected to UHPLC-QQQ-MS using a flow-rate of 0.35 mL/min with a gradient starting from 50% buffer B (Acetonitrile with 0.0075% formic acid), whereas an injection of 1.0 µL of this solution equalled 0.12 amol. This amount was still detectable in the mass spectrometer with mass transition of 632.4→604.4 and the qualifier transition of 632.4→192.1.

In comparison, pure testosterone was dissolved in EtOH/acetonitrile (1:1) in a stock concentration of 11.04 mM. A serial dilution was performed with the same solvent mixture and gave a final concentration of 11 µM. This solution was again subjected to UHPLC-QQQ-MS with a flow-rate 0f 0.35 mL/min using a gradient starting from 50% buffer B (Acetonitrile with 0.0075% formic acid), whereas an injection volume of 2.0 µL of this stock equalled 22 amol. This amount was still detectable in the mass spectrometer with a mass transition of 289.2→109.2. Injection of only 1.0 µL did not show a signal above background noise.

In summary, the adduct can be detected with 185 times higher sensitivity than the underivatized testosterone.

Figure 13:
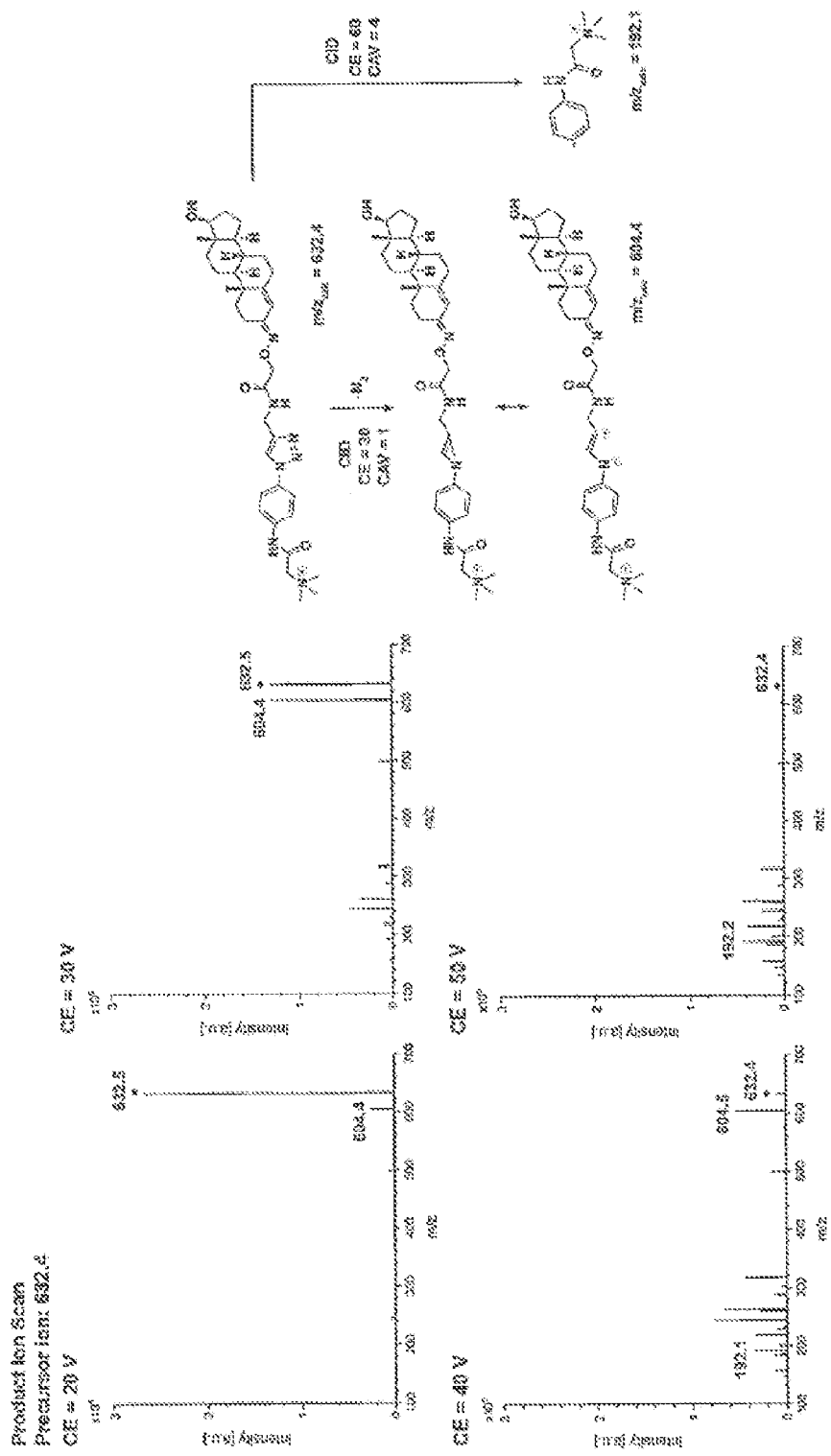
Figure 15:
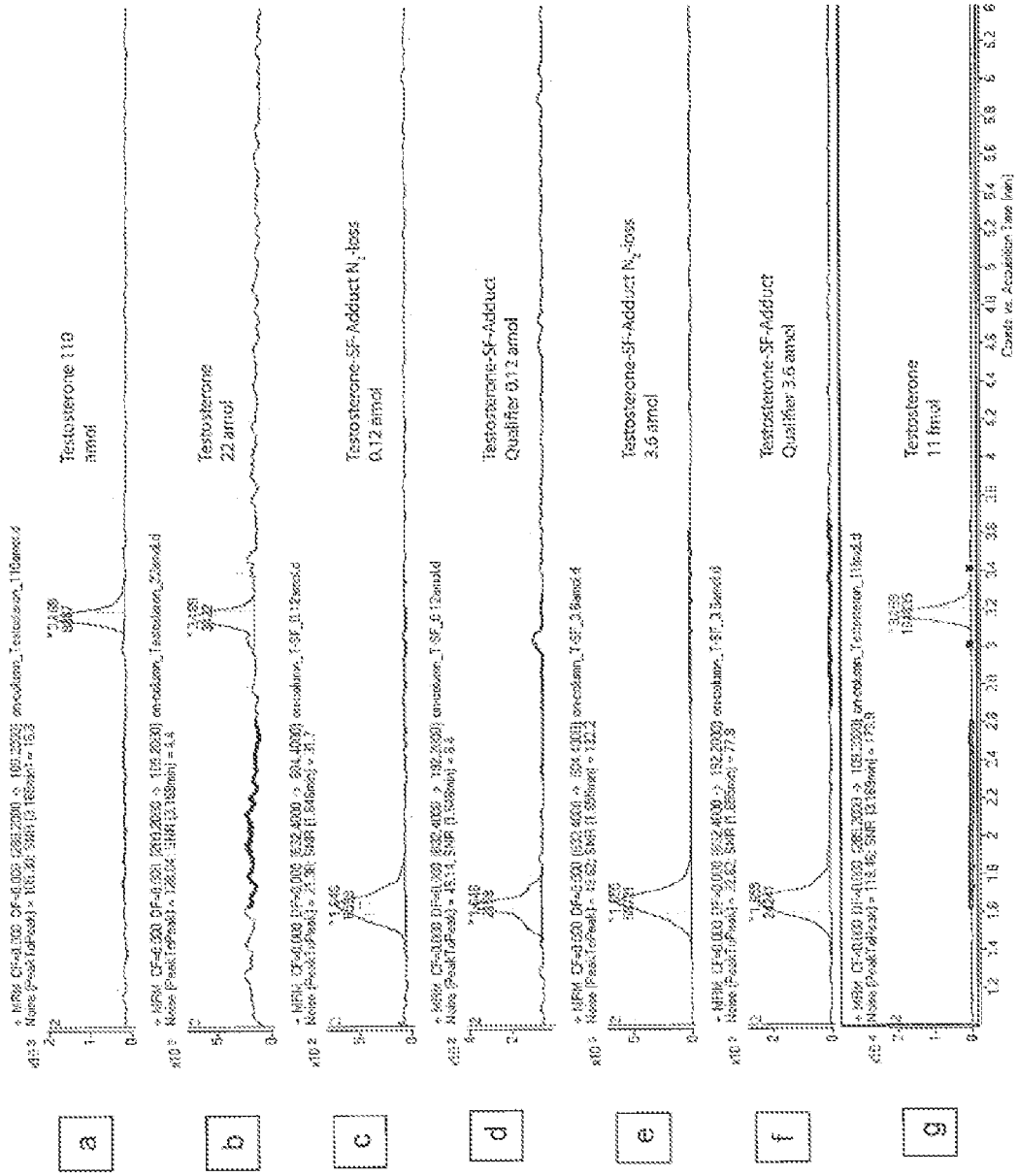

The results are shown in FIGS. 13-15.

7. Use of a Reactive Ester Probe in MS Analysis of Dopamine

The following adduct of dopamine and a reactive ester compound was prepared

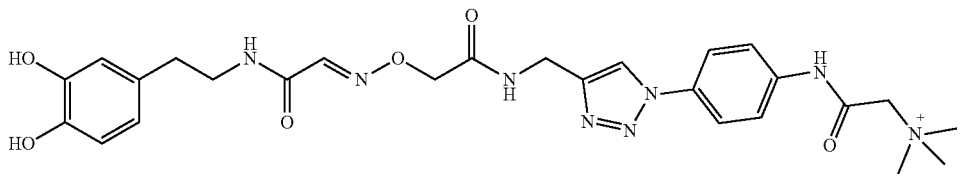

and characterized by HR-MS and UHPLC-MS/MS.

HR-MS: calculated for $C_{26}H_{33}N_8O_6^+$: 553.2518, found: 553.2518.

The adduct was dissolved and diluted in MeOH/Acetonitrile (1:1) and subjected to UHPLC-MS/MS. Performance of a product ion scan identified the nitrogen loss with a peak at 525.2 resulting from fragmenting the molecule ion of a m/z of 553.4.

LIST OF REFERENCES

1. Kim, Y. J. & Wilson, D. M., 3rd. Overview of base excision repair biochemistry. *Curr Mol Pharmacol* 5, 3-13, (2012).
2. Krokan, H. E. & Bjoras, M. Base excision repair. *Cold Spring Harb Perspect Biol* 5, a012583, (2013).
3. Jacobs, A. L. & Schar, P. DNA glycosylases: in DNA repair and beyond. *Chromosoma* 121, 1-20, (2012).
4. Maiti, A. & Drohat, A. C. Thymine DNA glycosylase can rapidly excise 5-formylcytosine and 5-carboxylcytosine: potential implications for active demethylation of CpG sites. *J Biol Chem* 286, 35334-35338, (2011).
5. He, Y. F. et al. Tet-mediated formation of 5-carboxylcytosine and its excision by TDG in mammalian DNA. *Science* 333, 1303-1307, (2011).
6. Ito, S. et al. Tet proteins can convert 5-methylcytosine to 5-formylcytosine and 5-carboxylcytosine. *Science* 333, 1300-1303, (2011).
7. Kalia, J. & Raines, R. T. Hydrolytic stability of hydrazones and oximes. *Angew Chem Int Ed Engl* 47, 7523-7526, (2008).
8. Kojima, N., Takebayashi, T., Mikami, A., Ohtsuka, E. & Komatsu, Y. Construction of highly reactive probes for abasic site detection by introduction of an aromatic and a guanidine residue into an aminooxy group. *J Am Chem Soc* 131, 13208-13209, (2009).
9. Roberts, K. P., Sobrino, J. A., Payton, J., Mason, L. B. & Turesky, R. J. Determination of apurinic/apyrimidinic lesions in DNA with high-performance liquid chromatography and tandem mass spectrometry. *Chem Res Toxicol* 19, 300-309, (2006).
10. Cortellino, S. et al. Thymine DNA glycosylase is essential for active DNA demethylation by linked deamination-base excision repair. *Cell* 146, 67-79, (2011).
11. Cortazar, D. et al. Embryonic lethal phenotype reveals a function of TDG in maintaining epigenetic stability. *Nature* 470, 419-423, (2011).
12. Cheng, K. C., Cahill, D. S., Kasai, H., Nishimura, S. & Loeb, L. A. 8-Hydroxyguanine, an abundant form of oxidative DNA damage, causes G----T and A----C substitutions. *J Biol Chem* 267, 166-172, (1992).
13. Lindahl, T. Instability and decay of the primary structure of DNA. *Nature* 362, 709-715, (1993).
14. Zharkov, D. O., Rosenquist, T. A., Gerchman, S. E. & Grollman, A. P. Substrate specificity and reaction mechanism of murine 8-oxoguanine-DNA glycosylase. *J Biol Chem* 275, 28607-28617, (2000).
15. Hill, J. W., Hazra, T. K., Izumi, T. & Mitra, S. Stimulation of human 8-oxoguanine-DNA glycosylase by AP-endonuclease: potential coordination of the initial steps in base excision repair. *Nucleic Acids Res* 29, 430-438, (2001).
16. Krokan, H. E., Drablos, F. & Slupphaug, G. Uracil in DNA-occurrence, consequences and repair. *Oncogene* 21, 8935-8948, (2002).
17. Morgan, H. D., Dean, W., Coker, H. A., Reik, W. & Petersen-Mahrt, S. K. Activation-induced cytidine deaminase deaminates 5-methylcytosine in DNA and is expressed in pluripotent tissues: implications for epigenetic reprogramming. *J Biol Chem* 279, 52353-52360, (2004).
18. Nilsen, H. et al. Excision of deaminated cytosine from the vertebrate genome: role of the SMUG1 uracil-DNA glycosylase. *Embo J* 20, 4278-4286, (2001).
19. Visnes, T. et al. Uracil in DNA and its processing by different DNA glycosylases. *Philos T R Soc B* 364, 563-568, (2009).
20. Schomacher, L. et al. Neil DNA glycosylases promote substrate turnover by Tdg during DNA demethylation. *Nat Struct Mol Biol* 23, 116-124, (2016).
21. Tsumura, A. et al. Maintenance of self-renewal ability of mouse embryonic stem cells in the absence of DNA methyltransferases Dnmt1, Dnmt3a and Dnmt3b. *Genes Cells* 11, 805-814, (2006).
22. Li, E., Bestor, T. H. & Jaenisch, R. Targeted mutation of the DNA methyltransferase gene results in embryonic lethality. *Cell* 69, 915-926, (1992).
23. Cao, H. & Wang, Y. Collisionally activated dissociation of protonated 2'-deoxycytidine, 2'-deoxyuridine, and their oxidatively damaged derivatives. *J. Am. Soc. Mass Spectrom.* 17, 1335-1341, (2006).
24. Schroder, A. S. et al. Synthesis of a DNA promoter segment containing all four epigenetic nucleosides: 5-methyl-, 5-hydroxymethyl-, 5-formyl-, and 5-carboxy-2'-deoxycytidine. *Angew Chem Int Ed Engl* 53, 315-318, (2014).
25. Schiesser, S. et al. Deamination, oxidation, and C—C bond cleavage reactivity of 5-hydroxymethylcytosine, 5-formylcytosine, and 5-carboxycytosine. *J Am Chem Soc* 135, 14593-14599, (2013).
26. Spruijt, C. G. et al. Dynamic readers for 5-(hydroxy) methylcytosine and its oxidized derivatives. *Cell* 152, 1146-1159, (2013).
27. Wang, J. et al. Quantification of oxidative DNA lesions in tissues of Long-Evans Cinnamon rats by capillary high-performance liquid chromatography-tandem mass spectrometry coupled with stable isotope-dilution method. *Anal. Chem.* 83, 2201-2209, (2011).

The invention claimed is:

1. Use of a compound of the general formula (I):

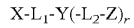

wherein
- X is a reactive group capable of reacting with an analyte molecule, whereby a covalent bond with the analyte molecule is formed,
- $L_1$ is a bond or a spacer,
- Y is a neutral ion loss unit, which itself is neutral and which, under conditions of mass spectrometry, is capable of fragmentation, whereby a neutral species is released, and wherein Y comprises a 4-, 5-, or 6-membered heterocyclic moiety,
- $L_2$ is a bond or a spacer,
- Z is a charge unit comprising
  - (i) at least one positively charged moiety having a $pK_a$ of 10 or higher, or
  - (ii) at least one negatively charged moiety having a $pK_b$ of 10 or higher,
- r is 1,
- including any salt thereof,
- or of a composition or kit comprising at least one compound (I)
- for the mass spectrometric determination of an analyte molecule.

2. The use of claim 1, wherein the reactive group X is a carbonyl-reactive group, a dienophilic group, a carboxylate reactive group, a phenol reactive group, an amino reactive group, a hydroxyl reactive group, or a thiol reactive group.

3. The use of claim 1, wherein the reactive group X is a carbonyl-reactive group selected from the group consisting of
  (i) a hydrazine group,
  (ii) a hydrazone group,
  (iii) a hydroxylamino group, and
  (iv) a dithiol group.

4. The use of claim 1, wherein the reactive group X is a haloacetyl group.

5. The use of claim 1, wherein the reactive group X is an amino-reactive group selected from the group consisting of an active ester group, a hydroxybenzotrialzole (HOBt) ester and 1-hydroxy-7-azabenzotriazole (HOAt) ester group.

6. The use of claim 1, wherein neutral ion loss unit Y is capable of fragmentation by a reverse cycloaddition reaction, and wherein neutral ion loss unit Y comprises a cyclic azo compound or a 5-membered heterocyclic moiety having at least 2 heteroatoms adjacent to each other.

7. The use of claim 1, wherein the neutral species is an inorganic molecule selected from the group consisting of SO, $SO_2$, CO, $CO_2$, NO, $NO_2$ and $N_2$.

8. The use of claim 1, wherein the charge unit Z comprises
  (i) at least one positively charged moiety selected from the group consisting of a primary, secondary, tertiary or quaternary ammonium group and a phosphonium group having a $pK_a$ of 10 or higher, or
  (ii) at least one negatively charged moiety selected from the group consisting of a phosphate, sulphate, sulphonate and carboxylate group having a $pK_b$ of 10 or higher.

9. The use of claim 1, wherein the charge unit Z comprises or consists of one permanently positively charged moiety.

10. The use of claim 1, wherein said compound (I) further, under conditions of mass spectrometry, is capable of an alternative fragmentation, whereby a second neutral species different from the first neutral species is released.

11. The use of claim 1, wherein said compound (I) is of the general formula (Ia) or (Ib):

X-$L_1$-Y-$L_2$-Z   (Ia), $X^1$-$L_1$-$Y^1$(-$L_2$-Z)$_r$   (Ib)

wherein
- X, $L_1$, $L_2$, Y, Z and r are as defined in claim 1,
- $X^1$ is a carbonyl-reactive group, and
- $Y^1$ is a neutral ion loss unit comprising
  (i) a 4-, 5- or 6-membered heterocyclic moiety which, under conditions of mass spectrometry, is capable of fragmentation, whereby a first neutral species is released, and
  (ii) optionally a moiety, which under conditions of mass spectrometry, is capable of an alternative fragmentation, whereby a second neutral species different from the first neutral species is released.

12. The use of claim 1, wherein said compound (I) is of the general formula (Ic):

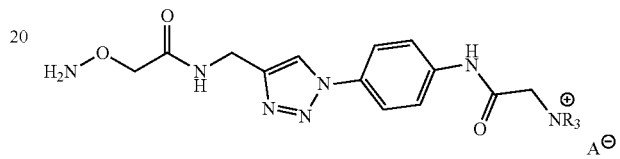

wherein R is in each case independently H or $C_{1-4}$ alkyl and A is an anion.

13. The use of claim 1, wherein compound (I) is an isotopologue comprising at least one isotope selected from D, $^{13}C$, $^{15}N$ and/or $^{18}O$.

14. A method for the mass spectrometric determination of an analyte molecule comprising the steps:
  (a) covalently reacting the analyte molecule with a compound of general formula (I) as defined in claim 1, whereby an adduct of the analyte molecule and the reagent is formed, and
  (b) subjecting the adduct from step (a) to a mass spectrometric analysis, wherein the mass spectrometric analysis step (b) comprises:
  (i) subjecting an ion of the adduct to a first stage of mass spectrometric analysis, whereby the ion of the adduct is characterised according to its mass/charge (m/z) ratio,
  (ii) causing fragmentation of the adduct ion, whereby a first neutral species is released and a daughter ion of the adduct is generated, wherein the daughter ion of the adduct differs in its m/z ratio from the adduct ion, and
  (iii) subjecting the daughter ion of the adduct to a second stage of mass spectrometric analysis, whereby the daughter ion of the adduct is characterized according to its m/z ratio, and/or
  wherein (ii) may further comprise alternative fragmentation of the adduct ion, whereby a second neutral species different from the first neutral species is released and a second daughter ion of the adduct is generated, and
  wherein (iii) may further comprise subjecting the first and second daughter ions of the adduct to a second stage of mass spectrometric analysis, whereby the first and second daughter ions of the adduct are characterised according to their m/z ratios.

15. A reagent, which is a compound of formula (Ia)

X-$L_1$-Y-$L_2$-Z wherein

X is a carbonyl reactive group, dienophilic group, a carboxylate reactive group, a phenol reactive group, an amino reactive group, a hydroxyl reactive group, or a thiol reactive group, and wherein X is no acrylester, $L_1$ is a bond or a spacer, Y is a neutral ion loss unit, which itself is neutral and which, under conditions of mass spectrometry, is capable of fragmentation, whereby a neutral species is released, and wherein Y consists of a 4-, 5-, or 6-membered heterocyclic moiety, $L_2$ is a bond or a spacer, Z is a charge unit comprising at least one permanently positively charged moiety selected from the group consisting of a primary, secondary, tertiary or quaternary ammonium group and a phosphonium group, wherein the overall molecule has a $pK_a$ of 10 or higher, including any salt thereof, or a composition or kit comprising at least one compound (Ia).

16. The reagent of claim 15, wherein Y consists of a cyclic azo compound or a 5-membered heterocyclic moiety having at least 2 heteroatoms adjacent to each other and, under conditions of mass spectrometry, is capable of fragmentation by reverse cycloaddition reaction, whereby a neutral species is released.

17. The reagent of claim 15, which is of formula (Ic):

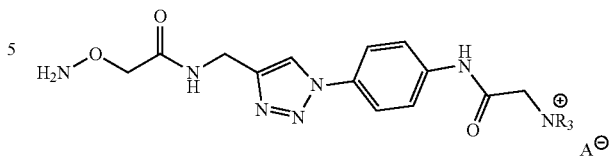

wherein R is in each case independently H or $C_{1-4}$ alkyl and A is an anion.

18. A composition or kit comprising a plurality of isotopically different reagents of claim 15.

19. Use of a covalent adduct formed by reaction of the compound of general formula (I) as defined in claim 1 and an analyte molecule, for the mass spectrometric determination of an analyte molecule, wherein the covalent adduct is a compound of the general formula (II):

$$T\text{-}X'\text{-}L_1\text{-}Y(\text{-}L_2\text{-}Z)_r$$

wherein

T is an analyte molecule,

X' is a moiety resulting from the reaction of a group X on the compound (I) with an analyte molecule and $L_1$, Y, $L_2$, Z and r are as defined in claim 1.

20. The use of claim 19 as a calibrator and/or as a standard.

* * * * *